(12) United States Patent
Strobel et al.

(10) Patent No.: US 9,090,921 B2
(45) Date of Patent: *Jul. 28, 2015

(54) METHOD OF PRODUCING VOLATILE ORGANIC COMPOUNDS FROM MICROORGANISMS

(71) Applicants: Gary A. Strobel, Bozeman, MT (US); Angela R. Tomsheck, Oilmont, MT (US)

(72) Inventors: Gary A. Strobel, Bozeman, MT (US); Angela R. Tomsheck, Oilmont, MT (US)

(*) Notice: Subject to any disclaimer, the term of this patent is extended or adjusted under 35 U.S.C. 154(b) by 0 days.

This patent is subject to a terminal disclaimer.

(21) Appl. No.: 13/796,469

(22) Filed: Mar. 12, 2013

(65) Prior Publication Data

US 2013/0252289 A1 Sep. 26, 2013

Related U.S. Application Data

(63) Continuation-in-part of application No. 13/110,688, filed on May 18, 2011, now Pat. No. 8,501,458.

(60) Provisional application No. 61/345,918, filed on May 18, 2010.

(51) Int. Cl.
| | |
|---|---|
| *C12P 1/00* | (2006.01) |
| *C12P 17/06* | (2006.01) |
| *C12P 5/00* | (2006.01) |
| *C12P 7/06* | (2006.01) |
| *C12R 1/645* | (2006.01) |

(52) U.S. Cl.
CPC ............... *C12P 17/06* (2013.01); *C12P 5/002* (2013.01); *C12P 7/06* (2013.01); *C12P 7/065* (2013.01); *C12R 1/645* (2013.01); *Y02E 50/17* (2013.01)

(58) Field of Classification Search
CPC ......... C12R 1/645; C12P 17/06; C12P 5/002; C12P 7/065; C12P 7/26; C12P 17/181; C12P 5/007; C12P 7/06; Y02E 50/17
See application file for complete search history.

(56) References Cited

U.S. PATENT DOCUMENTS

| | | | |
|---|---|---|---|
| 4,275,234 | A | 6/1981 | Baniel et al. |
| 4,297,109 | A | 10/1981 | Sugito et al. |
| 5,348,872 | A | 9/1994 | Lin et al. |
| 5,510,526 | A | 4/1996 | Baniel et al. |
| 5,641,406 | A | 6/1997 | Sarhaddar et al. |
| 5,831,122 | A | 11/1998 | Eyal |
| 2005/0220769 | A1 | 10/2005 | Strobel et al. |
| 2009/0123977 | A1* | 5/2009 | Mendez et al. ............ 435/91.4 |

FOREIGN PATENT DOCUMENTS

| | | | | |
|---|---|---|---|---|
| CN | 102071144 | * | 5/2011 | ............ C12N 1/14 |
| WO | WO 93/00440 | | 1/1993 | |

OTHER PUBLICATIONS

Sanchez-Ballesteros et al., Mycologia, 92(5): 967-977, abstract, (2000).*
Kamenarska et al., Botanica Marina, Abstract, 52(1) 2009.*
Azeez, S. (2008). "Fennel. In Chemistry of Spices", pp. 227-241. Edited by Parthasarathy, V.A., Chempakam, B., & Zachariah, T. Cambridge, MA: CAB International.
Barton, A., & Tjandra, J. (1989). "Eucalyptus oil as a cosolvent in water-ethanol-gasoline mixtures." Fuel 68, 11-17.
Bunge, M., et al. (2008). "On-line monitoring of microbial volatile metabolites by proton transfer reaction-mass spectrometry." Appl Environ Microbiol 74, 2179-2186.
Cook, et al. (2007). "*Mentha spicata* essential oils rich in 1,8.cineole and 1,2-epoxy-P-methane derivates from Zakynthos (Ionian Island, W Greece)". The Journal of Essential Oil Research 19, 225-230.
Cosimi, et al., (2009). "Bioactivity and qualitative analysis of some essential oils from Mediterranean plants against stored-product pests: Evaluation of repellency against *Sitophilus zeamais* Matschulsky, *Cryptolestes ferrugineus* (Stephens) and *Tenebrio molitor* (L.)." Journal of Stored Products Research 45, 125-132.
Croteau, et al., (1994). "Biosynthesis of monoterpenes: partial purification, characterization and mechanism of action of 1,8-cineole synthase." Arch-Biochem-Biophys 309, 184-192.
Ezra, et al., (2004a). "New endophytic isolates of *Muscodor albus*, a volatile-antibiotic-producing fungus." Microbiology 150, 4023-4031.
Ezra, et al., (2004b). Proton transfer reaction-mass spectroscopy as a technique to measure volatile emissions of *Muscodor albus*. Plant Science 166, 1471-1477.
Kempler, G.M. (1983). "Production of Flavor Compounds by Microorganisms. III. Terpenenes." B. Production of Monoterpenes by Microorganisms. In Advances in Applied Microbiology, vol. 29, pp. 35-37. Edited by A.I. Laskin. New York, NY: Academic Press, Inc.
Madyastha, K. M. (1984). "Microbial transformations of acyclic monoterpenes." Journal of Chemical Sciences 93, 677-686.
Smith, S.A., et al. (2008) "Bioactive Endophytes Warrant Intensified Exploration and Conservation" PloS 1 Biology Published on-line Aug. 25, 2008. PloS 1 3(8):e3052.
Southwell, et al., (2003), "*Melaleuca teretifolia* chemovars: New Australian sources of citral and 1,8-cineole." Journal of Essential Oil Research 15:339-341.
Strobel, G.A., & Daisy, B. (2003). "Bioprospecting for Microbial Endophytes and Their Natural Products." Microbiology and Biology Reviews 67, 491-502.
Strobel, et al., (2001). "Volatile antimicrobials from *Muscodor albus*, a novel endophytic fungus." Microbiology 147, 2943-2950.
Strobel, et al., (2008). "The production of myco-diesel hydrocarbons and their derivatives by the endophytic fungus *Gliocladium roseum* (NRRL 50072)." Microbiology 154, 3319-3328.
Tan, R., & Zou, W. (2001). "Endophytes: a rich source of functional metabolites." Nat. Prod. Rep. 18, 448-459.
Thomas, et al., (2000). "Plant sources of aroma chemicals and medicines in India." Chemical Industry Digest (Special Millennium Issue), 104-108.

(Continued)

*Primary Examiner* — Blaine Lankford
*Assistant Examiner* — Thomas J Visone
(74) *Attorney, Agent, or Firm* — Riverside Law LLP

(57) ABSTRACT

A method for producing at least one compound selected from the group consisting of 1,8-cineole, and 1-methyl-1,4-cyclohexadiene is also described. The method includes culturing a microorganism on or within a culturing media in a container under conditions sufficient for producing the at least one compound.

11 Claims, 18 Drawing Sheets

(56) References Cited

OTHER PUBLICATIONS

Weyerstahl, et al., (1993). "Constituents of the Leaf Essential Oil of *Persea indica* (L.) K. Spreng." Flavour and Fragrance Journal 8, 201-207.

Worapong, et al., (2001). "*Muscodor albus* anam. nov., an endophyte from *Cinnamomun zeylanicum*." Mycotaxon 79, 67-79.

Griffin et al., (1989) "Protoplast formation and transformation of *Hypoxylon mammatum*." Abstracts of the 1989 APS Annual Meeting. Phytopathology 79:1135; p. 1204.

Zhao et al., (2004) "Study on the Preparation and Regeneration of Protoplast From Taxol-Producing Fungus *Nodulisporium ylviforme*." Nature and Science 2(2):52-59.

Johannesson (2000) Ecology of *Daldinia* spp. With Special Emphasis on *Daldinia zoculata*. Doctoral thesis. Swedish University of Agricultural Sciences Uppsala.

Srutka et al., (2007) "*Daldinia decipiens* and *Entonaema cinnabarina* as fungal symbionts of *Xiphydria* wood wasps." Mycological Research 111:224-231.

Gu et al., (2007) "Cytotoxic benzo[j]fluoranthene metabolites from *Hypoxylon truncatum* IFB-18, an endophyte of *Artemisia annua*." J. Nat. Prod. 70:114-117.

Rapparini et al., (2008) "Effect of arbuscular mycorrhizal (AM) colonization on terpene emission and content of *Artemisia annua* L." Plant Biology 10:108-122.

\* cited by examiner 1-methyl-1,4-cyclohexadiene 1,8-cineole (+)-.alpha.-methylene-.alpha.-fenchocamphorone

```
                        SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized

<400> SEQUENCE: 1
tccgtaggtg aacctgcgg                                                  19

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized

<400> SEQUENCE: 2
tcctccgctt attgatatgc                                                 20
```

METHOD OF PRODUCING VOLATILE ORGANIC COMPOUNDS FROM MICROORGANISMS

CROSS REFERENCE TO RELATED APPLICATIONS

The present application is a continuation-in-part of U.S. patent application Ser. No. 13/110,688, filed May 18, 2011, which is entitled to priority under 35 U.S.C. §119(e) to U.S. Provisional Application No. 61/345,918, filed May 18, 2010, which applications are incorporated by reference herein in their entireties.

STATEMENT REGARDING FEDERALLY SPONSORED RESEARCH OR DEVELOPMENT

This invention was made with government support under CBET0802666 and EFRI-0937613 awarded by the National Science Foundation (NSF), and under N00244-09-1-0070 awarded by the Department of Defense (Navy). The government has certain rights in the invention.

BACKGROUND OF THE INVENTION

The identification and production of volatile organic compounds (VOCs) continues to be a driving force in the development and expansion of many commercial industries. For example, 1,8-cineole, commonly referred to as eucalyptol, is the pharmaceutically active component of *eucalyptus* oil, comprising 70-85% of the essential oil. Traditional uses of *eucalyptus* oil primarily involve non-prescription pharmaceuticals, fragrances and degreasing detergents (Opdyke, 1975, Food and Cosmetics Toxicology 13: 91-112; Hong and Shellock, 1991, American Journal of Physical Medicine and Rehabilitation 70:29-33; Leung, Y. (1980). *Eucalyptus*. New York: Wiley.; Furia, T., & Bellanca, N, (1971), *Fenaroli's Handbook of Flavor Ingredients*. Cleveland, Ohio: Chemical Research Co.; Barton, et al., 1997, Chemistry in Australia 64:4-6). 1,8-Cineole also has potential applications in alternative fuel production as it has been shown to prevent phase separation when used as an additive in ethanol-gasoline fuel blends (Barton and Tjandra, 1989, Fuel 68:11-17), and alternative fuels comprised of a gasoline/eucalyptus oil mixture (with 1,8-cineole as the major fuel component) resulted in an improved octane number and reduced carbon monoxide exhaust (U.S. Pat. No. 4,297,109).

Also, fenchocamphorone is a derivative of fenchol via a fenchene intermediate, both of which are monoterpenes (Croteau, et al., 1988, Journal of Biological Chemistry 263: 15449-15453). Fenchone, also a monoterpene of similar derivations, is a volatile compound that is found as a major constituent of fennel seed oil (Azeez, S. (2008). Fennel. In Chemistry of Spices, pp. 227-241. Edited by Parthasarathy, V. A., Chempakam, B., & Zachariah, T. Cambridge, Mass.: CAB International.). Fennel oil is also considered an essential plant oil and is valued for its strong flavor, but is also recognized as an antioxidant, hepatoprotective agent, anticancer agent, and other biological activities have been described for it (Azeez 2008; Cosimi et al., 2009, Journal of Stored Products Research 45:125-132).

Another example is 1,4-cyclohexadiene, which is a highly flammable cycloalkene that yields the natural monoterpene derivative, γ-terpinene, a component associated with many essential oils. 1,4-Cyclohexadiene also readily oxidizes to benzene by a number of different methods (Breton, et al., 2005, Electrochemistry Communications 7:1445-1448; Smith and Gray, 1990, Catalysis Letters 6:195-200; Hepworth et al., 2002, Aromatic Chemistry, pp. 129-134; Brooks, B. T. (1922). The Cyclic Non-benzoid Hydrocarbons: The Cyclohexane Series. In *The Chemistry of Non-benzoid Hydrocarbons and Their Simple Derivatives*, pp. 278-383. Edited by B. T. Brooks. New York, N.Y.: Chemical Catalog Company, Inc.) which gives it multiple applications in industrial chemistry. Benzene is a natural component of crude oil and gasoline and is a widely used chemical in the production of plastics, nylon, and resins, as well as some types of rubbers, detergents, lubricants, dyes, and pesticides (Agency for Toxic Substances and Disease Registry (ATSDR) (2007). *Toxicological Profile for Benzene (Update)*. Atlanta, Ga.: U.S. Department of Public Health and Human Services, Public Health Service).

However, a major limiting factor in widespread industrial applications of these volatile compounds, particularly 1,8-cineole, pertains to its biological source. Currently, this monoterpenoid is produced solely by plants restricted to certain species of *Eucalyptus*, but also including *Rosmarinus officinalis* (Rosemary), and *Thymus valgaris* (Thyme) (Thomas, et al., 2000, Chemical Industry Digest (Special Millennium Issue) pp. 104-108), *Melaleuca teretifolia* (Southwell, et al., 2003, Journal of Essential Oil Research 15:339-341), and *Mentha spicata* (Cook, et al., 2007, The Journal of Essential Oil Research 19:225-230). A novel and more bountiful source for these compounds could significantly advance their industrial application profiles.

Endophytes, microorganisms that reside in the tissues of living plants (Stone et al., Microbial Endophytes, Ed. C. W. Bacon and J. F. White Marcel Decker, Inc, NY, 2000), are relatively unstudied and potential sources of novel natural products for exploitation in medicine, agriculture and industry. It is worthy to note, that of the nearly 300,000 plant species that exist on the earth, each individual plant is host to one or more endophytes. Only a handful of these plants have ever been completely studied relative to their endophytic biology. Consequently, the opportunity to find new and interesting endophytic microorganisms among myriads of plants in different settings, and ecosystems is great. Currently, endophytes are viewed as an outstanding source of bioactive natural products because there are so many of them occupying literally millions of unique biological niches (higher plants) growing in so many unusual environments.

It is well accepted that microorganisms can be a production source of chemical compounds, enzymes and other complexes that have industrial utility. The prospect that endophytes produce novel bioactive products stems from the idea that some endophytes may have coevolved with their respective higher plant, and as a result may produce certain phytochemicals characteristic of their hosts (Strobel and Daisy, 2003, Microbiology and Molecular Biology Reviews 67:491-502; Tan and Zou, 2001, Nat. Prod. Rep. 18:448-459). The enormous diversity generated by the presence of microbial life forms is amplified by their ability to inhabit novel niches, ranging from deep ocean sediments to the earth's thermal pools. Endophytic fungi inhabit one such biological niche and are characterized by their ability to asymptomatically colonize living plant tissues. There are untold numbers of potential novel fungal genera, of which endophytes constitute a significant proportion (Smith, et al., 2008, PloS 1 3(8): e3052). Ecosystems exhibiting the greatest plant diversity also seemingly exhibit the greatest abundance and diversity of microbial endophytes. Ultimately, biological diversity implies chemical diversity as constant chemical innovation is required in such highly competitive ecosystems. Thus, the search for novel endophytic microbes is ongoing, with activity of their natural products encompassing their use as antibiotics, antiviral compounds, anticancer agents, antioxidants, insecticides, antidiabetic agents, and immunosuppressive compounds (Strobel and Daisy, 2003, Microbiology and Molecular Biology Reviews 67:491-502).

One such endophyte is *Hypoxylon* spp., which is a fungal endophyte of *Persea indica*, an evergreen tree native to the Canary Islands, where it grows not in abundance but is found on several islands including Tenerife in the Laurisilva. *Persea* spp. are also native to Central and South America and were later introduced into Southern California (Zentmyer, et al., 1990, California Avocado Society 1990 Yearbook 74:239-242).

Undoubtedly, production of 1,8-cineole, among other volatile organic compounds such as 1-methyl-1,4-cyclohexadiene and (+)-α-methylene-α-fenchocamphorone by a fungal source, would have significant implications for use of such compounds in widespread industrial applications. Therefore, a need exists for the identification and production of volatile organic compounds produced by fungi. The present invention satisfies this need.

SUMMARY OF THE INVENTION

The present invention relates to a method for producing at least one compound selected from the group consisting of 1,8-cineole and 1-methyl-1,4-cyclohexadiene. The method includes the step of culturing a microorganism on or within a culturing media in a container under conditions sufficient for producing the at least one compound. In one embodiment, the microorganism is an endophyte. In another embodiment, the endophyte is a fungus. In another embodiment, the fungus has the imperfect stage of *Nodulisporium*. In another embodiment, the fungus is from the genus *Nodulisporium*. In another embodiment, the fungus is from the genus *Hypoxylon*. In another embodiment, the fungus is from the genus *Annulohypoxylon*. In another embodiment, the fungus is from the genus *Daldinia*. In another embodiment, the fungus is from the genus *Xylaria*. In another embodiment, the microorganism is serially propagated. In another embodiment, the microorganism is grown on or in a high-starch substrate. In another embodiment, the microorganism is grown in a liquid medium. In another embodiment, the microorganism is grown on a solid medium. In another embodiment, the method further includes the step of isolating the at least one compound from the culturing media. In another embodiment, the method further includes the step of isolating the at least one compound from a vapor produced within the container.

The present invention also relates to a method for producing an alcohol. The method includes the step of culturing a fungus having the imperfect stage of *Nodulisporium* on or within a culturing media in a container under conditions sufficient for producing the alcohol, In one embodiment, the alcohol is ethanol. In another embodiment, the fungus is serially propagated. In another embodiment, the fungus is grown on or in a high-starch substrate. In another embodiment, the fungus is grown in a liquid medium. In another embodiment, the fungus is grown on a solid medium.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising

FIG. 9A is an illustration of *Populus* sp. FIG. 9B is an illustration of *Platanus* sp. FIG. 9C is an illustration of *Acer* sp. These specimens are known from late Cretaceous shales of the Western USA (the bars 1.5 cm). FIG. 9D is a photograph of petrified fungal hyphae penetrating petrified wood samples recovered from the oil rich Melstone, Mt. area. FIG. 9E is a photograph of petrified fungal hyphae penetrating petrified wood samples recovered from the oil rich Melstone, Mt. area.

FIG. 11A is a photograph illustrating how the leaves and shale materials are completely covered with fungal hyphae. FIG. 11B is a photograph illustrating how the "Trap Shale" itself (when the stainless steel mesh screen was removed) was damp and covered with fungal hyphae. Actual width of the main chamber is 30 cm, FIG. 11C is a photograph of an SEM image of fungal hyphae growing on the surface of a shale particle (treatment shale). FIG. 11D is a photograph of a SEM image illustrating no evidence of any hyphae on the control shale.

FIGS. 12A-12B, is a series of photographs representing the morphological characteristics of Ni25-2A, FIG. 12A is a photograph of *Thelypteris angustifolia* or Broad Leaf Maiden Fern as the host of the endophytic fungus *Nodulisporium* sp. (Ni25-2A). The bar equals 1 cm. FIG. 12B is a SEM image of the conidiophore of *Nodulisporium* sp. showing a clump of singly borne conidiophores. The bar equals 2 nm.

FIGS. 13A-13B, is an illustration of the phylogenetic analysis of Ni25-2A. FIG. 13A is a graph showing how the evolutionary history of Ni25-2A (*Nodulisporium* sp.) was inferred using the UPGMA method (Tamura et al., 2007, Molec. Biol. Evol. 24:1596-1599). The optimal tree with the sum of branch length=0.15647555. The percentage of replicate trees in which the associated taxa clustered together in the bootstrap test (500 replicates) are shown next to the branches. The tree is drawn to scale, with branch lengths in the same units as those of the evolutionary distances used to infer the phylogenetic tree. The evolutionary distances were computed using the Maximum Composite Likelihood method and are in the units of the number of base substitutions per site. All positions containing gaps and missing data were eliminated from the dataset (complete deletion option). There were a total of 408 positions in the final dataset. FIG. 12B is a table of the distance matrix depicting the percent sequence identity and divergence of the 18S-ITS-5.8S ribosomal gene sequence of NI25-2A with its close relatives, constructed by the MegAlign module of the DNASTAR (Lasergene) software.

DETAILED DESCRIPTION

Figure 1:
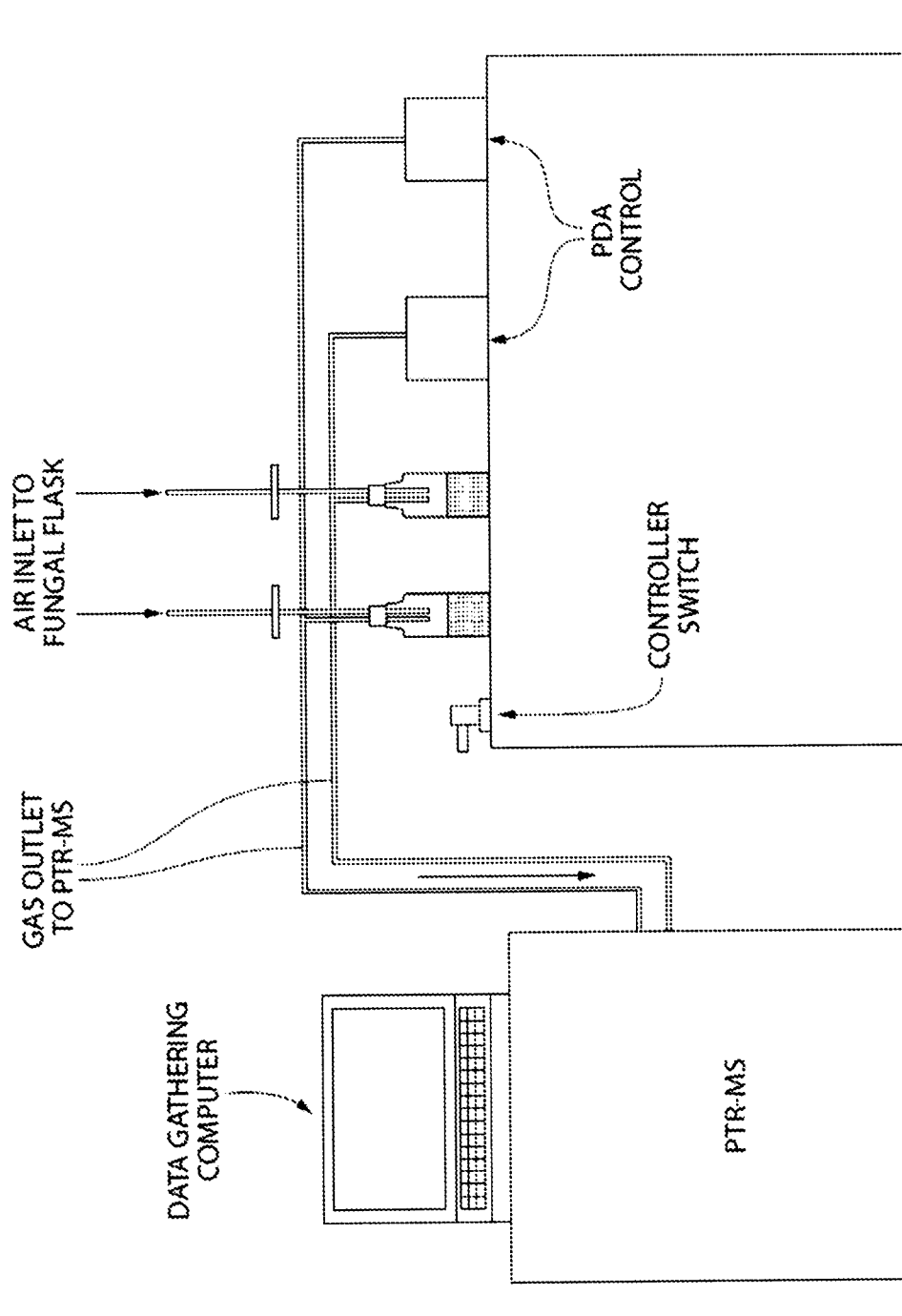
FIG. 1 depicts a PTR-mass spectrometer used to monitor VOC production by *Hypoxylon* sp. The *Hypoxylon* sp. culture produced 100.5 mg dry weight of surface mycelium covering the 121.6 cm$^2$ agar slant at 7 days. Monitoring began 2.5 days after the fungus was inoculated onto the agar surface. The inset shows the details of the hardware used to regulate gas flow into the culture flask. The controller switch continuously changes input of gases from the control bottle (only PDA) to the fungal culture. The computer screen shows the contiuous output of individual ions found in the gas phase.
Figure 2A:
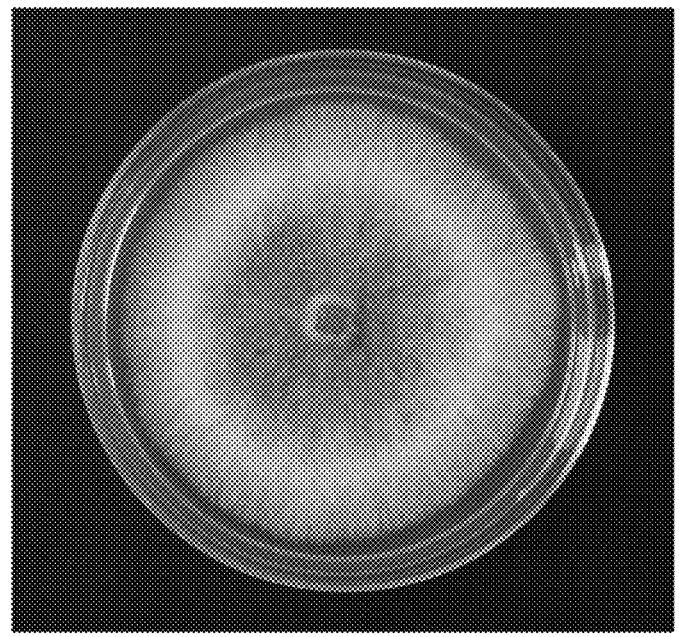
FIGS. 2A and 2B, depicts a 10-day old culture of *Hypoxylon* sp. grown on PDA from both the top side (2A) and bottom side (2B). The darker aspect of the photos represents varying degrees of a greenish-tan coloration.
Figure 2B:
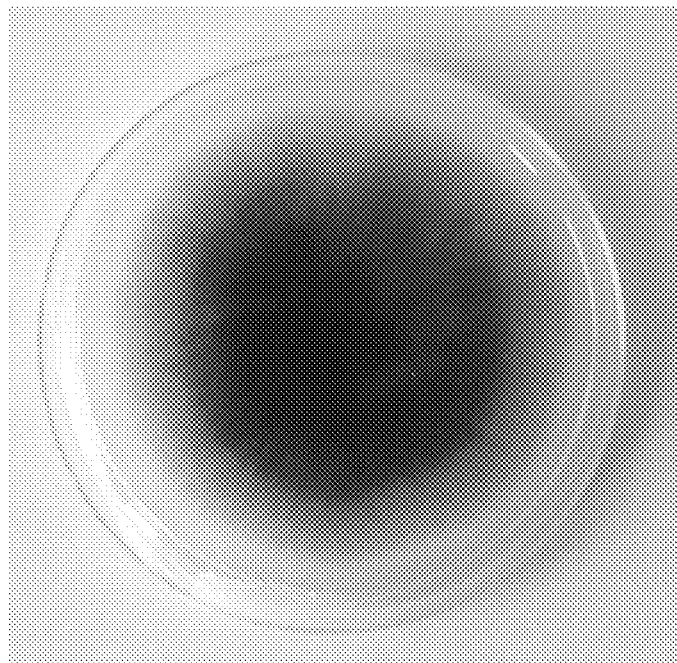
Figure 3:
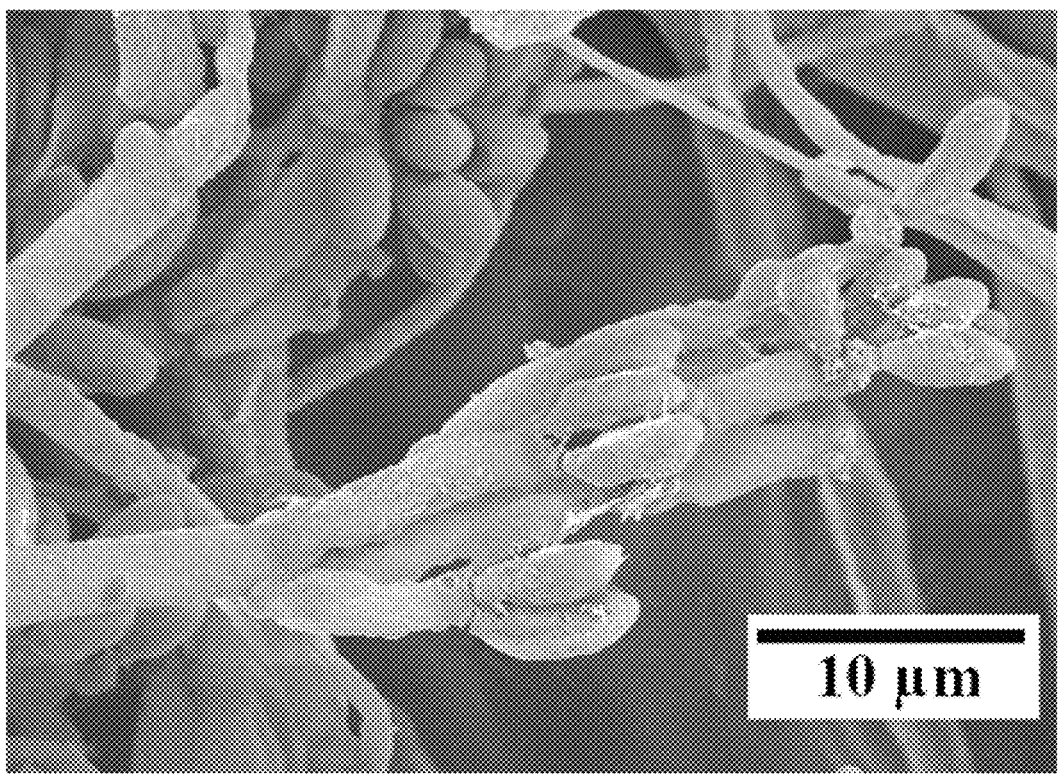
FIG. 3 is an SEM image of a branched conidiophore *Nodulisporium* sp. (CI-4) depicting conidia and scars from the budding verticles of the conidiophore.
Figure 4:
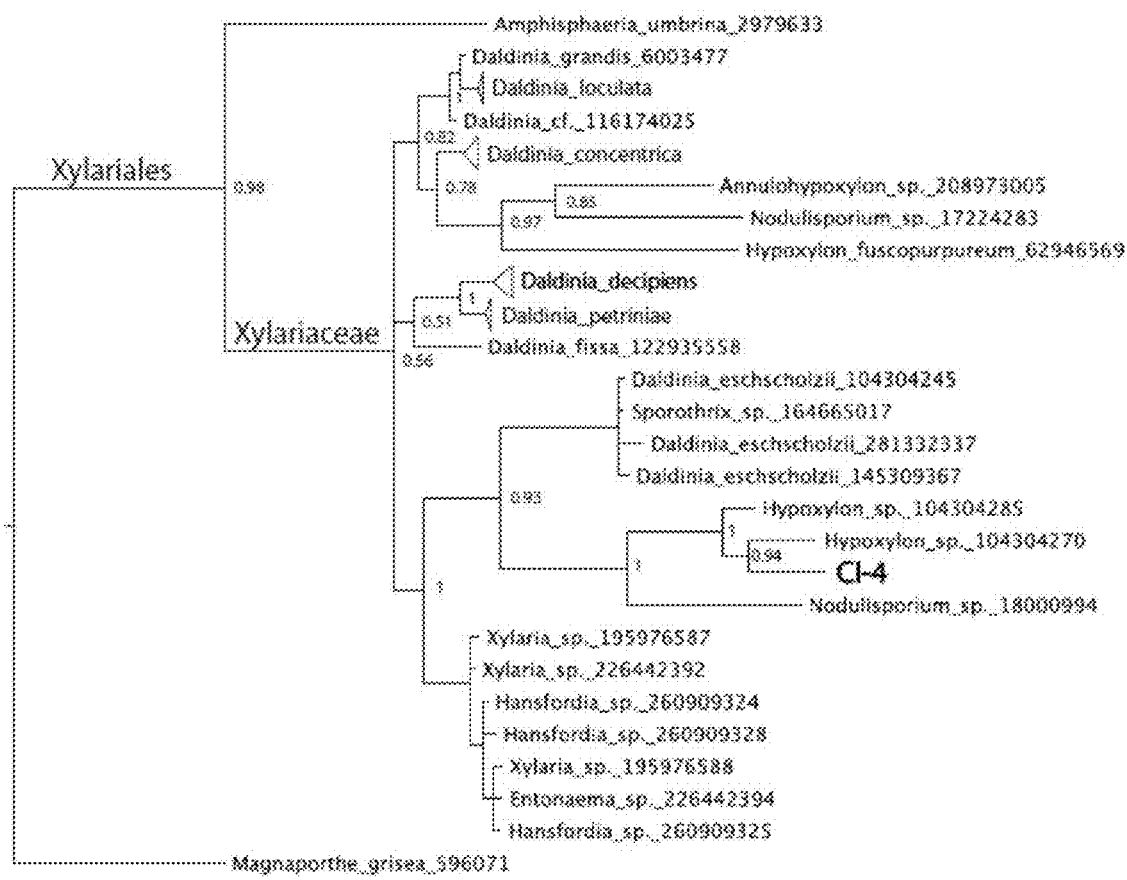
FIG. 4 is chart demonstrating the evolutionary relationships of *Hypoxylon* sp. (CI-4) with 20 other close taxons (BLAST based). The evolutionary history was inferred using the Neighbor-Joining method (Saitou and Nei, 1987, Molecular Biology and Evolution 4:406-425). The optimal tree with the sum of branch length=0.83699359 is shown. All positions containing gaps and missing data were eliminated from the dataset (complete deletion option). There were a total of 307 positions in the final dataset. Phylogenetic analyses were conducted in MEGA4 (Tamura, et al., 2007, Molecular Biology and Evolution 24:1596-1599).

The present invention relates to isolated fungal lines capable of producing an impressive spectrum of volatile organic compounds (VOCs), most notably 1,8-cineole, 1-methyl-1,4-cyclohexadiene, and (+)-α-methylene-α-fenchocamphorone, among many others (see Table 3, below). The present invention also relates to methods of producing such VOCs from microorganisms, and collecting or recovering the produced VOCs for commercial and/or industrial use. In some embodiments, the microorganism is a fungus.

The present invention is based on the discovery that selected fungi, including numerous *Hypoxylon* spp., produce an impressive spectrum of VOCs, most notably 1,8-cineole, 1-methyl-1,4-cyclohexadiene, and (+)-α-methylene-α-fenchocamphorone. Media containing starch and/or sugar related substrates best supports VOC production by fungus. Direct on-line quantification of VOCs was measured by proton transfer mass spectrometry (PTR-MS) covering a continuous range, with optimum VOC production occurring at 6 days at 145 ppmv with a rate of production of 7.65 ppmv/hr. This demonstrated that 1,8-cineole (a monoterpene) is produced by a microorganism, which represents a novel and important source of this compound. 1,8-cineole is an octane derivative and has potential use as a fuel additive, as do the other VOCs of this organism, listed in Table 3, below. Thus, fungal sourcing of this compound and other VOCs as produced by *Hypoxylon* sp. and other fungi described herein greatly expands their potential applications in medicine, industry, and energy production.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "hydrocarbon" generally refers to a chemical compound that consists of the elements carbon (C) and hydrogen (H). All hydrocarbons consist of a carbon backbone and atoms of hydrogen attached to that backbone. Hydrocarbons are of prime economic importance because they encompass the constituents of the major fossil fuels (coal, petroleum, natural gas, etc.) and biofuels, as well as plastics, waxes, solvents and oils.

The term "fungus" or "fungi" includes a wide variety of nucleated, spore-bearing organisms that are devoid of chlorophyll. Examples of fungi include yeasts, molds, mildews, rusts, and mushrooms.

The term "bacteria" includes any prokaryotic organism that does not have a distinct nucleus.

The term "isolated" means altered or removed from the natural state or biological niche through the actions of a human being.

The term "antibiotic" includes any substance that is able to kill or inhibit a microorganism. Antibiotics may be produced by a microorganism or by a synthetic process or semisynthetic process. The term, therefore, includes a substance that inhibits or kills fungi for example, cycloheximide or nystatin.

The term "culturing" refers to the propagation of organisms on or in solid or liquid media of various kinds.

The term "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the target infection or disease states.

The term "metabolite" or "volatile" refers to any compound, substance or byproduct of a fermentation of a microorganism that has a biological activity.

The term "mutant" refers to a variant of the parental strain as well as methods for obtaining a mutant or variant in which the desired biological activity is similar to that expressed by the parental strain. The "parent strain" is defined herein as the original fungus (e.g. *Hypoxylon*) strains before mutagenesis. Mutants occur in nature without the intervention of man.

They also are obtainable by treatment with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

The term "variant" refers to a strain having all the identifying characteristics of the strains of fungus and can be identified as having a genome that hybridizes under conditions of high stringency to the genome of the organism. A variant may also be defined as a strain having a genomic sequence that is greater than 85%, more preferably greater than 90% or more preferably greater than 95% sequence identity to the genome of the organism. A polynucleotide or polynucleotide region (or a polypeptide or polypeptide region) has a certain percentage (for example, 80%, 85%, 90%, or 95%) of "sequence identity" to another sequence, which means that, when aligned, that percentage of bases (or amino acids) are the same in comparing the two sequences. This alignment and the percent homology or sequence identity can be determined using publicly available software programs known in the art.

The term "instructional material," as that term is used herein, includes a publication, a recording, a diagram, or any other medium of expression which can be used to communicate the usefulness or procedural steps of the invention in the kit for growing the fungi under optimal conditions for optimal VOC production.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Further, all numerical designations, e.g., pH1, temperature, time, concentration, and molecular weight, including ranges, are approximations which may be varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are well known in the art.

Fungi Suitable for Production of VOCs

A search for endophytes hosted by the evergreen tree *Persea indica* revealed the presence of a fungal sp. having the imperfect stage of *Nodulisporium*, as described herein. An examination of this organism revealed that it produces important VOCs including, without limitation, 1,8-cineole; 1-methyl-1,4-cyclohexadiene, and (+)-α-methylene-α-fenchocamphorone (see Table 3, below). These compounds have potential industrial utility, such as fuels or additives as per the VOCs of some other endophytic fungi now known as Mycodiesel™ (Strobel, et al., 2008, Microbiology 154:3319-3328).

In one aspect, the present invention includes an isolated fungus capable of producing at least one VOC. For example, the following fungal isolates having the imperfect stage of *Nodulisporium*, each being capable of producing at least one VOC, were deposited under the terms of the Budapest Treaty with the ARS Culture Collection (NRRL), 1815 North University Street, Peoria, Ill. 61604-3999 USA, on May 11, 2011 and assigned the corresponding Accession Numbers:

| Fungal sp. | NRRL Accession Number |
|---|---|
| Co27-5 | 50500 |
| Cl-4a | 50501 |
| Ti-13 | 50502 |
| Ec-38 | 50503 |

These strains have been deposited under conditions that assure that access to these cultures are readily available to one determined by the Commissioner of Patents and Trademarks to be entitled thereto under 37 C.F.R. §1.14 and 35 U.S.C. §122, and are available as required by foreign patent laws in countries wherein counterparts of the subject application, or its progeny are filed. However, it should be understood that the availability of a deposit does not constitute a license to practice the subject invention in derogation of patent rights granted by governmental action. Based on these deposits, the entire genomes of isolates Co27-5, CI-4A, Ti-13, Ec-38 or Ni-25 2A are hereby incorporated into and included in this filing.

Figure 5:
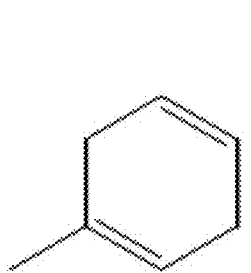
FIG. 5 is a structural depiction of the fungal volatile organic compounds I-methyl-1,4-cyclohexadiene (top left), 1,8-cineole (top right), and (+)-α-methylene-α-fenchocamphorone (bottom).
Figure 5:
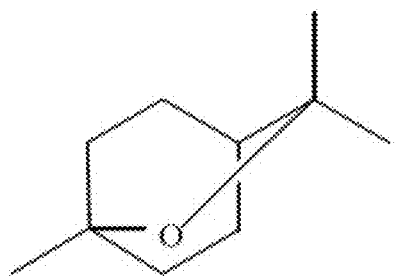
Figure 5:
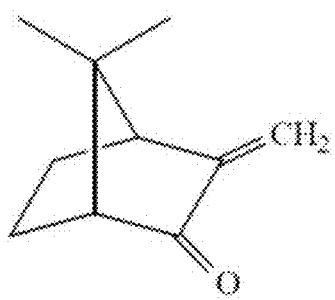

The present invention provides methods of producing VOCs from microorganisms, and collecting or recovering the produced VOCs for commercial and/or industrial use. In one embodiment of the present invention, any one of the fungi described herein can produce an impressive spectrum of volatile organic compounds (see Tables 3, 6, 10-11, and 15-17, below) including, without limitation, 1,8-cineole, 1-methyl-1,4-cyclohexadiene, (+)-α-methylene-fenchocamphorone, the structures of which are depicted in FIG. 5. It should be appreciated that the present invention is not limited to production of the aforementioned VOCs by *Hypoxylon* or any other fungus having the imperfect stage of *Nodulisporium*. Rather, the present invention includes production of VOCs, particularly 1,8-cineole, 1-methyl-1,4-cyclohexadiene, and (+)-α-methylene-α-fenchocamphorone by any fungus, or for that matter, any microorganism. For example, 1,8-cineole can also be produced by an isolated *Nodulisporium* sp., such as PC-37-24, and is therefore also contemplated as forming part of the present invention. In another example, the present invention relates to endophytic fungi that produce volatile organic compounds, such as hydrocarbons, from isolates of *Nodulisporium* spp, *Hypoxylon* spp., *Daldinia* spp., *Xylaria* spp., and *Annulohypoxylon* spp. These compounds produced by the fungus can then be used in a variety of commercial industries, including medicine, energy production, and fuel additives or constituents. This novel, renewable source of hydrocarbons is desirable because it provides a supplement to the existing limited resources of non-renewable hydrocarbons.

Furthermore, it should be appreciated that the disclosed *Hypoxylon* isolates can also be classified as an endophytic *Nodulisporium* sp. or *Daldinia* sp. or *Annulohypoxylon* sp., depending on the fungal identification methodology used. Generally speaking, almost all fungi have a perfect (sexual stage) and an imperfect stage (non sexual), and each is given a name. For example, *Nodulisporium*-like organisms can have the perfect stage of *Hypoxylon, Daldinia, Annulohypoxylon,* or *Xylaria*. Therefore, as contemplated herein, fungi identified as any one of *Nodulisporium* spp., *Hypoxylon* spp., *Daldinia* spp., *Xylaria* spp., or *Annulohypoxylon* spp. form part of the present invention for the generation of VOCs, as described herein. As an example of this, while strains Co27-5, CI-4A, Ti-13, Ec-38, Ni25-2A, Th-9, and Fl-9 are generally classified as *Hypoxylon*, they each have the imperfect stage of *Nodulisporium* sp. By way of another example, while strain EC-12 is generally classified as *Daldinia*, it has the imperfect stage of *Nodulisporium* sp. By way of yet another example, while strain D-6 is generally classified as *Annulohypoxylon*, it has the imperfect stage of *Nodulisporium* sp. Further, the fingi of the present invention include all anamorphs and teleomorphs, to the extent such forms exist and are available. For example, the *Hypoxylon* strains Co27-5, CI-4A, Ti-13, Ec-38, Ni25-2A, Th-9, and Fl-9 have *Nodulisporium* sp. as their anamorphic stage. The difference between an anamorph and teleomorph is that one is the asexual state and the other is the sexual state, where the two states exhibit different morphology under certain conditions. In cases where fungi reproduce both sexually and asexually, these fungi may have two names. For example, the teleomorph name describes the fungus when reproducing sexually, while the anamorph name refers to the fungus when reproducing asexually. Also, the holomorph name refers to the "whole fungus", encompassing both reproduction methods. When referring to any one of these names as describing a fungus, all such fungal stages or forms are contemplated and included in the present invention, regardless of whether a different or alternative name may exist. Thus, it should be appreciated that for the aforementioned *Nodulisporium* spp., *Hypoxylon* spp., *Daldinia* spp., *Xylaria* spp., *Annulohypoxylon* spp., and synonyms thereof, the present invention encompasses both the perfect and imperfect ("anamorph") states, and other taxonomic equivalents, e.g., teleomorphs, regardless of the species name by which they are called. Those skilled in the art will readily recognize the identity of appropriate equivalents.

As will be appreciated by one of skill in the art, microorganisms such as *Nodulisporium* spp., *Hypoxylon* spp., *Daldinia* spp., *Xylaria* spp., *Annulohypoxylon* spp., can be used in combination with other microbes (e.g. yeasts or other bacteria) for the large scale production of befouls.

As contemplated herein, the present invention also includes isolated strains of a *Nodulisporium, Hypoxylon, Daldinia, Xylaria,* or *Annulohypoxylon*, wherein the isolated fungal strain was serially propagated. When strains are serially propagated, some of the characteristics of the strain may change. Such changes include deletion or suppression of metabolic pathways, an increase in certain metabolic pathways, changes to the chromosome, genes and/or operons (e.g. via mutations or changes in the regulatory factors that control the expression level of said genes or operons). For example, a strain of *Hypoxylon* may have changes in its metabolic characteristic and/or genetic make-up as compared to *Hypoxylon* isolates Co27-5, CI-4A, Ti-13, Ec-38, Ni-25 2A, Th-9, or Fl-9. Such changes to the metabolic characteristics and/or genetic make-up may increase and/or decrease the production of the specific compounds listed in Table 3. Methods for isolating mutant cells with a desired characteristic are well known in the art. See, for example, U.S. Pat. No. 5,348,872, which is herein incorporated by reference in its entirety.

The present invention also provides a method for producing volatile organic compounds, such as hydrocarbons. In one embodiment, the method comprises culturing isolates of *Nodulisporium* spp, *Hypoxylon* spp., *Daldinia* spp., *Xylaria* spp., *Annulohypoxylon* spp., and under conditions sufficient for producing VOCs, and collecting or recovering the produced VOCs. The methods of the present invention also include any combination of procedures and steps used in the culturing of fungi and recovery of at least one VOC, as described hereinthroughout.

Volatile Organic Compounds Produced by Fungi

As stated previously, the present invention relates to endophytic fungi that produce volatile organic compounds, such as the hydrocarbons listed in Tables 3, 6, 10-11, and 15-17, below. Of particular interest is the production of 1,8-cineole, 1-methyl-1,4-cyclohexadiene, and (+)-α-methylene-α-fenchocamphorone, the structures of which are depicted in FIG. 5. Each of these compounds is either itself a monoterpene or is a direct derivative of a monoterpenic compound. Given that monoterpenes are prime constituents of essential plant oils, production of such compounds by an endophytic fungus may lie in support of the idea that as these fungi coevolved with their respective higher plant hosts there was a gene transfer resulting in the production of characteristic host phytochemicals (Strobel and Daisy, 2003, Microbiology and Molecular Biology Reviews 67:491-502). Whether or not this is consistent for this particular endophyte, 1,8-cineole is not known to be a constituent of essential oils collected from leaves of a *Persea indica* plant in California (Weyerstahl, et al., 1993, Flavour and Fragrance Journal 8:201-207). However, this possibility should not be disregarded, given the highly diverse environment of this isolate. The ability of *Hypoxylon* sp. to synthesize monoterpenic compounds typically associated with antimicrobial activity exemplifies the ability for microorganisms to inhabit essential oil producing plants, and their potential role in acquiring the biosynthetic pathways of these compounds should not be overlooked (Table 2).

1,8 Cineole has a broad spectrum of uses, from over-the-counter medical ointment to solvent/degreasers to flavoring/fragrances to alternative fuel. Thus, production of 1,8-cineole by a fungal isolate is significant and greatly expands its potential for a broad spectrum of industrial applications. For example, previous studies have shown prevention of phase separation when 1,8-cineole is used as an additive in ethanol-gasoline fuel blends (Barton and Tjandra, 1989, Fuel 68:11-17), and alternative fuels comprised of a gasoline/eucalyptus oil mixture, with 1,8-cineole as the major fuel component, resulted in an improved octane number and reduced carbon monoxide exhaust (Sugito, K., & Takeda, S. (1981). U.S. Pat. No. 4,297,109).

In certain embodiments, the VOCs may be hydrocarbons, and may be useful for the production of biofuels, plastics, plasticizers, antibiotics, rubber, fuel additives, and/or adhesives. As will be appreciated by one of skill in the art, hydrocarbons can also be used for electrical power generation and heating. The chemical, petrochemical, plastics and rubber industries are also dependent upon hydrocarbons as raw materials for their products. As used herein, the term "biofuel" refers generally to any fuel that derives from biomass, i.e. recently living organisms or their metabolic byproducts, such as manure from cows, or a hydrocarbon produced by fungi. A biofuel may be further defined as a fuel derived from a metabolic product of a living organism.

While the production of other monoterpenes like citronellol, geraniol, linalool, nerol, and α-terpinol by microorganisms such as *Ceratocystis* spp., *Trametes odorata, Phellinus* spp., and *Kluyveromyces lactis* (Kempler, G. M. (1983). Production of Flavor Compounds by Microorganisms. III. Terpenenes. B. Production of Monoterpenes by Microorganisms. In Advances in *Applied Microbiology*, Vol 29, pp. 35-37. Edited by A. I. Laskin. New York, N.Y.: Academic Press, Inc.) has been demonstrated, the present invention represents the first time that 1,8-cineole and the other volatile products listed in Table 3 can be produced by endophytic fungi. Prior to this, the only known biological source of 1,8-cineole was from plant tissue. Production of VOCs from fungi represents a far superior commercial production model than from plants.

Biosynthesis of 1,8-cineole involves its conversion from geranyl pyrophosphate by 1,8-cineole cyclase (cineole synthase), whose activity is inhibited by cysteine- and histidine-directed reagents but protected by substrate-metal ion complexes, with the ether oxygen atom of this oxygen-containing terpene being solely derived from water (Croteau, et al., 1994, Arch-Biochem-Biophys 309:184-192). In comparison, fenchocamphorone is also converted from geranyl pyrophosphate and proceeds through the pathway as the intermediate (−)-(3R)-linalyl pyrophosphate via (−)-endo-fenchol cyclase (synthase) which subsequently cyclizes in the presence of the (4R)-α-terpinyl and (1R,5R)-pinyl cations to form (−)-endo-Fenchol which can further oxidize to α/β-fenchocamphorone (Croteau, et al., 1988, Journal of Biological Chemistry 263: 15449-15453). An understanding of these individual pathways and their derivation from a common pathway involving production of geranyl pyrophosphate from mevalonate (MVA pathway) agrees with the idea that *Hypoxylon* sp. may be conditioned for biosynthesis of monoterpenes and subsequent manipulation of these pathways could lead to their optimum production on a mass commercial scale.

Figure 6:
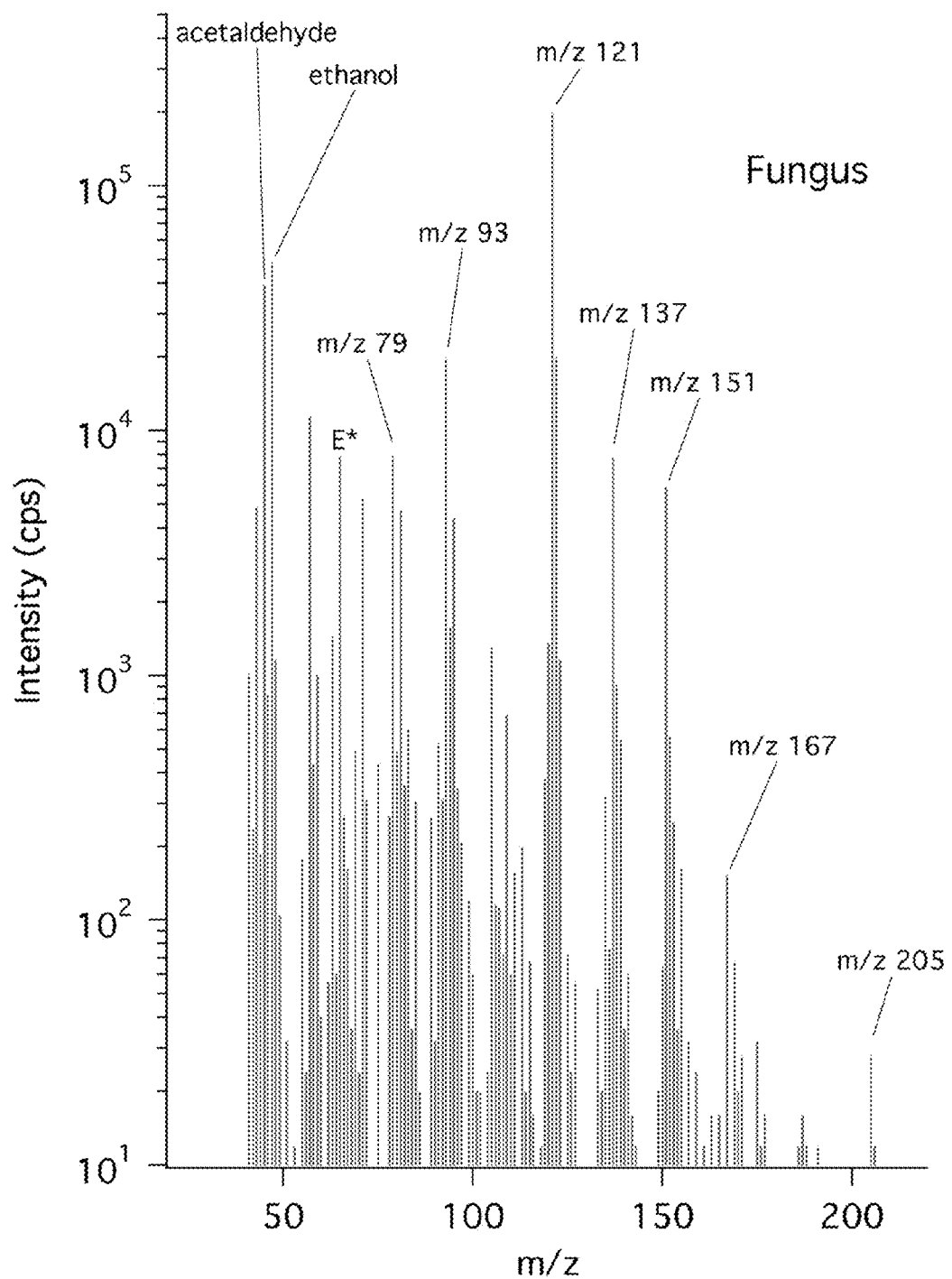
FIG. 6 is a PTR mass spectrum of the head space of a 5-day old culture of *Hypoxylon* sp.
Figure 7:
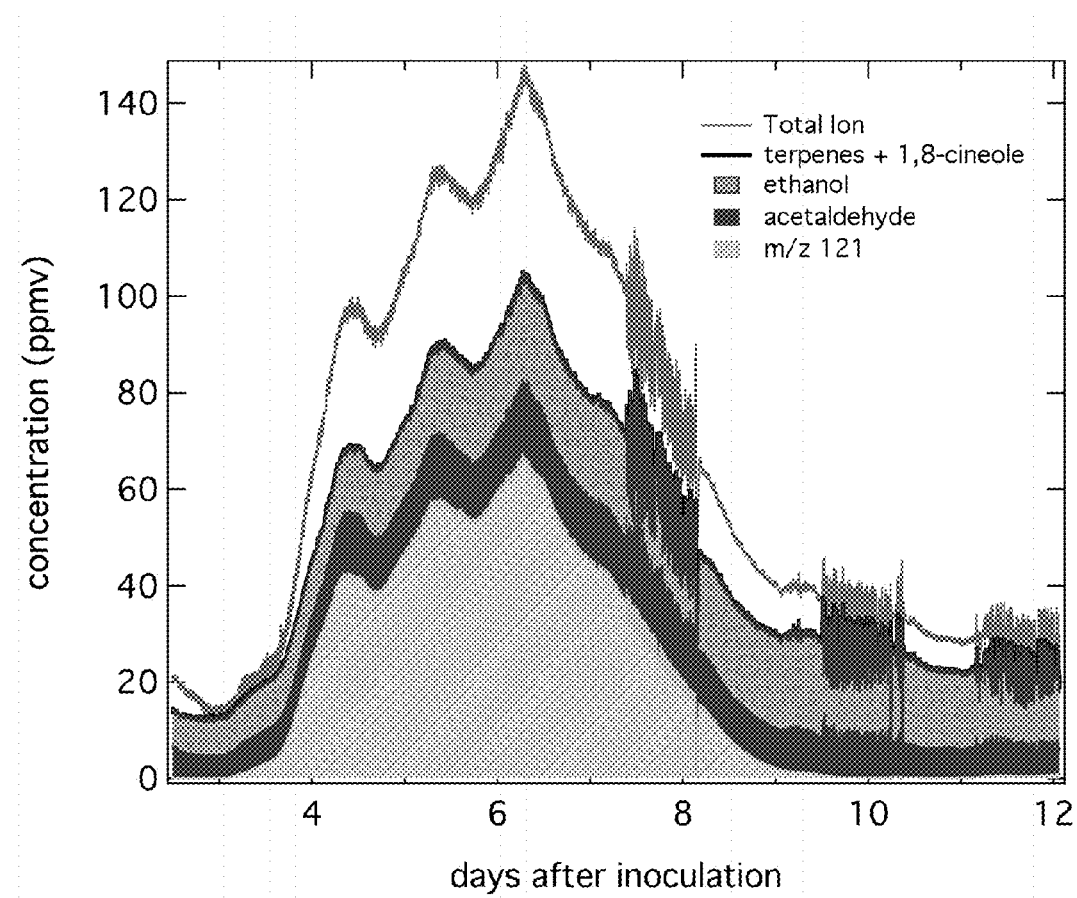
FIG. 7 is a graph of the production of individual compounds in the VOCs of *Hypoxylon* sp. as a function of time as measured and calculated from PTR mass spectral data. The m/z at 121 is likely the series of protonated cyclic alkanes/alkenes whose mass is 120 (See Table 3 herein). The terpenes including 1,8 cineole were calculated from contributions of compounds yielding masses 81, 137 and 155. All calculations are minus the PDA background control flask.

Other examples of volatile organic compounds which may be produced by any microorganism of the present invention are alcohols, such as ethanol. Ethanol is an important compound for the fuel industry, as it is a component of biofuel and can be used as an additive in gasoline. As depicted in FIGS. 6 and 7, ethanol was identified as a VOC isolated from the headspace of a microorganism of the present invention. Ethanol may be produced and isolated using any method described hereinthroughout.

Growth Substrates and Culturing of Fungi for Production of VOCs

It should be appreciated that any substrate suitable for promoting fungal growth may be used in the production of VOCs, including without limitation any of the components listed in Table 4, in any ratios and combinations, as would be understood by those skilled in the art. As contemplated herein, high starch substrates promote optimal VOC production, as demonstrated by substrate utilization assays containing high amounts of starch as a carbohydrate source (Table 4). In certain embodiments, cellulose may also be a suitable substrate. Given the enormous volumes of accumulating cellulitic biomass and the utilization of foodstuff grains in alcohol (fuel) production, microorganisms that utilize cellulose for the production of VOCs are quite attractive.

For example, in some embodiments, the culture media for culturing fungi may include substrates comprising oatmeal, barley, or potato agar bases. The culture media may also be a PDA medium, a cellulose medium, and may include starch, glucose, or any combination of components listed in Table 4. Further, the selected fungal strain may be grown in a medium containing any combination of inorganic salts, organic nitrogen sources, such as peptones, defatted cotton seed flour, corn steep liquor, or yeast extract and carbon source. Examples of carbon source may include, but is not limited to, glucose, lactose, sucrose, cellulose or other carbohydrates. Further still, it should be appreciated that the present invention should not be limited by the type or amount of growth media used, and should include use of any media suitable for cultivating fungi as would be understood by those skilled in the art. In other embodiments, these conditions can also include culturing fungi in the absence of oxygen (anaerobic conditions) or in reduced oxygen conditions (e.g., microaerophilic conditions).

Generally speaking, the isolated fungi of the present invention can be cultured using standard methods as would be understood by those skilled in the art. Alternatively the fungal cultures can be cultured on a large scale for commercial use, by using conventional fermentation techniques. In this context fermentation is used broadly to refer to any controlled fungal culturing conditions. Prior to large scale growth an inoculum of said growth culture is generally cultured. In certain embodiments, the fungi can be cultured in a bioreactor vessel for a scaled up production of VOCs. Any conventional bioreactor vessel can be used as the vessel for the purpose of this invention. For example, the vessel may be made of materials such as stainless steel, glass, plastic, and/or ceramics, and may have a volume of from about 100 ml to 10,000 L or larger. The bioreactor vessel may be connected to a series of storage flasks that contain nutrient solutions and solutions for maintaining and controlling various parameters of the cultivation and VOC recovery process. Depending on the particular needs of the fermentation, there may be separate storage flasks for individual supply of substrates to the vessel, which substrates serve as the carbon, nitrogen or mineral source for the living cells in the vessel.

Further, several methods can be used to grow the various fungal isolates for use in the invention. Fed Batch culture is a variation on ordinary batch culture and involves the addition of a nutrient feed to the batch. Cells are cultured in a medium in a fixed volume. Before the maximum cell concentration is reached, specific supplementary nutrients are added to the culture. The volume of the feed is minimal compared to the volume of the culture. Fed batch culture typically proceeds in a substantially fixed volume, for a fixed duration, and with a single harvest either when the cells have died or at an earlier, predetermined point.

In a continuous culture, the cells are initially grown in a fixed volume of medium. To avoid the onset of the decline phase, fresh medium is pumped into the bioreactor before maximum cell concentration is reached. The spent media, containing a proportion of the cells, is continuously removed from the bioreactor to maintain a constant volume. The process also removes the desired product, which can be continuously harvested, and provides a continuous supply of nutrients, which allows the cells to be maintained in an exponentially growing state. Theoretically, the process can be operated indefinitely. Continuous culture is characterized by a continuous increase in culture volume, an increase and dilution of the desired product, and continuous maintenance of an exponentially growing culture.

Perfusion culture is similar to continuous culture except that, when the medium is pumped out of the reactor, cells are not removed. As with a continuous culture, perfusion culture is an increasing-volume system with continuous harvest that theoretically can continue indefinitely.

Recovery of VOCs

Once produced by the selected fungi isolate, several methods can be used to isolate the VOCs listed in Table 3 from the culture media or from vapor in a growth chamber. For example, common separation techniques can be used to remove the cells from the broth or agar, and common isolation procedures, such as (without limitation) extraction, distillation, and carbocolumn trap procedures, can be used to obtain VOCs from the cell-free broth or agar. See, for example, U.S. Pat. Nos. 4,275,234, 5,510,526; 5,641,406, and 5,831,122, and International Patent Application Number WO 93/00440, each of which is hereby incorporated by reference in its entirety.

Fractional distillation and/or absorption chromatography are also non-limiting examples of methods to extract the desired product produced by fungal isolates of the present invention. Fractional distillation is the separation of a mixture into its component parts, or fractions, such as in separating chemical compounds by their boiling point by heating them to a temperature at which several fractions of the compound will evaporate. Absorption chromatography is a physical separation method in which the components of a mixture are separated by differences in their distribution between two phases, one of which is stationary (stationary phase) while the other (the mobile phase) moves through it in a definite direction. The substances must interact with the stationary phase to be retained and separated by it.

Gas chromatography is a well known technique for fractionating and determining the relative amounts of various components in a sample containing a mixture of compounds of differing volatilities. For example, the sample is vaporized and the entire resulting quantity of gases is passed through an analytical chromatography column. Chromatographic processes such as gas chromatography can rapidly determine the volatiles content of a multicomponent sample, such as would be produced by the fungal isolates of the present invention.

In some instances, Pressure Swing Adsorption (PSA) may be used to separate some gas species from a mixture of gases under pressure according to the species' molecular characteristics and affinity for an adsorbent material. It operates at near-ambient temperatures and so differs from cryogenic distillation techniques of gas separation. Special adsorptive materials (e.g., zeolites) are used as a molecular sieve, preferentially adsorbing the target gas species at high pressure. The process then swings to low pressure to desorb the adsorbent material.

As contemplated herein, a carbotrap column may be used for the trapping and recovery of VOCs. Generally, VOCs produced by a fungal culture pass through a trapping column containing adsorption material, and are trapped within the column as they are captured by the adsorption material. The VOCs may then be released from the trapping column by simultaneously heating the column while purging with a gas, and collecting the VOCs in a cold trap condenser. A detailed description can be found in U.S. patent application Ser. No. 13/591,968, which is hereby incorporated by reference in its entirety.

Mutant and/or Engineered Fungi for Enhanced Production of VOCs

The present invention also includes mutant or engineered fungi that ultimately increase the production yield of at least one VOC, or the speed at which the mutant or engineered fungi can produce at least one VOC. Mutant or engineered fungi are obtainable by treatment of fungi with or by a variety of methods and compositions understood by those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means.

For example, as contemplated herein, the present invention also includes identifying and cloning genes that encode for production of at least one VOC from the genomes of each fungus described herein. In one embodiment, the *Hypoxylon* genome is probed for the gene or genes (e.g. an operon) that encode the synthetic pathways that produce a VOC from Table 3, such as 1,8-cineole, 1-methyl-1,4-cyclohexadiene, and (+)-α-methylene-α-fenchocamphorone. Thus, the present invention encompasses an isolated nucleic acid molecule from fungi encoding a polypeptide involved in the synthesis or production of at least one VOC. In another embodiment, an isolated nucleic acid molecule is at least 65%, at least 70%, at least 75%, at least 80%, at least 85%, at least 90%, at least 95%, at least 96%, at least 97%, at least 98%, or at least 99% identical to said isolated nucleic acid molecule from any one of the fungi isolates described herein. In another embodiment, a polypeptide sequence is at least 65%, at least 70%, at least 75% at least 80%, at least 85%, at least 90%, at least 95%, at 6%, at least at least 97%, at least 98%, or at least 99% identical to a polypeptide from any one of the fungi isolates described herein.

Methods to clone and/or probe genomes for synthetic pathways may include creating cDNA and/or genomic libraries, and screening the libraries for genes that produce the VOC synthetic pathways. Thus, the present invention comprises a DNA and/or chromosomal library of any one of the fungi isolates described herein. In one embodiment, the library is cloned into a vector that can replicate in a prokaryotic cell and/or eukaryotic cell. In another embodiment, the eukaryotic cell is a fungal cell. In another embodiment, the library is a lambda phage, Yeast Artificial Chromosome, Bacterial Artificial Chromosome, and/or cDNA. In another embodiment, the library is screened for production of VOCs from Table 3, such as 1,8-cineole, 1-methyl-1,4-cyclohexadiene, and (+)-α-methylene-α-fenchocamphorone.

Another method for determining the gene, genes and/or operon(s) that encode for the production of VOCs include mutagenizing the genome of any one of the fungi described herein and looking for an increase, addition, reduction or removal of a specific VOC. This can be accomplished via chemical and/or transposon mutagenesis. Once a gene, genes and/or operon(s) is identified, said gene, genes or operon(s) can be cloned and/or isolated. Thus, one embodiment of the invention comprises an isolated nucleic acid of any one of the fungi described herein, wherein the nucleic acid molecule is cloned into a vector. In another embodiment, said nucleic acid molecule encodes for a gene, genes, or operon(s) that encode for proteins involved in the production of VOCs of Table 3. In another embodiment, the vector autonomously replicates or integrates into the host's chromosome. In another embodiment, said vector is transformed or transfected into a heterologous cell. In another embodiment, said heterologous cell is selected from the group consisting of a prokaryotic or eukaryotic cell.

The present invention also encompasses variants and fragments of polynucleotides and/or proteins of any one of the fungi described herein that produce or are part of the pathway(s) that produce VOCs. The variants may contain alterations in the nucleotide and/or amino acid sequences of the constituent proteins. The term "variant" with respect to a polypeptide refers to an amino acid sequence that is altered by one or more amino acids with respect to a reference sequence.

The variant can have "conservative" changes, or "nonconservative" changes, e.g., analogous minor variations can also include amino acid deletions or insertions, or both. In addition, the nucleotides can be sequenced to ensure that the correct coding regions were cloned and do not contain any unwanted mutations.

Nucleic acid molecules encoding one or more biosynthetic enzyme or protein, and orthologs and homologs of these sequences, may be incorporated into transformation or expression vectors of any one of the fungi described herein. As used herein, the term "vector" refers generally to a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Once the gene(s) and/or operon(s) of any one of the fungi described herein have been identified, cloned, transformed, transfected or infected into a heterologous organism (or new organism from a synthetic genome), the heterologous organism can be grown to produce and purify the desired VOCs, including those listed in Table 3.

Thus, the present invention also includes a method for generating mutant strains of a fungus with an increased production rate or production amount of at least one compound, such as 1,8-cineole, 1-methyl-1,4-cyclohexadiene, and (+)-α-methylene-α-fenchocamphorone, or any other compound listed in Table 3, below. The method includes the steps of mutating spores of the fungus, culturing the mutated spores, and screening the cultures of mutated spores for enhanced production rate or production amount of at least one compound selected from the group consisting of 1,8-cineole, 1-methyl-1,4-cyclohexadiene, and (+)-α-methylene-α-fenchocamphorone.

Kits

The present invention also provides for a kit comprising one or more containers filled with one or more of the ingredients of the compositions of the invention. The present invention provides kits that can be used in any of the methods described herein. In one embodiment, a kit comprises at least one *Nodulisporium* sp., *Hypoxylon* sp., *Daldinia* sp., *Xylaria* sp., *Annulohypoxylon* sp., or in one or more containers. The organism can be supplied frozen in media, freeze dried and/or as spores. The kit may also include instructional material for growing the fungi under optimal conditions for optimal VOC production. The methods in the instructions may include specific bioreactor volumes, purification schemes, optimal temperature, pH, and/or other conditions. The kit may also include the growth media. The media contained in the containers of these kits may be present as a ready-to-use formulation, or as a more concentrated formulation. In addition, the media can be supplied in dry powder. Thus, a kit can comprise a dry power of the media of the invention and a liquid to suspend the media. The liquid may be water or buffers known in the art. Filters for sterilization of the media may also be provided.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding ription and the following illustrative examples, make and utilize the present invention and practice the claimed methods. The following working examples therefore, specifically point out the preferred embodiments of the present invention, and are not to be construed as limiting in any way any portion of the disclosure.

Example 1

*Hypoxylon* Sp, an Endophyte of *Persea indica*, Producing 1,8-Cineole and Other Bioactive Volatiles with Fuel Potential Fungal Isolation and Storage Endophytic fungal culture, CI-4A, was obtained as an endophyte from an evergreen tree (*Persea indica*), native to the Canary Islands. One small limb was excised from *Persea indica* found growing on the island of Tenerife, Spain, at N-28° 32' 21"; W-160 16' 16". Other plant species sampled from this same island included *Acacia* sp., *Pinus canariensis*, *Prunus lusitanica* and *Rhamnus glandifolia*, none of which fostered recovery of CI-4. Isolation procedures followed a previously described protocol (Worapong, et al., 2001, *Cinnamomun zeylanicum*. Mycotaxon 79:67-79; Ezra, et al., 2004, Microbiology 150:4023-4031). Briefly, external tissues were thoroughly exposed to 70% ethanol prior to excision of internal tissues which were cultured on standard Petri dishes of water agar and glycerol arginine medium (GAM). Endophytic fungi growing from the plant tissues were then picked and re-cultured on potato dextrose agar (PDA). It is also notable that CI-4A grows readily in the presence of the VOCs of *M. albus*, which should facilate its ready isolation from other plant sources (Strobel, et al., 2001, Microbiology 147:2943-2950). The fungus was stored by placing small plugs of PDA supporting mycelial growth in 15% glycerol at −70° C. An alternative storage method was also utilized in which the fungus colonized sterile barley seed, which was subsequently air dried and then stored at −70° C.

Scanning Electron Microscopy

Scanning electron microscopy (SEM) was performed on sterile carnation leaves colonized with CI-4, according to the following protocol outlined by Ezra (Ezra, et al., 2004, Microbiology 150:4023-4031). The fungus was grown on PDA, or gamma irradiated carnation leaves for several weeks and then was processed for SEM. The samples were slowly dehydrated in ethanol and then critically point dried, coated with gold and examined with an FEI XL30 scanning electron microscope (SEM) FEG with high vacuum mode using an Everhart-Thornley detector.

Fungal DNA Isolation and Acquisition of ITS-5.8S rDNA Phylogenetics

The fungus was grown on PD broth for 7 days, after which the mycelium was harvested and the genomic DNA extracted using DNeasy Plant and Fungi Mini Kit (Qiagen), according to the manufacturer's directions. The internal transcribed spacer (ITS) regions of the fungus were amplified using PCR with the universal ITS primers ITS1 (5' TCC GTA GGT GAA CCT GCG G 3') (SEQ ID NO:1) and ITS4 (5' TCC TCC GCT TAT TGA TAT GC 3') (SEQ ID NO:2). All other procedures were carried out as previously described by Ezra. The DNA was sequenced and submitted to GenBank. Sequences obtained in this study were compared to the GenBank database using the BLAST software. A phylogenetic tree was assembled using MEGA4 (Tamura, et al., 2007, Molecular Biology and Evolution 24:1596-1599) and the Neighbor-Joining method (Saitou and Nei, 1987, Molecular Biology and Evolution 4:406-425) with positions containing gaps and missing data eliminated from the dataset (complete deletion option).

Bioassay Tests for *Hypoxylon* sp. VOCs Against Pathogens

The VOCs produced by CI-4A were tested for inhibitory antimicrobial activity against selected pathogenic fungi and bacteria according to a bioassay test system previously described for analysis of VOCs produced by *Muscodor albus* (Strobel, et al., 2001, Microbiology 147:2943-2950). Optimum production of volatile bioactive compounds was determined by exposing test organisms to cultures of varying ages. Inhibitory activities of the VOCs produced by CI-4A after 3-7 days were compared and maximum inhibition observed would suggest the highest concentration of bioactive VOCs. Subsequent bioassay tests were conducted on a wider range of test organisms at the appropriate point at which CI-4A produced maximal amounts of bioactive VOCs.

The assays were conducted by removing a 2.5 cm wide strip of agar from the mid-portion of a standard Petri plate of PDA, creating two isolated halves of agar. The fungus (CI-4) was inoculated onto one half-moon agar piece and incubated at 23° (C for six days to allow for optimum production of volatile compounds. Test pathogens were inoculated onto the half-moon section of agar opposite the half-moon section inoculated with CI-4. The plate was then wrapped with a single piece of Parafilm and incubated at 23° (C for 24 hours. Growth of yeast and bacteria was then qualitatively assessed based on microbial density of a streak inoculum, while growth of filamentous fungi was quantitatively assessed based on multiple measurements of growth extending from the edge of the inoculum plugs comparable to corresponding controls as described by Strobel (Strobel, et al., 2001, Microbiology 147:2943-2950). Ultimately, viability of each test pathogen for which growth was not observed was evaluated after three days of exposure to CI-4A VOCs by transfer of the original exposed inoculum plug or streak onto a fresh plate of PDA. Viability was then determined via observation of growth within three days (Strobel, et al., 2001, Microbiology 147:2943-2950). All tests were conducted in triplicate.

Media Selection for Preferred Substrate Utilization Assay for VOC Production

A variety of selected media was used to determine a combination of substrates that best facilitated VOC production by CI-4. A single plug taken from an actively growing culture of CI-4A on PDA was used to inoculate each agar based medium. Preliminary quantification of 1,8 cineole was estimated by a human olfactory method since this compound is readily sensed by smell. Independent ratings given on a 7 day old cultures grown at 22° C., that had been sealed with parafilm, by seven different observers on two separate occasions. The rating system was 1 (low to none) up to 5 (maximum production). The evaluations were averaged and the standard deviations calculated.

The amount of fungal mycelial growth was assessed by scraping it directly from the surface of the agar surface, drying, and weighing. The following media were tested: (A) yeast extract 0.1 g $l^{-1}$ plus salts; (B) peptone 0.1 g $l^{-1}$ plus salts; (C) cellulose 25 g $l^{-1}$ plus salts and yeast extract 0.1 g $l^{-1}$; (D) cellulose 25 g $l^{-1}$ plus salts and peptone 0.1 g $l^{-1}$; (E) starch 25 g $l^{-1}$ plus salts and yeast extract 0.1 g $l^{-1}$; (F) starch 25 g $l^{-1}$ plus salts and peptone 0.1 g $l^{-1}$; (G) glucose 25 g $l^{-1}$ plus salts and yeast extract 0.1 g $l^{-1}$; (H) glucose 25 g $l^{-1}$ plus salts and peptone 0.1 g $l^{-1}$; (I) cellobiose 25 g $l^{-1}$ plus salts and yeast extract 0.1 g $l^{-1}$; (J) cellobiose 25 g $l^{-1}$ plus salts and peptone 0.1 g $l^{-1}$; (K) glycerol 25 ml $l^{-1}$ plus salts and yeast extract 0.1 g $l^{-1}$; (L) glycerol 25 ml $l^{-1}$ plus salts and peptone 0.1 g $l^{-1}$; (M) instant mashed potatoes 25 g $l^{-1}$ plus salts and yeast extract 0.1 g $l^{-1}$ (MP); (N) potato dextrose (Difco) (PDA); and (O) oatmeal agar (Difco). The salts and agar concentration used in each medium followed the recipe of the M1-D medium previously outlined by Pinkerton & Strobel (Pinkerton and Strobel, 1976, Proc Natl Acad Sci USA 73:4007-4011). Each assay was performed in duplicate and the data were analysed to obtain mean mass/rate values and standard deviations.

Qualitative Analyses of CI-4A Volatiles

Analysis of gases in the air space above cultures of CI-4A grown for eight days at 23° C. on PDA were conducted according to the following protocol as described by Strobel (Strobel, et al., 2001, Microbiology 147:2943-2950). First, a baked "Solid Phase Micro Extraction" syringe (Supelco) consisting of 50/30 divinylbenzene/carboxen on polydimethylsiloxane on a Stable Flex fibre was placed through a small hole drilled in the side of the Petri plated and exposed to the vapour phase for only 5 min due to the high concentration of fungal VOCs. The syringe was then inserted into the splitless injection port of a Hewlett Packard 6890 gas chromatograph containing a 30 m×0.25 mm I.D. ZB Wax capillary column with a film thickness of 0.50 µm. The column was temperature programmed as follows: 30° C. for 2 min increased to 220° C. at 5° C. min$^{-1}$. The carrier gas was ultra high purity helium, and the initial column head pressure was 50 kPa. Prior to trapping the volatiles, the fiber was conditioned at 240° C. for 20 min under a flow of helium gas. A 30 sec injection time was used to introduce the sample fiber into the CC. The gas chromatograph was interfaced to a Hewlett Packard 5973 mass selective detector (mass spectrometer) operating at unit resolution. The MS was scanned at a rate of 2.5 scans per second over a mass range of 35-360 amu. Data acquisition and data processing were performed on the Hewlett Packard ChemStation software system. Tentative identification of the compounds produced by CI-4A was made via library comparison using the NIST database, and all chemical compounds described in this report use the NIST data base chemical terminology. Final confirmatory identification was made for any compounds with available authentic standards obtained from Sigma/Aldrich by comparing the GC/MS data of the standards, including 1-8-cineole and 1-methyl-1,4-cyclohexadiene, with GC/MS data of fungal products. The GC/MS tests were conducted several times under different exposure times of the fibre to fungal gases with the 5 min. exposure being the optimum given the large volume of VOCs being made by the fungus.

Quantification of Fungal Volatiles

PTR-MS was used to quantify production of fungal volatiles on a continuous monitoring basis beginning with a 2.5 day old culture growing on a 300 ml slant of PDA in a 1 L bottle at 20±2° C. The bottle possessed an O-ring sealed cap that had been modified to possess both inlet and outlet tubes with 10 std cc/min of purified compressed air (Ezra, et al., 2004, Plant Science 166:1471-1477) (FIG. 1). Monitoring of all ions in produced in the spectrum was done for 7.5 days and the concentration of VOCs was estimated (Ezra, et al., 2004, Plant Science 166:1471-1477; Bunge, et al., 2008, Appl Environ Microbiol 74: 2179-2186; Strobel, et al., 2008, Microbiology 154:3319-3328). Air-space analysis of the cultured and uninoculated samples was done by passing a small flow of air (medical-grade compressed air) through the culture bottles and then diluted with air of the same quality (FIG. 1). The sample lines were constructed entirely from PFA Teflon tubing and fittings. A 1/20-1/10 dilution kept the measurements within the linear dynamic range of the instrument and prevented water from condensing in the sample lines. Mass spectral scans were acquired from 20 to 220 Da.

It is to be recognized that the PTR-MS instrument ionizes organic molecules in the gas phase through their reaction with 1-$H_3O^+$, forming mostly protonated molecules ($MH^+$, where M is the neutral organic molecule) which can then be detected by a standard quadrupole mass spectrometer. This process can be run on real air samples with or without dilution, since the primary constituents of air (nitrogen, oxygen, argon and carbon dioxide) have a proton affinity less than water and thus are not ionized. Most organic molecules (excepting alkanes) have a proton affinity greater than water and are therefore ionized and detected. A further advantage of PTR-MS is that from the known or calculated quantities, the reaction time, the amount of $H_3O^+$ present, and the theoretical reaction rate constant for the proton transfer reaction, the absolute concentration of constituents in a sample can be quantified (Lindinger, et al., 1998, Int J Mass Spectrom Ion Process 173:191-241). Finally, an enormous advantage of PTR-MS is that it can be run in real time and continuously produce data on the concentrations of specific ions of interest.

Concentrations derived from the PTR-MS measurements were calculated using equations derived from reaction kinetics and assume that a reaction rate coefficient to $2 \times 10^{-9}$ ml s$^{-1}$ is appropriate for all compounds (Lindinger, et al., 1998, Int J Mass Spectrom Ion Process 173:191-241; Ezra, et al., 2004, Plant Science 166:1471-1477). This method provides a simple means by which the measured ion intensity at any mass can be expressed as an equivalent concentration. In the event that a particular ion can be ascribed to a single compound, then the concentration of that specific compound can be determined using the same procedure as above followed by correction for dilution and any product ion fragmentation. The product ion distribution is determined from mixtures prepared from pure standards.

Biological Activities of the VOCs of *Hypoxylon* sp.

The degree of susceptibility of the assay test organisms was dependent upon the age of the *Hypoxylon* sp. culture to which they were exposed for 24 hr (Table 1).

bioactive substances, occurred at six days with eight of the ten test organisms exhibiting maximum inhibition at this time point. The most sensitive test organisms to the VOCs of *Hypoxylon* sp. were *Phytophthora* spp., *Sclerotinia sclerotiorum, Aspergillus fumigatus*, and *Cercospora beticola* (Table 1).

An expanded bioassay test involving 16 plant associated fungi revealed varying degrees of response when evaluated via a bioassay Petri plate test system (Strobel, et al., 2001, Microbiology 147:2943-2950). The organisms showed minimal to complete inhibition with a three day exposure to fungal VOCs from a six day old culture of *Hypoxylon* sp., while there was no inhibition of various yeasts and bacteria (Table 2).

TABLE 2

Effects of the VOCs of a 6 day old culture of *Hypoxylon* sp. on various fungi. Inhibition values were calculated as a percentage of growth inhibition as compared to an untreated control test organism at a 3 day exposure. Tests were conducted in triplicate and results varied as indicated by standard deviations. All organisms were viable after exposure to fungal VOCs.

| Test Organism | Percent Inhibition | D or A |
| --- | --- | --- |
| *Sclerotinia sclerotiorum** | 90.4% ± 16.5 | A |
| *Fusarium solani* | 63.0% ± 5.6 | A |
| *Mycosphaerella fijiensis* | 50.0% ± 57.7 | A |
| *Pythium ultimum** | 78.2% ± 14.3 | A |
| *Verticillium dahliae* | 80.0% ± 34.6 | A |
| *Aspergillus fumigatus** | 43.0% ± 16.8 | A |
| *Phytophthora palmivora** | 70.0% ± 38.3 | A |
| *Ceratocystis ulmi* | 42.8% ± 32.0 | A |
| *Botrytis cinerea* | 100.0% ± 0.0 | A |
| *Colletotrichum lagenarium* | 36.1% ± 12.7 | A |
| *Geotrichium candidum** | 27.0% ± 6.7 | A |
| *Rhizoctonia solani** | 66.6% ± 57.7 | A |
| *Phytophthora cinnamomi** | 100.0% ± 0.0 | A |
| *Trichoderma viridae** | 50.0% ± 4.7 | A |
| *Cercospora*beticola* | 100.0% 0.0 | A |
| *Muscodor albus* | 58.3% ± 11.7 | A |

*Denotes organism was also used in the progressive bioassay test system.
D = Dead and A = Alive All organisms, including those exhibiting complete inhibition in the presence of fungal VOCs were viable upon re-culturing

TABLE 1

Progressive (time course) bioassay showing susceptibility of selected fungal pathogens to *Hypoxylon* sp. VOCs as a function of *Hypoxylon* sp. culture age with a 24 hr exposure to the fungal VOCs. The percentages reported are relative to growth of the test organism on a PDA plate minus *Hypoxylon* sp.

| Test Organism | 3 days | 4 days | 5 days | 6 days | 7 days |
| --- | --- | --- | --- | --- | --- |
| *Phytophthora palmivora* | −16.6% ± 7.8 | 11.1% ± 0.0 | 88.8% ± 0.0 | 100.0% ± 0.0 | 100.0% ± 0.0 |
| *Geotrichium candidum* | 12.5% ± 0.0 | 6.2% ± 8.8 | 25.0% ± 0.0 | 31.2% ± 8.8 | 25.0% ± 17.6 |
| *Rhizoctonia solani* | 75.0% ± 35.3 | 75.0% ± 35.3 | 37.5% ± 53.0 | 87.5% ± 17.6 | 100.0% ± 0.0 |
| *Sclerotinia sclerotiorum* | 28.5% ± 0.0 | 67.8% ± 15.1 | 100.0% ± 0.0 | 100.0% ± 0.0 | 100.0% ± 0.0 |
| *Aspergillus fumigatus* | 10.0% ± 14.1 | 40.0% ± 0.0 | 50.0% ± 14.1 | 100.0% ± 0.0 | 75.0% ± 35.3 |
| *Pythium ultimum* | −3.4% ± 4.9 | 43.0% ± 14.8 | 58.1% ± 6.5 | 97.6% ± 3.2 | 100.0% ± 0.0 |
| *Fusarium solani* | 31.2% ± 0.0 | 15.6% ± 4.4 | 31.2% ± 8.8 | 56.2% ± 17.6 | 43.7% ± 8.8 |
| *Phytophthora cinnamomi* | 6.2% ± 44.1 | 50.0% ± 35.3 | 75.0% ± 0.0 | 100.0% ± 0.0 | 100.0% ± 0.0 |
| *Trichoderma viridae* | 16.6% ± 16.8 | 4.7% ± 6.7 | 19.0% ± 6.73 | 23.8% ± 0.0 | 4.7% ± 0.0 |
| *Cercospora beticola* | 41.6% ± 11.7 | 50.0% ± 0.0 | 75.0% ± 35.36 | 100.0% ± 0.0 | 100.0% ± 0.0 |

A progressive (time course) assay using ten different fungal pathogens was designed to determine the time point at which maximum sensitivity of the test organisms occurred which may also relate to the maximum point of VOC production by the fungus. Inhibitory activity of VOCs produced after three, four, five, six, and seven days was compared and maximum inhibition, suggesting the highest concentration of volatile on PDA. The most sensitive fungi were *Phytophthora* spp., *Cercospora beticola, Sclerotinia sclerotiorum*, and *Botrytis cinerea* (Table 2).

Composition of Volatiles Produced by *Hypoxylon* sp.

Several GC/MS analyses were conducted on the VOCs produced by an eight day old culture of *Hypoxylon* sp. Controls consisting of uninoculated PDA Petri plates were used to subtract compounds contributed by the medium. Preliminary identification of fungal VOCs was determined by comparison of unknown volatiles with MS data of reference compounds listed in the NIST database. It is to be noted that the bulk of the VOCs could not be conclusively identified. However, for those VOCs which could be identified, authentic standards were used to confirm the identification of possible compounds and included 1,8-cineole and 1-methyl-1,4-cyclohexadiene. In addition, other compounds were tentatively identified on the basis of the % quality of the match to the NIST data base with an arbitrary cut off at 60% quality match. The most abundant compound, as based upon total integrated peak areas of the GC elution profile, was tentatively identified as (+)-α-methylene-α-fenchocamphorone, a monoterpene (Table 3) (FIG. 5).

the GC/MS analysis including cyclohexane, 1,2,4-tris(methylene)-(or isomer), and 8-anti-methylbicyclo(3.2.1)octa-2,6-diene (or isomer) which are probably the chief contributors in the PTR mass spectrum of the 121 peak (M plus H+) (Table 3) (FIG. 6). Other unidentified compounds, many in lesser amounts, were also seen in the VOCs of this fungus on each GC/MS analysis (Table 3). It is to be noted that the results of the GC/MS are at times inconsistent with the PTR-MS and this is due to the fact that the SPME fiber lacks universal adsorption efficiency and likewise the PTR-MS lacks the ability to discern protonated molecular species from other ion fragments. One of the notable discrepancies is the total lack, on repeated analyses, of the SPME fibre to trap the high amounts of ethanol and acetaldehyde that are present in the VOC mix as detected by PTR-MS (Table 3, FIGS. 6, 7). On

TABLE 3

A GC/MS air-space analysis of the volatile compounds produced by *Hypoxylon* sp. after eight days incubation at 23° C. on PDA using a SPME fiber. Compounds present in a control PDA Petri plate have been subtracted from the data. Unknown compounds represent those with a quality % value less than 60.

| Retention Time (min) | Relative Area | Possible Compound | Mol. Mass (Da) | Quality |
|---|---|---|---|---|
| 4.53 | 7.3 | *1,4-Cyclohexadiene, 1-methyl- | 94 | 91 |
| 9.01 | 7.6 | *1,8-Cineole | 154 | 96 |
| 13.99 | 58.1 | Cyclohexane, 1,2,4-tris(methylene)- (or isomer) | 120 | 83 |
| 14.22 | 4.6 | 8-anti-methylbicyclo(3.2.1)octa-2,6-diene (or isomer) | 120 | 83 |
| 14.28 | 2.0 | 8-anti-methylbicyclo(3.2.1)octa-2,6-diene (or isomer) | 120 | 87 |
| 14.33 | 3.4 | 1,2,4-Tris(methylene)-cyclohexane (or isomer) | 120 | 81 |
| 21.89 | 1.4 | 6-Aza-1,2,3,3a-tetrahydropyrrolo[1,2-a]quinoxalin-4 | 189 | 83 |
| 23.13 | 2.5 | Unknown | 136 | |
| 25.21 | 5.9 | Unknown | 114 | |
| 26.11 | 2.3 | 5-ethyl-4,4,5-trimethyl-2-cyclopenten-1-one | 152 | 62 |
| 27.67 | 10.9 | Unknown | 110 | |
| 29.6 | 206.7 | ?(+)-α-methylene-α-fenchocamphorone | 150 | 62 |
| 29.71 | 111.5 | 7-Oxatetracyclo[4.1.0.0(2,4).0(3,5)]heptane | 94 | 76 |
| 29.76 | 35.5 | Unknown | 94 | |
| 29.79 | 47.8 | Unknown | 92 | |
| 29.95 | 9.5 | Unknown | 108 | |
| 30.2 | 5.5 | Unknown | 144 | |
| 30.35 | 4.0 | Unknown | 150 | |
| 30.42 | 4.4 | Unknown | 66 | |
| 30.55 | 7.2 | Unknown | 138 | |
| 30.7 | 1.3 | Unknown | 103 | |
| 30.72 | 2.5 | Unknown | 150 | |
| 30.77 | 1.9 | 1H-inden-1-one, 2,3,3a,4,7,7a-hexahydro-7a-methyl-, | 150 | 68 |
| 30.88 | 2.6 | 2,4,6-Trimethyl-1,3-benzenediamine | 150 | 72 |
| 30.97 | 3.6 | Unknown | 150 | |
| 31.07 | 4.9 | Unknown | 150 | |
| 31.3 | 55.3 | ?(+)-α-methylene-α-fenchocamphorone | 150 | 78 |
| 31.43 | 1.9 | Unknown | 150 | |
| 32.53 | 1.5 | Unknown | 236 | |

*Denotes that the retention time and MS spectrum closely matched or were identical to an authentic standard compound. Those compounds without a designated footnote have a mass spectrum that most closely matched the appropriate compound in the NIST database. The unknowns had a Quality ranking of less than 60%.
?Denotes that a question remain as to the actual identity of the compound listed, the correct elution time of the actual product remains uncertain-the peaks could represent isomers of (+)-α-methylene-α-fenchocamphorone.

However, at least two peaks appeared designated as this monoterpenoid and these have tentatively been assigned as isomers or relatives of fenchocamphorone since an authentic standard for this compound was not available. A second monoterpene detected in smaller quantities was identified as 1,8-cineole by its NIST data base match, its similarity to the authentic compound, the appearance of peaks at 81, 137, and 155 in the PTR mass spectrum (identical to its authentic standard), and its characteristic *eucalyptus* odor all of which are consistent with 1,8-cineole (Table 3; FIGS. 5, 6). The fungus also produced a third compound often considered a derivative of the monoterpene group, 1-methyl-1,4-cyclohexadiene (FIGS. 5, 6). Many other compounds appeared in the other hand, there are many examples in which the data sets of the two MS techniques are compatible, i.e. data for the compound with a MW of 120 and the 1,8 cineole spectra (Table 3 and FIG. 6).

The production of two, possibly three or more monoterpenes/monoterpene derivatives may suggest that the endophyte possesses the enzymatic machinery specialized for the biosynthesis of monoterpenic compounds that are usually associated with higher plants. Monoterpenes are naturally formed products generally associated as common constituents of essential oils and often contribute to antimicrobial activity (Madyastha, 1984, Journal of Chemical Sciences 93:677-686). Biosynthetic pathways leading to the production of such monoterpenes by *Hypoxylon* sp. may suggest possible insight as to its ability to grow in the presence of a highly biologically active fungus, *M. albus*. The comprehensive spectrum of antimicrobial activity exhibited by *M. albus* is yet to be matched by a VOC producing fungus (Strobel, et al., 2001, Microbiology 147:2943-2950). The ability to withstand its own monoterpenic antimicrobials may or may not be linked to its ability to withstand the potent volatile antimicrobials produced by *M. albus*.

Substrate Facilitation of VOC Production on Selected Media.

There were higher concentrations, in general, of volatile compounds, as detected by an olfactory method when *Hypoxylon* sp. was grown on media enriched with yeast extract over peptone as a source for amino acids (exception seen only in combination with starch). Media containing starch, glucose, and cellobiose as a source of carbohydrates, including PDA, oatmeal agar, and MP, also facilitated higher concentrations of detectable volatile compounds by olfactory methods.

Olfactory qualitative analyses were supported by quantitative measures of surface mycelial mat dry weight on each media type. Surface mycelial mass calculations were conducted following the qualitative analyses and yielded similar substrate preferences. While mass calculations seemed to be dependent first on amino acid sources and second on carbohydrate sources, olfactory ratings seemed to be most dependent on carbohydrate sources.

The analyses were both run in duplicate and standard deviations were calculated (Table 4).

TABLE 4

Substrate facilitation of volatile production on different media showing qualitative olfactory observations based on independent ratings 1 to 5 (5 being optimum), and the dry weight of the surface mycelial mat.

| Media | Surface Mass (mg) | Olfactory Rating |
|---|---|---|
| (A.) Yeast | 2.5 ± 0.7 | 1.1 ± 0.4 |
| (B.) Peptone | 1.0 ± 0.0 | 1.3 ± 0.7 |
| (C.) Yeast + Cellulose | 1.5 ± 0.7 | 1.1 ± 0.4 |
| (D.) Peptone + Cellulose | 1.0 ± 0.0 | 1.0 ± 0.0 |
| (E.) Yeast + Starch | 26.5 ± 6.4 | 4.1 ± 1.3 |
| (F.) Peptone + Starch | 30.5 ± 3.5 | 4.1 ± 1.1 |
| (G.) Yeast + Glucose | 22.5 ± 0.7 | 4.0 ± 1.1 |
| (H.) Peptone + Glucose | 11.0 ± 4.2 | 3.4 ± 0.7 |
| (I.) Yeast + Cellobiose | 19.0 ± 1.4 | 3.1 ± 1.2 |
| (J.) Peptone + Cellobiose | 7.5 ± 0.7 | 2.8 ± 0.7 |
| (K.) Yeast + Glycerol | 3.5 ± 0.7 | 2.1 ± 1.2 |
| (L.) Peptone + Glycerol | 1.0 ± 0.0 | 1.5 ± 0.5 |
| (M.) MP | 50.0 ± 2.8 | 4.8 ± 0.5 |
| (N.) PDA | 33.0 ± 4.2 | 5.0 ± 0.0 |
| (O.) Oatmeal | 29.0 ± 2.8 | 5.0 ± 0.0 |

Quantification of the VOCs of *Hypoxylon* sp.

In order to quantify the concentration of volatile products being produced by *Hypoxylon* sp. continuously in the air space over in a 1 L bottle with a 300 ml slant of PDA, a direct method involving PTR-MS was used (FIG. 1). All ions in the PTR spectrum were monitored on a continuous basis and they ranged from mass 41-205 (FIG. 6). The maximum ion output was detected at ca. 6 days of incubation, which is consistent with the sensitivity of the assay organisms to the VOCs of *Hypoxylon* sp. (FIG. 7) (Table 1). Total maximum production of fungal VOCs was a 145 ppmv on day 6 and at a calculated rate of 7.65 ppmv/hr (FIG. 7). It seems that the overall VOC output of this fungus is substantial when compared to the output of other gas producing fungi (Ezra, et al., 2004a, Microbiology 150:4023-4031; Strobel, et al., 2008, Microbiology 154:3319-3328). The chief components of the gas mixture were compounds whose PTR mass spectra were consistent with ethanol, acetaldehyde, and a mass 121 which most likely represents protonated forms of unsaturated compounds whose mass is 120 (Table 3). Ions consistent with 1,8 cineole and other terpenoids producing masses at 81, 137 and 155 also allowed for an estimate of its concentration over the time course of the experiment and they peak at day 5.5-6 (FIG. 7). However, a direct estimate of 1,8 cineole production, based on mass 155, in the flask is ca. 800 ppbv at day 6 which is about 0.5% of the total fungal VOCs.

In summary, six day old cultures of *Hypoxylon* sp. displayed maximal VOC-antimicrobial activity against *Botrytis cinerea*, *Phytophthora cinnamomi*, *Cercospora beticola*, and *Sclerotinia sclerotiorum*, suggesting that the VOCs may play some role in the biology of the fungus and its survival in its host plant. Media containing starch- or sugar related substrates best supported VOC production by the fungus. Direct on-line quantification of VOCs was measured by proton transfer mass spectrometry (PTR-MS) covering a continuous range with optimum VOC production occurred at 6 days at 145 ppmv with a rate of production of 7.65 ppmv/hr. This demonstrates that 1,8-cineole (a monoterpene) is produced by a microorganism, which represents a novel and important source of this compound. This monoterpene is an octane derivative and has potential use as a fuel additive as do the other VOCs of this organism. Thus, fungal sourcing of this compound and other VOCs as produced by *Hypoxylon* sp. greatly expands their potential applications in medicine, industry, and energy production.

Example 2

The Paleobiosphere: a Novel Device for the In Vivo Testing of Hydrocarbon Production Utilizing Microorganisms Described herein is the construction and testing of a unique instrument, the Paleobiosphere, which mimics some of the conditions of the ancient earth. The instrument provides an experimental testing system for determining if certain microbes, when provided an adequate environment, can degrade biological materials to produce fuel-like hydrocarbons in a relatively short time frame that become trapped by the shale. The conditions selected for testing included a particulate Montana shale (serving as the "Trap Shale"), plant materials (leaves and stems of three extant species whose origins are in the late Cretaceous), a water-circulating system, sterile air, and a specially designed Carbotrap through which all air was passed as exhaust and volatile were hydrocarbons trapped. The fungus for initial testing was D-6, an *Annulohypoxylon* sp. isolated as an endophyte of *Citrus aurantifolia*. It produces, in solid and liquid media, a series of hydrocarbon-like molecules. Some of these including 1,8-cineole, 2-butanone, propanoic acid, 2-methyl-, methyl ester, benzene (1-methylethyl)-, phenylethyl alcohol, benzophenone and azulene, 1,2,3,5,6,7,8,8a-octahydro-1,4-dimethyl-7-(1-methylethenyl), [1S-(1a,7a,8ab)]. These were the key signature compounds used in an initial Paleobiosphere test. After 3 weeks, incubation, the volatiles associated with the harvested "Trap Shale" included each of the signature substances as well as other fungal-associated products: some indanes, benzene derivatives, some cyclohexanes, 3-octanone, naphthalenes and others. The fungus thus produced a series of "Trap Shale" products that were representative of each of the major classes of hydrocarbons in diesel fuel (Mycodiesel). Initial tests with the Paleobiosphere offer some evidence for a possible origin of hydrocarbons trapped in bentonite shale. Thus, with modifications, numerous other tests can also be designed for utilization in the Paleobiosphere.

The materials and methods employed in these experiments are now described.

The Paleobiosphere (PBS)

Figure 8:
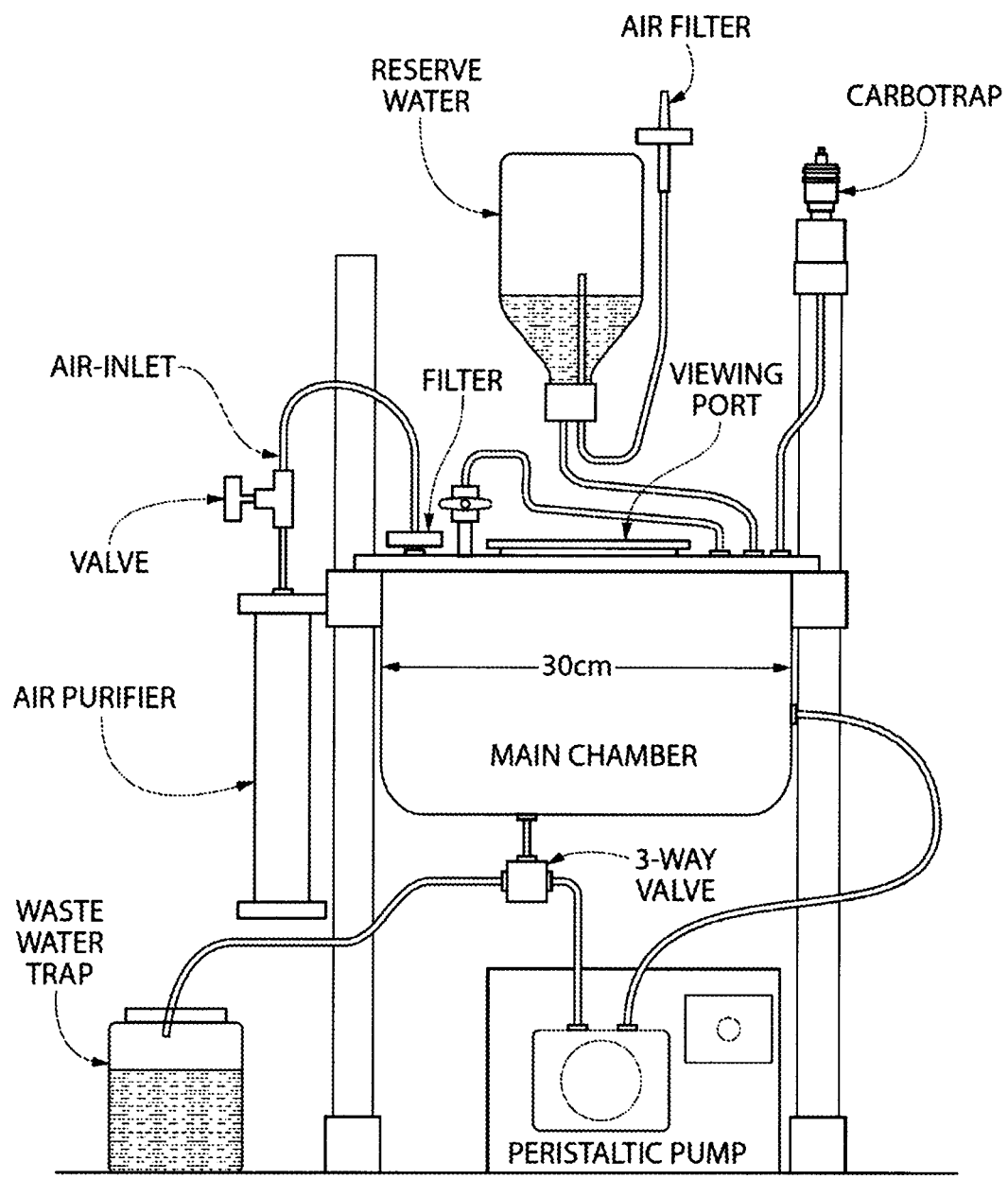
FIG. 8 is a photograph of The Paleobiosphere as designed and built and used in the experiments described elsewhere herein.

The instrument has been constructed from stainless steel parts including the main chamber and all valves, ports and traps. Tygon tubing lined with Teflon provides for all tube connections. The main chamber is 30 cm long, 21.5 cm wide and 14 cm deep (FIG. 8). The chamber has a sealed viewing port assembled on the top side. It also has a port connection to a water reservoir containing 2 l of sterile water with access to outside air via a stainless steel tube having a PALL 0.2 lm PTFE air filter mounted on it to equalize the pressure with sterile air (FIG. 8). The chamber also has an inlet valve allowing for the entry of air that has been passed through an air purifier (charcoal) as well as an air sterilization filter (as described elsewhere herein). At the base of the main chamber is another port with a three-way valve connected to a peristaltic pump via the chamber and an exit port on the right side allowing for water circulation through the pump and alternatively as an exhaust to the waste water trap. This easily allows for water to be replaced during the initial leaching processes.

Mounted on the top right side is a stainless steel column containing 10 g each (in line with each other) of Carbotrap materials A and B (Supelco Co.; Booth et al., 2011, Biotechnol. Lett. 10:1963-1972, see also U.S. patent application Ser. No. 13/591,968). The entire system has been built air-tight with the only air access being the air inlet system on the left side of the chamber (FIG. 8). A viewing port allows for monitoring of the events transpiring within the chamber.

Materials for the PBS

Plant Specimen

Leaves of plant species that are extant but whose relatives were contemporary during the late-Cretaceous period were chosen for this study since they are available (Tidwell, 1998, from Common fossil plants of Western North America, Smithsonian Institution, Washington). They served as the nutritive base for the fungus that was added to the PBS. These plants include *Acer platanoides, Platanus occidentalis* (both in the family Sapindaceae) and *Populus tremuloides* (Salicaceae), and were collected in the Intermountain West. Their early counterparts have been found in late Cretaceous and Tertiary deposits in the Intermountain West-USA (FIG. 9; Tidwell, 1998, from Common fossil plants of Western North America, Smithsonian Institution, Washington). They were cut into smaller pieces ca. 2 or 3 or 4 to 5 cm along with small stem fragments about 2-4 cm in length and autoclaved prior to placement in the PBS.

Shale

The selection of this material is critical to providing a testing basis for the hypothesis that shale can serve as a trap of biologically derived hydrocarbons. Normally, bentonite (shale), when water is added, behaves by quickly forming a pasty-like amorphous clay and as such would make it too difficult to handle in the experimental system. Therefore, more particulate and stable shale was needed for these experiments. It was found and collected from a roadside in the Melstone/Mosby, Mont. area at 46° 580 3900 N 107° 540 4900 W in an area of active oil production. It was pulverized and then separated with two screens at 8 and 16 mesh sizes. The material remained as particulates even when soaked in water. It was prebaked at 180° C. for 30 min under a constant stream of $N_2$ to remove residual hydrocarbons and used as the "bed shale". The shale to be used as "Trap Shale" was the same size but it had been baked for an additional 1 h at 300° C. also in a flow of $N_2$. This shale ("Trap Shale"=200 g) was evenly distributed in a 12 9 28 cm stainless steel 24-mesh envelope, and then placed on top of the mixture of bed shale and plant materials for use as the hydrocarbon trap. All shales incorporated into the biosphere were autoclaved twice for at least 25 min each.

Fungus

This microorganism was obtained as an endophyte from the fruit and stems of *Citrus aurantifolia* (Rutaceae—an ancient plant family genetically related to Sapindaceae) in a subtropical forest of Southwestern Florida in an environment very much resembling that Cretaceous period of Eastern Montana. The fungus was characterized as an *Annulohypoxylon* sp. on the basis of its ITS sequence identity (99% level on ca. 831 bpg) to other isolates of *Annulohypoxylon stygium* that had been deposited in Genbank. Its exact species designation is uncertain. All of the methods for obtaining sequence data are previously outlined (Ezra et al., 2004, Microbiology 150:4023-4031; Tomsheck et al., 2010, Microb. Ecol. 60:903-914). No sexual fruiting bodies were observed when this organism was cultured on its host tissues or host tissue extracts. Spores of the imperfect stage *Nodulisporium* sp. were observed, but only infrequently in potato/dextrose/agar culture and they all were in the ca. 1.5-2 μm size range, which is in the size range of other *Nodulisporium* sp. (Mends et al., 2012, J. Petroleum Environ. Biotech.; http://dx dot doi dot org/10 dot 4172/2157-7463 dot 1000117; Tomsheck et al., 2010, Microb. Ecol. 60:903-914). This organism was selected from a wide range of other hydrocarbon-producing fungi based on its collection site, a swampland area in Florida, and the fact that it makes 1,8-cineole and a number of other volatile signature compounds as do other *Hypoxylon* spp. and *Daldinia* spp. (Mends et al., 2012, J. Petroleum Environ. Biotech.; http://dx dot doi dot org/10 dot 4172/2157-7463 dot 1000117; Tomsheck et al., 2010, Microb. Ecol. 60:903-914). It was deposited in the Montana State University Culture Collection as No. 2387 and the ITS sequence is deposited in GenBank as JX 455754.

Carbotrap

This device is shown on the top right side PBS and was constructed according to all details previously described (Booth et al., 2011, Biotechnol. Lett, 10:1963-1972, see also U.S. patent application Ser. No. 13/591,968). The exhaust port gases from the chamber exit through this port and it was not connected until the beginning of day 4 of the 3 week incubation period (FIG. 8). It effectively serves as a trap for all hydrocarbons not being trapped by the "Trap Shale".

Water

All water added to the 1PBS over the course of the experiment had been deionized and sterilized by autoclaving.

Air

The air source was house air that was flowing at 11/min through a 4×22 cm charcoal air filter in-line with a PALL air sterilization filter and directly into the chamber as described above.

Temperature

All experiments were carried out at 22° C.

Hydrocarbon Production by the *Annulohypoxylon* sp. Isolate

At the outset it was critical to know which hydrocarbons were capable of being produced by the fungus that was to eventually be placed in the PBS. This was accomplished in two separate systems with subsequent GC/MS analysis of the volatiles. The organism was grown for 10 days on potato/dextrose/agar (PDA) and then analyzed for the production of volatiles as described elsewhere herein using a 30 min exposure time of the SPME fiber. Also, the organism was grown for 14 days in a shaking 7 l potato dextrose broth (24 g/l)

under a constant flow of air with the exhaust air being passed through a Carbotrap as previously described (Booth et al., 2011, Biotechnol. Lett. 10:1963-1972, see also U.S. patent application Ser. No. 13/591,968). The Carbotrap technology and a larger culture medium were used in order to obtain a more comprehensive view of additional volatile compounds being produced by the fungus (Hassan et al., 2012, Microbiology 158:465-473; Mends et al., 2012, J. Petroleum Environ. Biotech.; http://dx dot doi dot org/10 dot 4172/2157-7463 dot 1000117). The contents of the Carbotrap were eluted, condensed and trapped as a liquid as previously described and as more completely outlined below and then subjected to GC/MS (Booth et al., 2011, Biotechnol. Lett. 10:1963-1972, see also U.S. patent application Ser. No. 13/591,968). In all cases, appropriate control media, without the fungus, were treated in the exact manner and compounds detected therein were subtracted from the ones supporting fungal growth.

Quantitative and Qualitative Analyses of Trapped Hydrocarbons from the PBS

Carbog-trapped hydrocarbons were measured gravimetrically using before and after collection weights of the column itself after a 30 min dry purge at 30° C. with a 50 ml/min flow of dry $N_2$ (Booth et al. 2011). Then, the hydrocarbons were eluted in a programmable oven ranging up to 250° C. over the course of 1 h with dry $N_2$ at 600 ml/min and with hydrocarbon capturing in a vial bathed in liquid $N_2$ (Booth et al., 2011, Biotechnol. Lett. 10:1963-1972, see also U.S. patent application Ser. No. 13/591,968). The recovered hydrocarbons were weighed and subjected to GC/MS analysis. Hydrocarbons on the "Trap Shale" were measured and obtained in the same manner. This shale carried from 7-11% (w/w) relative to the amount of "Trap Shale" that was desorbed. The volatiles on both the Carbotrapped and "Trap Shale" samples were determined by SPME-GC/MS analysis. The final data presented were obtained by subtracting all compounds trapped in the control "Trap Shale" from the PBS hosting the fungus. Molecular sieves (Aldrich 4-8 mesh) were added to the "Trap Shale" samples in order to adsorb the water therein and allow for the determination of the weight of the hydrocarbon fraction (Booth et al., 2011, Biotechnol. Lett. 10:1963-1972, see also U.S. patent application Ser. No. 13/591,968).

For qualitative analysis of the hydrocarbons produced in all PBS samples and Carbotrap samples, the methods used were as previously described (Hassan et al., 2012, Microbiology 158:465-473; Mends et al., 2012, J. Petroleum Environ. Biotech.; http://dx dot doi dot org/10 dot 4172/2157-7463 dot 1000117; Strobel et al., 2008, Microbiol. Mol. Biol. Rev. 67:491-502). A pre-baked SPME fiber (Supelco) 50/30 divinylbenzene/carburen on polydimethylsiloxane on a stable flex-fiber was inserted through an opening in the septum of the 30 ml collection vial and the vapor phase were adsorbed for 45 min with the shale samples and only 1 min with the Carbotrap samples. The vapors were injected into a GC containing a 30 m×0.25 mm inner diameter ZB Wax capillary column with a film thickness of 0.5 lm. A thermal program of 30° C. for 2 min followed by an increase to 220 at 5° C./min. Ultra-high purity He was used as the carrier gas and the initial column head pressure was 50 kPa. Data acquisition and data processing were performed on the Hewlett Packard CHEMSTATION software system. Initial identification of the compounds produced by the endophyte was made via library comparison using the National Institute of Standards and Technology (NIST) database, and all chemical compounds described in this report use the NIST database chemical terminology. Authenticity of several compounds, identified by GC/MS, was reconfirmed by GC/MS of authentic standards. Standard compounds were run in a comparable manner as the fungal samples. Again, all compounds appearing either in the control "Trap Shale" or the control Carbotrap eluate were subtracted from the GC/MS results of PBS "Trap Shale" containing the fungus. Multiple GC/MS analyses were done on the Trap Shale and Carbotrap samples with comparable results.

Scanning Electron Microscopy

The shale samples from the PBS ("Trap Shale"-treatment and control) were fixed and slowly dehydrated in ethanol, critically dried, coated with gold, and examined with an FEI XL30 SEM Field Emission Gun at 5 kV with high vacuum mode using an Everhart-Thornley detector (Ezra). A gaseous secondary electron detector was used with a spot size of 3, at 15 kV. The temperature was 4° C. with a chamber pressure ranging from 5 to 6 T, providing humidity up to 100% at the sample. Shale/fossil samples from the field were not dehydrated and subjected directly to gold coating and SEM observations. In this manner, as previously observed, if the fungal hyphae were contemporary, and not appropriately fixed, prior to gold coating, they would collapse under the vacuum in the SEM.

UV-Visible Measurements

Aqueous samples from the PBS that were first diluted 1:9 v/v (sample to water) and then scanned from 540 to 230 nm in a 1 ml cuvette having a 1 cm light path. The results are reported as total absorbance at 260 nm for each sample.

PBS Experimental Design

Figure 10:
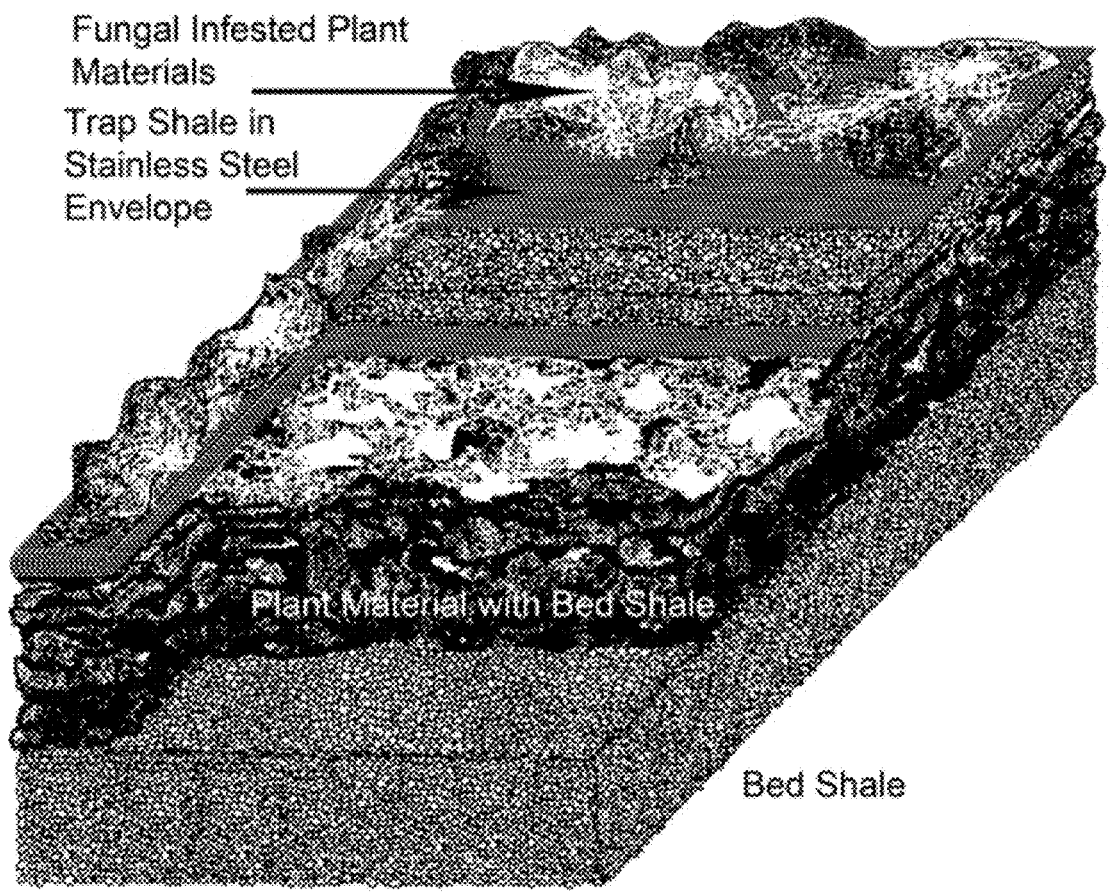
FIG. 10 is an illustration of the experiment set-up of the Paleobiosphere with a bed layer overlaid with a mixture of 200 g of shale, 25 g of plant materials and 10 g of 1 month old plant matter infested with the fungus. The Trap Shale (200 g) is contained in an envelope of stainless steel overlaying the shale/plant mixture. On top is a lightly distributed fungal inoculum of infested plant material.

All parts of the instrument were sealed in aluminum foil and autoclaved for 25 min. The water, shale and plant materials (8 g of each of the three species) were also autoclaved. The fungus inoculum to be used had been grown for 1 month on 10 g of a mixture of the fragments of leaves and stems of three plant species. Then, 800 g shale were evenly placed in the base of the main chamber (Bed Shale), followed by 25 g leaves and stem pieces that were mixed with 200 g bentonite shale, plus 10 g fungal-infested plant material. The plant/shale layer was overlaid with the steel mesh envelope containing 200 g of baked sterile shale as the "Trap Shale". On top of the "Trap Shale" screen was scattered an additional 10 g fungal inoculated plant material (FIG. 10). The top plate with viewing port was sealed after 1.2 l of water had been added to the main chamber (FIG. 8). The peristaltic pump was then turned on and adjusted to a 50 rpm rate in order to circulate and move the water and fungal spores and hyphal fragments in the system. Sterile air was applied to the system. An initial 4 days of incubation and leaching of the plant materials by the water was critical to the success of the experiment since the tannins present in the plant materials prevent the abundant growth of the fungus. The Carbotrap was not connected to the exhaust of the main chamber until after this 4 day period since fungal growth was at a minimum. Then, all water that was drained from the system (450 ml) and fresh water added from the reservoir.

After 4 additional days, the system was again drained and allowed to incubate without free water for 4 days, at which time new water was added, the pump turned on and the process repeated twice again with a 5 day final drain period until 21 days had expired. The water cycling was done to mimic the conditions of periodic rainfall in a semi-tropical rainforest. Periodically, additional water was added to allow for an adequate flow through the system since some drying was occurring. The control PBS was treated exactly as above except no fungal inoculum was placed in the main chamber, only autoclaved leaves and stems in the same amounts. The amount of Carbotrapped hydrocarbons was determined gravimetrically after a dry purge, and then desorbed and weighed again (Booth et al., 2011, Biotechnol. Lett. 10:1963-1972, see also U.S. patent application Ser. No. 13/591,968). The shale harvested from the "Trap Shale" was also desorbed by heating and trapped in a vial cooled with liquid nitrogen (Booth et al., 2011, Biotechnol. Lett. 10:1963-1972, see also U.S. patent application Ser. No. 13/591,968). In order to achieve, what appears to be an optimum experimental outline as described above, many preliminary experiments were conducted. The results on these experiments provided guidance on what conditions would be best suited for the PBS.

The amount of Carbotrapped hydrocarbons was determined by gravimetric means, after a dry purge, and then desorbed and weighed again (Booth et al., 2011, Biotechnol. Lett. 10:1963-1972, see also U.S. patent application Ser. No. 13/591,968). The shale harvested from the "Trap Shale" was also desorbed by heating and trapped in a vial cooled with liquid nitrogen (Booth et al., 2011. Biotechnol. Lett. 10:1963-1972, see also U.S. patent application Ser. No. 13/591,968).

The results of the experiments are now described.

Hydrocarbon Production by *Annulohypoxylon* sp.

When *Annulohypoxylon* sp. was grown on PDA for 10 days and assayed for the production of volatiles several hydrocarbon derivatives appeared of interest including 1,8-cineole, 1-butanol, 3-methyl- and 2-naphthalenol, 3-methyl (Table 5). These compounds served as the signature substances in the PBS and thus indicate what compounds produced therein were of fungal origin (Table 5).

TABLE 5

A GC/MS analysis of the volatiles being produced on a 10 day old culture of *Annulohypoxylon* sp. actively growing on a potato/dextrose/agar plate

| Retention time (min) | Relative area | Compound | Molecular weight (g/mol) | Quality |
|---|---|---|---|---|
| 5.15 | 51 | 1-Propene, 2-methyl-, trimer | 168 | 83 |
| 5.91 | 52 | †a-Thujene | 136 | 90 |
| 10.15 | 55 | †*Benzene, 1,3-dimethyl- | 106 | 97 |
| 10.71 | 3332 | †1,8-Cineole | 154 | 98 |
| 10.88 | 231 | †1-Butanol, 3-methyl- | 88 | 83 |
| 19.57 | 4662 | *†Benzaldehyde | 106 | 97 |
| 24.25 | 87 | *trans-Caryophyllene | 204 | 70 |
| 41.8 | 455 | 2-Naphthalenol, 3-methoxy- | 174 | 90 |
| — | 1508 | 7 Unknowns | — | — |
| Overall area | 12513 | | | |

*Sometimes found in control plates in small concentrations;
†An authentic compound yielded the same spectrum and retention time as the fungal product While the list is not long it did serve to encourage further studies on this endophytic fungus. Surprisingly, when the organism was grown in a 7 l batch of PD broth with shaking and the hydrocarbons trapped on a Carbotrap column, eluted and analyzed, the number of detectable hydrocarbon-related compounds produced by this fungus greatly increased over the plate GC/MS analysis and included representative compounds in each class of crude oil substances. Present in the analysis were branched hydrocarbons, benzene derivatives, cycloalkanes, some polyaromatic hydrocarbons (the azulenes) and various smaller molecular weight aldehydes, esters, acids and alcohols (Table 6).

TABLE 6

A GC/MS analysis of the Carbotrapped gases of *Annulohypoxylon* sp. after a 2 week incubation on a 7 l culture grown on potato dextrose broth at 22° C.

| Retention time (min) | Relative area | Compound | Molecular weight (g/mol) | Quality |
|---|---|---|---|---|
| 1.89 | 129 | †Acetaldehyde | 44 | 74 |
| 2.51 | 3887 | Cyclobutane, ethenyl- | 82 | 94 |
| 3.69 | 569 | †2-Butanone | 72 | 78 |
| 4.06 | 783 | †Propanoic acid, 2-methyl-, methyl ester | 102 | 91 |
| 4.62 | 572 | Furan, 2,5-dimethyl- | 95 | 91 |
| 6.59 | 6241 | †2-Butenal, (E)- | 70 | 91 |
| 7.28 | 33 | 1-Butanol, 3-methyl-, formate | 116 | 72 |
| 8.72 | 59 | Cyclohexane, 1,2,4-tris(methylene)- | 120 | 81 |
| 9.04 | 33 | Cyclohexane, 1-(1-propynyl)- | 120 | 81 |
| 10.02 | 21 | Benzene, (1-methylethyl)- | 120 | 91 |
| 10.95 | 846 | Cyclobutanone, 2-ethyl- | 98 | 72 |
| 10.96 | 71 | †1-Butanol, 3-methyl- | 88 | 78 |
| 11.45 | 27 | Dodecane, 2,6,11-trimethyl- (or isomer) | 212 | 80 |
| 12.11 | 19 | Benzene, cyclopropyl- | 118 | 92 |
| 12.71 | 35 | Benzene, 1-methyl-2-(1-methylethyl)- | 134 | 95 |
| 12.97 | 16 | Dodecane, 2,6,11-trimethyl- | 212 | 93 |
| 15.1 | 15 | Benzene, 1-ethenyl-2-methyl- | 118 | 94 |
| 15.69 | 77 | 1,3-Cyclopentadiene, 5-(1-methylpropylidene)- | 120 | 80 |
| 16.48 | 27 | Bicyclo[4.2.0]octa-1,3,5-triene, 7-methyl- | 118 | 95 |
| 17.76 | 180 | †Acetic acid | 60 | 90 |
| 18.67 | 23 | Cyclohexanone, 5-methyl-2-(1-methylethyl, cis- | 154 | 98 |
| 19.06 | 15 | Longifolene-(V4) | 204 | 78 |
| 19.34 | 14782 | Formic acid | 46 | 78 |
| 20.07 | 2422 | †Propanoic acid | 74 | 91 |

TABLE 6-continued

A GC/MS analysis of the Carbotrapped gases of *Annulohypoxylon* sp. after a
2 week incubation on a 7 1 culture grown on potato dextrose broth at 22° C.

| Retention time (min) | Relative area | Compound | Molecular weight (g/mol) | Quality |
|---|---|---|---|---|
| 21.05 | 114 | Cyclohexane, 1-ethenyl-1-methyl-2,4-bis(1-methylethenyl)-, [1S-(1a,2b,4b)]- | 204 | 99 |
| 23.50 | 669 | 2(5H)-Furanone, 5-methyl- | 98 | 90 |
| 23.66 | 34 | Bicyclo[3.1.0]hexane, 6-isopropylidene-1-methyl- | 136 | 86 |
| 24.37 | 791 | Azulene, 1,2,3,4,5,6,7,8,8a-octahydro-1,4-dimethyl-7-(1-methylethenyl), [1S-(1a,7a,8ab)]- | 204 | >70 |
| 24.55 | 287 | Caryophyllene | 204 | 81 |
| 25.15 | 14 | 1H-Cycloprop[e]azulene, decahydro-1,1,7-trimethyl-4-methylene-, [1aR-(1aa,4ab,7a,7ab,7ba)]- | 204 | 89 |
| 25.8 | 46 | 2-Propenoic acid, 2-phenylethyl ester | 176 | 72 |
| 28.48 | 8847 | ⁺Phenylethyl alcohol | 122 | 94 |
| 39.05 | 888 | Benzophenone | 182 | 96 |
| — | 10245 | 29 Unknown compounds | — | — |
| Overall area | 52819 | | | |

The dry weight of the fungus was 22 g.
⁺Indicates that an authentic control had the same retention and MS as the fungal product Of great interest was the appearance of a number of cycloalkanes including cyclohexane, cyclohexene, cyclohexanone and cyclopentane derivatives since many of these reduced products are some of the most abundant compounds associated with crude oils and diesel fuels. It is notable that stereocenters exist in some of these molecules as well with comparable compounds found in diesel (Table 6). Some of the key compounds found in the PDA plate with the fungus did not appear in the Carbotrap fraction including 1,8-cineole, but others did appear and this is undoubtedly related to the conditions of fungal growth. Nevertheless, this organism was selected for use in the PBS in order to learn if its volatiles would collect in the "Trap Shale" of the instrument since the spectrum of volatiles being made were very promising.

The Paleobiosphere Experiment

Figure 9:
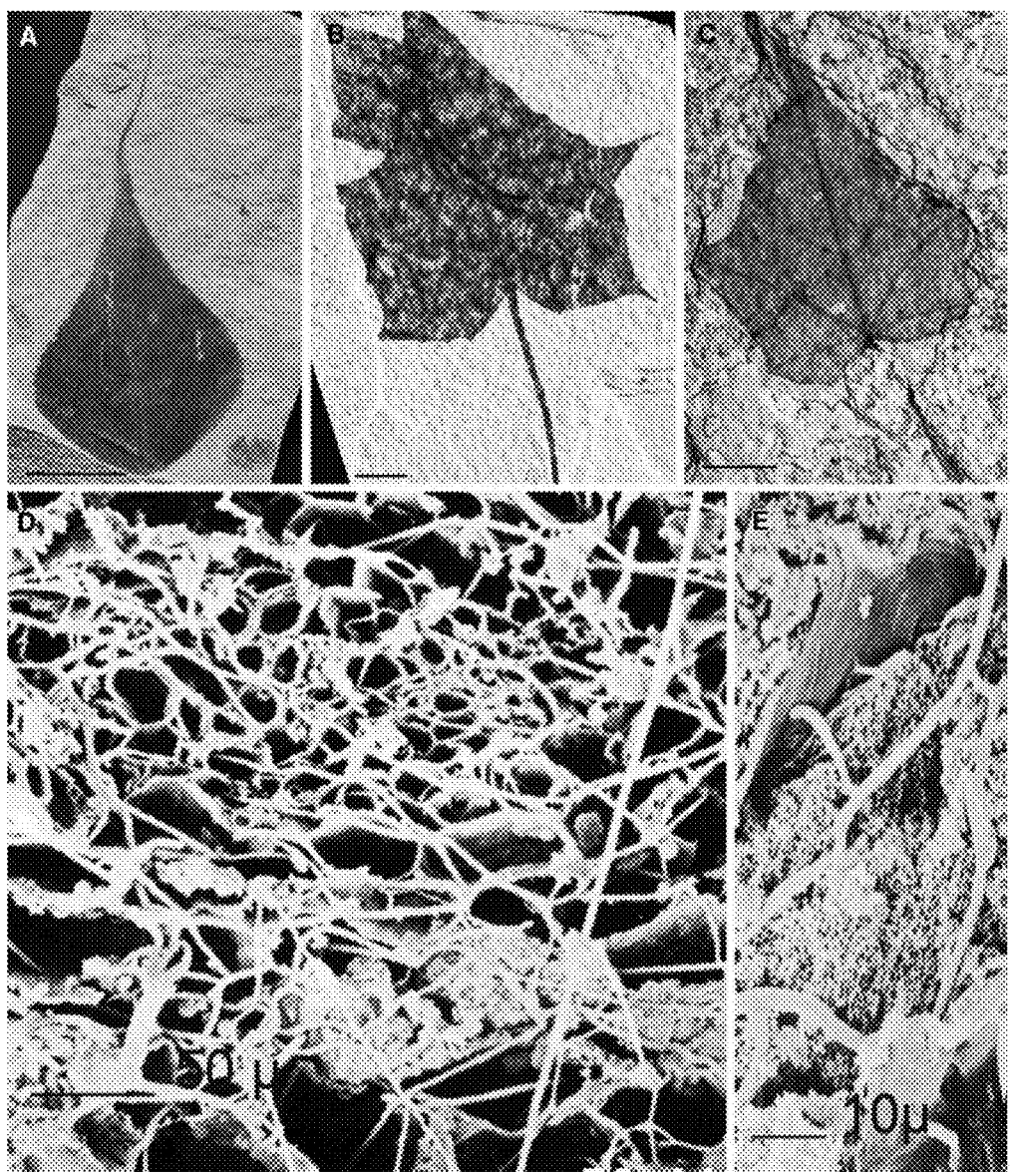
FIG. 9, comprised of FIGS. 9A-9E, is a series of photographs of paleobotanical examples of the plants used in the PBS experiments.
Figure 11:
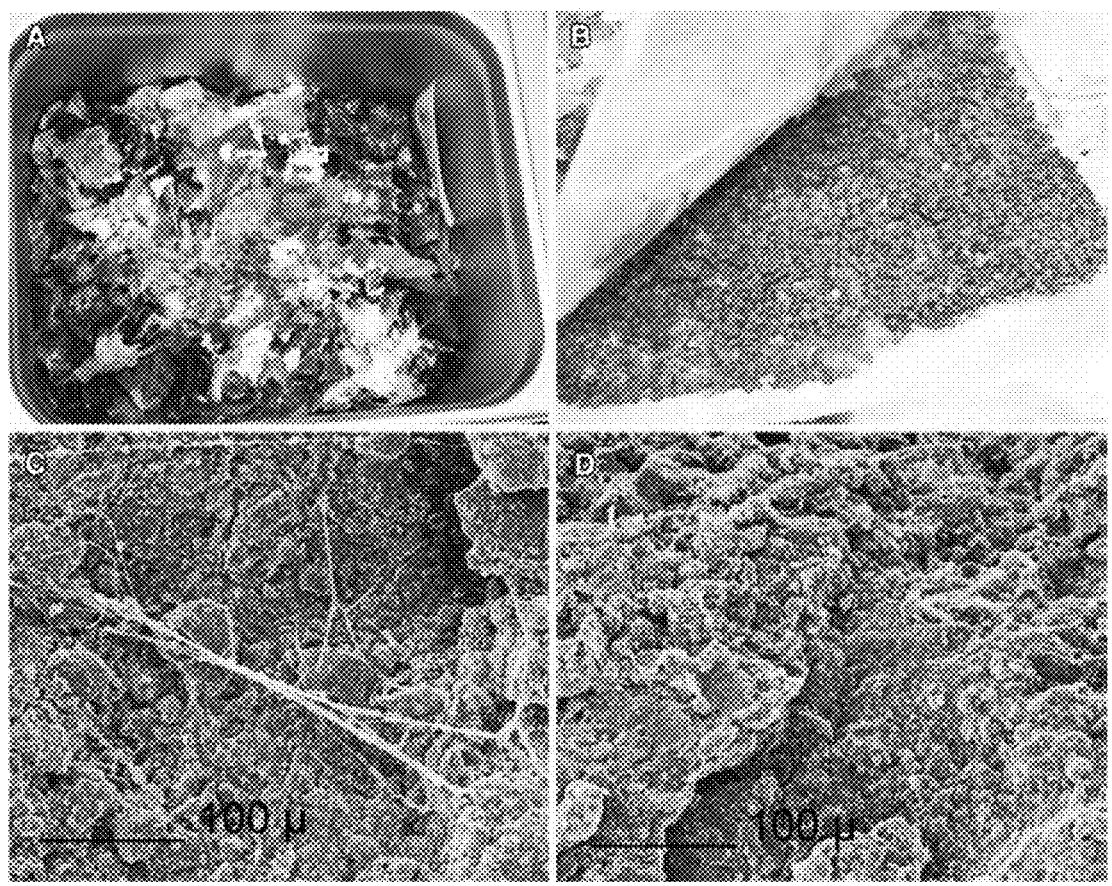
FIG. 11, comprised of FIGS. 11A-11D, is a series of photographs representing the PBS (under the "Trap Shale" layer) at the termination of the experiment.

The plant materials selected for use in the PBS supported fungal growth very well (FIG. 11). This included leaves of three plant species selected on the basis of their paleobotanical origins (FIG. 9). Stem pieces of these species were also added to the instrument since paleobotanical evidence has been discovered showing the presence of fossilized fungi in stem tissues in Montana shale near the same location as the shale used in these experiments (FIG. 9). The *Annulohypoxylon* sp. was capable of colonizing each of the plant materials in the PBS including leaf blades, petioles and stem fragments after a few days of leaching with sterile water.

In the PBS, colonization of the plant materials began in earnest after 4 days when the first free water was removed and eventually completely engulfed all biological materials (FIG. 11). Removal of free water on a periodic basis served to leach tannins from the leaves and stems in the PBS and promoted fungal growth. In natural conditions, these polyphenolic substances are inhibitory to fingi and the leaching of plant materials on the forest floor occurs during a rainfall resulting in a concomitant dark discoloration of rainforest streams and rivers. It was obvious that the control PBS was much less dark with less absorbance at 260 nm than the PBS supporting fungal growth both at the beginning and at the end of the incubation period (Table 5). Quite unexpectedly, the fungus had also colonized the "Trap Shale" in the PBS (FIG. 11).

Trapped Hydrocarbons in the Paleobiosphere

At the termination of the experiment 29.8 mg hydrocarbons were trapped by the "Trap Shale" in the PBS containing the fungus as compared to 1.2 mg in the control (Table 5). Likewise, over eight times the amount of hydrocarbons on the Carbotrap in the fungal PBS than the control PBS were trapped (Table 5). About 50% of the trapped hydrocarbons were recovered as liquids from each of the Carbotraps when desorbed and condensed in a vial in the presence of liquid nitrogen (Table 5). These results suggest that the fungus introduced into the PBS was contributing to the production of hydrocarbons in the PBS system and that the "Trap Shale" did function "in vivo" to collect some of the hydrocarbons produced in the PBS but non-trapped ones were effectively removed from the gas stream by the Carbotrap attached to the PBS (FIG. 8; Table 5).

Nature of the Trapped Hydrocarbons from the PBS

Compounds recovered from the "Trap Shale" in the PBS containing the fungus include representatives of all of the major classes of compounds found in diesel including straight and branched chained hydrocarbons, cyclic alkanes, benzene derivatives and polyaromatic hydrocarbons such as the naphthalenes and azulenes. Most importantly, the major signature compounds of 2-butanone, propanoic acid, 2-methyl-, methyl ester, benzene(1-methylethyl)-, 1,8-cineole, phenylethyl alcohol, benzophenone and azulene, 1,2,3,5,6,7,8,8a-octahydro-1,4-dimethyl-7-(1-methylethenyl), [1S-(1a,7a,8ab)]- each appeared in the "Trap Shale" (Table 8). This observation provides unequivocal evidence that fungal hydrocarbons, produced in the plant decay processes, can be trapped and retained by the bentonite shale. Even upon extensive drying (30 h at 30° C.) the majority of these substances were retained by the shale.

TABLE 7

Collective data on the recovery of hydrocarbons from the PBS treatment (with the endophytic fungus—*Annulohypoxylon* sp.) and the control (without the fungus)

| | Carbotrap total hydrocarbons (mg) | Recovered from Carbotrap (mg) | Trap Shale recovered hydrocarbons (mg) | Total absorbance first water from PBS at 260 k | Total absorbance last water from PBS at 260 k |
|---|---|---|---|---|---|
| PBS with fungus | 67 | 44.6 | 29.8 | 8325 | 5875 |
| PBS control without fungus | 8 | 3 | 1.2 | 4675 | 1875 |

The results in this table are from one experiment and are exemplary of other experiments that were conducted with the PBS.

Other volatile compounds appearing on the "Trap Shale"-list of hydrocarbons were either made by fungal metabolism or released products from the plant materials by fungal action since all compounds in the control "Trap Shale" and Carbotrap-control shale were removed from this list. It would appear, for instance that the cyclohexanes-butyl and pentyl derivatives are directly a result of fungal metabolism since cyclohexanes, cyclohexenes and cyclohexanones were all detected in the fungal hydrocarbon mixture from the Carbotrap of a 7 l culture (Tables 6, 8).

TABLE 8

The hydrocarbon products recovered from the PBS (treated-fungal) 200 g of "Trap Shale"

| Retention Time (min) | Relative area | Compound | Molecular Weight (g/mol) | Quality |
|---|---|---|---|---|
| 3.46 | 713 | Ethyl acetate | 88 | 91 |
| 3.67 | 388 | 2-Butanone | 72 | 72 |
| 4.01 | 1747 | Propanoic acid, 2-methyl-, methyl ester | 102 | 91 |
| 5.82 | 184 | Acetic acid, 2-methylpropyl ester | 116 | 78 |
| 5.96 | 485 | Decane, 4-ethyl- | 170 | 80 |
| 7.13 | 430 | Cyclohexane, butyl- | 140 | 72 |
| 7.43 | 634 | Undecane | 156 | 97 |
| 7.88 | 118 | 2-Butenal, 2-methyl-, (E)- | 84 | 94 |
| 8.46 | 2255 | 1-Butanol, 3-methyl, acetate | 130 | 80 |
| 9.07 | 789 | Naphthalene, decahydro-, trans- | 138 | 92 |
| 9.73 | 413 | Cyclohexane, pentyl- | 154 | 87 |
| 9.74 | 78 | 1-Penten-3-ol | 86 | 72 |
| 9.87 | 75 | Benzene (1-methylethyl)- | 120 | >70 |
| 10.05 | 616 | Dodecane | 170 | 87 |
| 10.21 | 665 | trans-Decalin, 2-methyl- | 152 | 93 |
| 10.79 | 207 | 1,8 Cineole | 154 | >70 |
| 11.02 | 402 | trans-4a-Methyl-decahydronaphthalene | 152 | 86 |
| 12.2 | 488 | 3-Octanone | 128 | 94 |
| 13.55 | 400 | Benzene, 1-methyl-4-propyl- | 134 | 91 |
| 13.98 | 427 | Butanoic acid, 3-hexenyl ester, (Z)- | 170 | 72 |
| 15.13 | 447 | Benzene, 1-ethyl-2, 4-dimethyl- | 134 | 95 |
| 15.49 | 420 | Indane | 118 | 76 |
| 16.17 | 419 | Indane, 1-methyl- | 132 | 87 |
| 16.32 | 382 | 4-Hepten-3-one, 5-ethyl-4-methyl- | 154 | 76 |
| 18.25 | 775 | 4,7-Methanoazulene, 1,2,3,4,5,6,7,8-octahydro-1,4,9, 9-tetramethyl-, [1S-(1a,4a,7a)]- | 204 | 98 |
| 18.59 | 628 | Benzene, 1,2,3,5-tetramethyl- | 134 | 94 |
| 18.92 | 561 | Benzene, 1-ethenyl-4-ethyl- | 132 | 87 |
| 19.01 | 531 | Benzene, (1-methyl-1-butenyl)- | 146 | 91 |
| 19.02 | 553 | 1H-Indene, 2,3-dihydro-1,2-dimethyl- | 146 | 76 |
| 19.58 | 479 | Naphthalene, 1,2,3,4,-tetrahydro- | 132 | 86 |
| 20.46 | 483 | Benzene, pentamethyl- | 148 | 93 |
| 22.06 | 466 | Benzaldehyde, 3-methyl- | 120 | 97 |
| 23.08 | 371 | Estragole | 148 | 98 |
| 23.98 | 2656 | Azulene, 1,2,3,4,5,6,7,8,8a-octahydro-1,4-dimethyl-7-(1-methylethenyl), [1S-(1a,7a,8ab)]- | 204 | 99 |
| 24.33 | 70 | Benzene, 1,2-dimethoxy- | 138 | 97 |
| 28.47 | 68 | Phenylethyl alcohol | 122 | 94 |
| 39.04 | 60 | Benzophenone | 182 | 91 |
| — | 11420 | 18 Unknown compounds | — | — |
| Overall area | 32740 | | | |

Compounds that are in bold letters are those also found in the Carbotrap of the 7 l culture of *Annulohypoxylon* sp. in Table 6. All compounds found in the control "Trap Shale" and Carbotrap have been subtracted from this list Furthermore, compounds of this type are not generally found in higher plants, and although not wishing to be bound to any particular theory, suggests that the plant material was not the direct source of the compounds (Robinson, 1983, from The organic constituents of higher edn. Cordus Press, Amherst). Likewise, it appears that the fungus is capable of making a number of benzene derivatives, including the indanes and estragole, but only one appears to be common in the both the 7 1 liquid culture Carbotrap and "Trap Shale" samples (Tables 6, 8). Also all of the 4-5 carbon aldehydes and esters such as 2-butenal, 2-methyl are of fungal origin since relatives of these compounds are in the "Trap Shale" products, for instance 3-methyl- and 1-butanol, formate in the Carbotrap and the acetate derivative appearing in the "Trap Shale" (Tables 6, 8). Another compound of interest is 3-octanone which commonly appears in the analysis of fungal hydrocarbons and can be found in GC/MS analysis of crude oil from Melstone, Mont., crude oil (Table 8). This aldehyde is not found in plants (Robinson, 1983, from The organic constituents of higher edn. Cordus Press, Amherst). It is also noteworthy that various hydronaphthalene derivatives are found in the analysis of the "Trap Shale" and these types of volatiles are commonly associated with diesel. Naphthalene and naphthalene derivatives are only rarely found in plants but have been found in the analysis of fungal hydrocarbons and thus are probably of fungal origin (Daisy et al., 2002, Microbiology 148:3737-3741; Strobel, 2006, J. Ind. Microbiol. Biotechnol, 33:514-522).

Also of interest, are the straight and branched chained hydrocarbons that appeared in the "Trap Shale" analysis (Table 8). Hydrocarbons of this type have been noted in the gas analysis of the Carbotrap contents in the 7 1 fermentation and have been previously reported from other fungi (Tables 6, 8; Ahamedg and Ahring, 2011, Bioresour. Technol. 102: 9718-9722; Banerjee et al., 2010, Mycosphere 3:241-247; Griffin et al., 2010, Microbiology 156:3814-3829; Strobel et al., 2008, Microbiology 154:3319-3328). Most likely they too are of fungal origin. There is also an apparent absence of any of the small molecular weight organic acids (formic, acetic and propanoic) in the Carbotrap of the 7 1 fermentation but not in the Trap Shale of the PBS (Tables 6, 8). Although not wishing to be bound to any particular theory, this suggests that the shale is somewhat selective in the types of molecules that may be trapped by it. The fungus apparently makes these acidic molecules in the PBS since so many esters of these compounds were trapped by the shale (Table 8).

The Carbotraps

A relative large hydrocarbon fraction was recovered from the Carbotrap in the PBS (Table 7). These compounds had escaped being collected by the "Trap Shale" in the PBS and left the chamber of the instrument only to be trapped by the Carbotrap materials (FIG. 8; Table 7). The compounds were some of the same substances that were on the "Trap Shale" as well as numerous related straight and branched chained hydro-carbons, cycloalkanes, benzene derivatives and others (Table 8). Likewise, the amount of hydrocarbons in the Carbotrap of the control PBS was substantially lower than the fungal counterpart (Table 7). It mostly contained an assortment of aldehydes, ketonesg, benzenes and furans. These compounds were present in low amounts in the control Carbotrap and only a few were the same as those in the fungal PBS-Carbotrap. The source of these volatiles in the Control Carbotrap is apparently related to the autoclaving of the plant materials and changes brought by heating and wetting of the materials.

The Paleobiosphere and VOC Production

Described herein is the development and testing of a device termed the Paleobiosphere. This device was constructed to mimic some of the conditions of the ancient earth in order to provide evidence for the hypothesis that the biological degradation (using an endophytic fungus) of plant materials can be an apparent source of hydrocarbons using shale as a trapping medium for the microbial derived compounds. Overall, it appears that the initial experiments to demonstrate this phenomenon have provided some experimental evidence for the hypothesis (Tables 7, 8). Representative compounds in each class of substance in diesel were present in the final "Trap Shale" analysis of the PBS (Table 8). This finding, at least provides a basis for further studies using the PBS in a multitude of different ways. These may include modifications of substrata, individual microbes and combinations thereof as well as the trapping media (other shales, sands and limestones) as well as variations of temperature, water levels and length of incubation periods. One possible test is an experimental set up in which nothing is sterilized and only the natural flora of both the shale and the non-autoclaved plant materials are added to the PBS.

It seems likely that the processes involving hydrocarbon formation in the earth did not take millions of years and tons of pressure and high temperatures as proposed. It does appear likely that some plant-associated microorganisms were involved in producing some of the ingredients in crude oil as well as sets of other slightly oxygenated molecules that were the precursors of totally reduced hydrocarbons (as found in crude oil). Although not wishing to be bound to any particular theory, it is hypothesized that some of these biologically-produced molecules, such as aldehydes, ketonesg, alcohols and alkenes released by microbes and trapped on shale under the reducing conditions of the earth, may have been modified to the final reduced products that are found in crude oil. They would have accumulated in shale, and eventually with changing pressures in the earth's layers began to pool in certain locations. The PBS now provides support of the ability of bentonite shale, in vivo, to trap hydrocarbons being produced by an endophytic fungus that is actively degrading dead plant materials.

Example 3

An Endophytic *Nodulisporium* sp. From Central America Producing Volatile Organic Compounds with Both Biological and Fuel Potential Described herein is a *Nodulisporium* sp. (*Hypoxylon* sp.) which has been isolated as an endophyte of *Thelypteris angustifolia* (Broadleaf Leaf Maiden Fern) in a rainforest region of Central America. It has been identified both on the basis of its morphological characteristics and by scanning electron microscopy as well as ITS sequence analysis. The endophyte produces volatile organic compounds (VOCs) that have both fuel (mycodiesel) and use for biological control of plant disease. When grown on potato dextrose agar, the organism uniquely produces a series of ketonesg, including acetone; 2-pentanone; 3-hexanone, 4-methyl; 3-hexanone, 2,4-dimethyl; 2-hexanone, 4-methyl, and 5-hepten, 2-one and these account for about 25% of the total VOCs. The most abundant identified VOC was 1,8 cineole, which is commonly detected in this group of organisms. Other prominent VOCs produced by this endophyte include 1-butanol, 2-methyl, and phenylethanol alcohol. Moreover, of interest was the presence of cyclohexane, propyl, which is a common ingredient of diesel fuel. Furthermore, the VOCs of this isolate of *Nod-*

*ulisporium* sp. were selectively active against a number of plant pathogens, and upon a 24 h exposure caused death to *Phytophthora palmivora, Rhizoctonia solani*, and *Sclerotinia sclerotiorum* and 100% inhibition to *Phytophthora cinnamomi* with only slight to no inhibition of the other pathogens that were tested. Although not wishing to be bound to any particular theory, it is becoming increasingly apparent that each isolate of this endophytic *Nodulisporium* spp., including the *Daldina* sp. and *Hypoxylon* spp. teleomorphs, seems to produce its own unique set of VOCs.

The materials and methods employed in these experiments are now described.

Isolation of the Endophyte

Small stems of *Thelypteris angustifolia* (willd.) Proctor, not showing any signs of disease, were procured from the Rio San Juan area of Central America (11° 02' 602" N, 83° 50' 355"W) transported to the laboratory in a sterile polythene bag and stored at 4° C. until processed. Plant materials including the leaves were cut under sterile conditions into small pieces (2-5 cm) and surface sterilized with 90% alcohol for 2 min. After drying under sterile laminar air flow in a biosafety hood and passing through a flame, the outer tissues were removed and the internal tissues were cut into smaller pieces of 0.5 to 1 cm and placed on PD Agar plates harboring a colony of 7-days-old *Musocodor albus*. This is a selective procedure to isolate organisms that are resistant to the toxic VOCs of *M. albus*. Usually, organisms growing in the presence of *M. albus* are capable of producing bioactive VOCs themselves (Strobel et al., 2001, Microbiology 147:2943-2950; Tomsheck et al., 2010, Microbial. Ecol. 60:903-914). The plates were incubated at 23° C. for three weeks, Hyphal tips of endophytes emerging out of the plant tissues were picked and plated on PDA.

One endophyte of particular interest, emerging from tissues of *T. angustifolia*, was labeled Ni25-2A. It was noted that this organism was emitting vapors that resembled those of other *Nodulisporium* sp., especially those producing 1,8-cineole (Tomsheck et al., 2010, Microbial. Ecol. 60:903-914). After incubation of the fungus on PDA laced with sterilized barley seed, the fully colonized seeds were placed in 15% glycerol and stored at −70° C. (Tomsheck et al., 2010, Microbial. Ecol. 60:903-914). All media and chemicals were obtained from Difco (USA) and Sigma Chem. Co. (St Louis, Mo., USA) respectfully. For the evaluation of its growth on different sugars, the endophyte was grown on Czapek-Dox Agar (NaNO$_3$ 3 g/l, K$_2$HPO)$_4$ 1.0 g/l, MgSO$_4$.7H2O 0.5 g/l, KCl 0.5 g/l, FeSO$_4$.7H$_2$O 0.1 g/l, and Agar 15 g/l) supplemented with 30 g/l of a number of individual sugars.

Bioactivity Profiling

Initially, antifungal and antibacterial activities were assessed against *Staphylococcus aureus, Bacillus subtilis, Candida albicans, Fusarium solani*, and *Sclerotinia sclerotiorum*. For this purpose, small plugs (3 mm diameter) of each test fungi were placed a centimeter away from the edge of a 7-day-old Ni25-2A culture. The bacterial and yeast cultures were streak-inoculated, starting from the edge of the colony towards the periphery of the plate. The plates were wrapped with Parafilm and incubated at 23° C. or 37° C. for 24-48 h for fungi and bacteria, respectively. Growth of the test pathogens were reported as percent inhibition as compared with their relevant controls. The bacterial and yeast cultures were visually evaluated for the amount of colony inhibition.

For the activity of the VOCs produced by Ni25-2A, an agar strip of 2 cm was removed from the middle of a PDA plate. Ni25-2A was inoculated on the half-moon of the medium and cultivated for 7 days at 23° C. Plugs (3 mm) of each of a panel of test fungi consisting of several plant and human pathogens were placed on the other half of the plate in order to grow them under the artificial atmosphere produced by the VOCs of the endophyte (Strobel et al., 2001, Microbiology 147:2943-2950). The bacterial and yeast cultures were streaked individually on the opposite half of the plates. The plates were wrapped with a double layer of Parafilm and incubated at 23° C., and the results were noted at 48 h (Strobel et al., 2001, Microbiology 147:2943-2950).

Estimation of IC$_{50}$

Several of the VOCs produced by Ni25-2A were obtained commercially. The compounds tested were 2-pentanone; 3-hexanone, 2-4-dimethyl-; 1-butanol, 2-methyl-; 1,8-cineole; propionic acid, 2-methyl-; and farnesene. They were placed in a mixture according to the proportion in which they appeared in the GC/MS profile (see relative areas in Table 10). Aliquots of the mixture ranging from 0.05 to 0.5 µl/ml were placed in pre-sterilized 6 mm micro-cups at the center of the agar surface of a PDA plate having a 50 ml headspace. Test organisms were inoculated on the plates as 3 mm plugs of 7-day-old cultures and on normal PDA plates as controls. Percent inhibition of fungal growth was calculated after 48 h of growth and plotted against the concentration of the mixture per milliliter of the airspace for each organism. The inhibitory concentration yielding 50% inhibition of fungal growth (IC50) for each organism was calculated through extrapolation from the plots (Strobel et al., 2001, Microbiology 147: 2943-2950).

Scanning Electron Microscopy

The endophyte (Ni25-2A) was grown on gamma-irradiated carnation leaves for 3 weeks to promote the formation of fruiting bodies (Tomsheck et al., 2010, Microbial. Ecol. 60:903-914). The samples were slowly dehydrated in ethanol, critically dried, coated with gold, and examined with an FEI XL30 SEM Field Emission Gun at 5 kV with high vacuum mode using an Everhart-Thornley detector. A gaseous secondary electron detector was used with a spot size of 3, at 15 kV. The temperature was 4° C. with a chamber pressure ranging from 5 to 6 T, providing humidity up to 100% at the sample.

ITS-Based Phylogenetic Analysis

Phylogenetic analysis of the endophyte Ni25-2A was carried out by sequencing the ITS 5.8S ribosomal gene. Ni25-2A was grown on PD agar for 7 days and DNA templates were prepared by using the Prepman Ultra Sample Preparation Reagent (Applied Biosystems Inc., USA) according to the manufacturer's guidelines. Universal primer pair ITS1 (5'-TCCGTAGGTGAACCTGCGG-3'; SEQ ID NO. 1) and ITS4 (5'-TCCTCCGCTTATTGATATGC-3'; SEQ ID NO. 2) was used to amplify the 8SITS-5.8S region of the fungus by the polymerase chain reaction (PCR). The PCR conditions used were as follows: initial denaturation at 94° C. for 3 min, followed by 30 cycles of 94° C. for 15 s, 50° C. for 30 s, 72° C. for 45 s, and a final extension of 72° C. for 5 min. The 50 µl reaction mixture contained 1×PCR buffer, 200 µM each dNTP, 15 mM MgCl$_2$, 10 pmol of each primer, 1-5 ng of DNA, and 2.5 U of Taq DNA polymerase. The amplified product (5 µl) was visualized on 1% (w/v) agarose gel containing 0.5 µg/ml of ethidium bromide, to confirm the presence of a single amplified band. The amplified products were purified by Amicon Ultra columns (Millipore, USA) and 10-20 ng were used in a 10 µl sequencing reaction using the Big Dye Terminator sequencing kit (v. 3.1). The forward primer ITS1 (3.2 pmoles) was used in the cycle sequencing reaction, and 20 cycles of 96° C. for 10 s, 50° C. for 5 s, and 60° C. for 4 min were performed in a Biometra Thermocycler. The extension products were purified by ethanol precipitation, dissolved in 15 µl of HiDi Formamide, incubated at 95°

C. for 1 min, and loaded on an ABI Prism 377 Genetic Analyzer (Perkin-Elmer, USA) for sequencing.

All the reagents for sequencing were from Applied Biosystems Inc., USA. The amplified products were sequenced and aligned with the sequences in the GenBank by the BLASTN 53; program (Altschul et al., 1007, Nucleic Acids Res. 25:3389-3402). Relevant sequences were downloaded and aligned using the MegAlign software (DNASTAR, Lasergene) to construct the distance matrix. The evolutionary position of the organism was ascertained by constructing a phylogenetic tree as described previously (Tamura et al., 2007, Molec. Biol. Evol. 24:1596-1599).

GC/MS Analyses of Fungal VOCs

Qualitative analysis of the VOCs produced by Ni25-2A was carried out by the methods described previously (Strobel et al., 2001, Microbiology 147:2943-2950). The organism was grown on PD agar for 10 days in a Petri dish wrapped in a two layers of Parafilm to ensure that the VOCs produced during the entire period of growth accumulated in the headspace of the fungus. A hole was drilled on one side of the plate and a baked SPME fiber (Supelco) 50/30 divinylbenzene/carburen on polydimethylsiloxane on a stable flex fiber was inserted through it and the vapour phase was adsorbed for 45 min. The vapors were injected into a Hewlett Packard 6890 gas chromatograph containing a 30 m×0.25 mm inner diameter ZB Wax capillary column with a film thickness of 0.50 μm. A thermal program of 30° C. for 2 min followed by art increase to 220° C. at 5° C./min was applied. Ultrahigh purity helium gas was used as the carrier gas and the initial column head pressure was 50 kPa.

Data acquisition and data processing were performed on the Hewlett Packard CHEMSTATION software system. Initial identification of the compounds produced by the endophyte was made via library comparison using the National Institute of Standards and Technology (NIST) database, and all chemical compounds described elsewhere herein use the NIST database chemical terminology. The authenticity of several compounds identified by GC/MS was reconfirmed by GC/MS of authentic standards. Standard compounds were run in a comparable manner as the fungal samples.

The results of the experiments are now described.

Evolutionary Position of Ni25-2A, a *Nodulisporium* sp.

Figure 12:
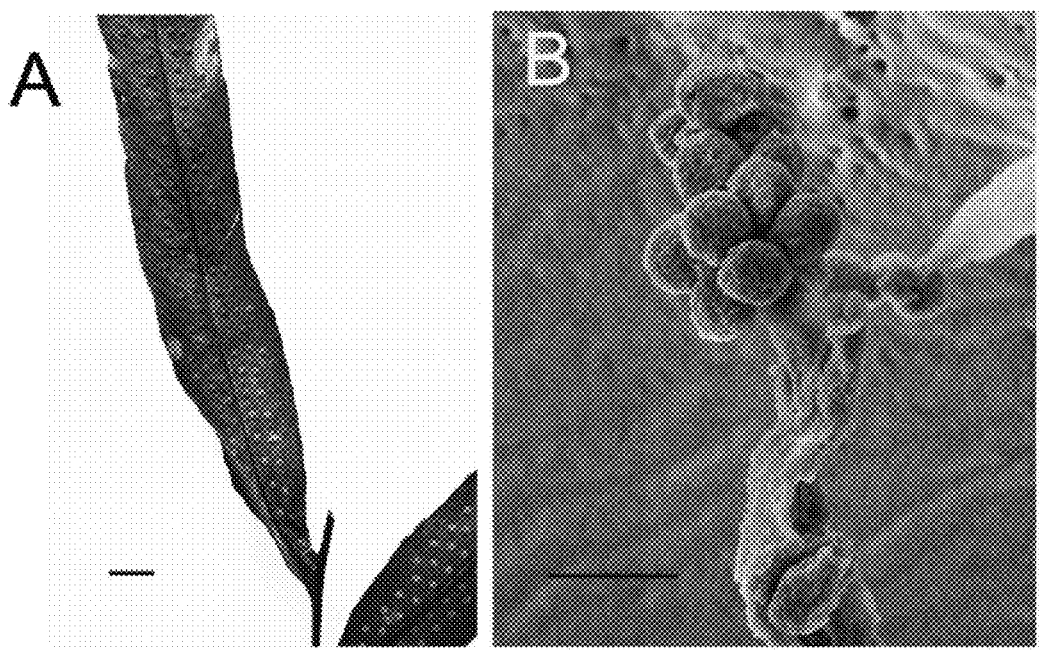
FIG. 12, comprising

The fungus (Ni25-2A) that was obtained from *Thelypteris angustifolia*, when grown on PDA, showed unique morphological characteristics (FIG. 12). The fungus colony is initially creamy white, grows grey from the middle towards the edges as it turns old, and finally becomes brownish, being circular with sharp margins and showing ridges extending from the center to the edge of the colony. Colonies more than one month old turn brownish, with concentric rings forming towards the margin. From the reverse side of the petri plate, the color changes from creamy to light brown to dark brown as the culture grows older, accompanied by heavy sporulation. The colony attains a regular size of 4.5 cm in 20 days. The culture smells strongly with a mix of earthy and fruity odors.

When grown on synthetic media containing individual sugars (sucrose, maltose, sorbitol, lactose, fructose, dextrose, starch, and cellulose), the fungus showed marked variations in cultural characteristics. The organism spreads its hyphae all over the plate in contrast to making a discrete colony with a well-defined margin as it does on PDA. The best growth was observed on maltose (153%) and the lowest on sorbitol (67%) with respect to a PDA control. On water agar and a cellulose-based medium, the growth of the organism was insignificant. The characteristic smell of the volatiles of this organism was diminished when grown on media other than PDA.

Figure 13:
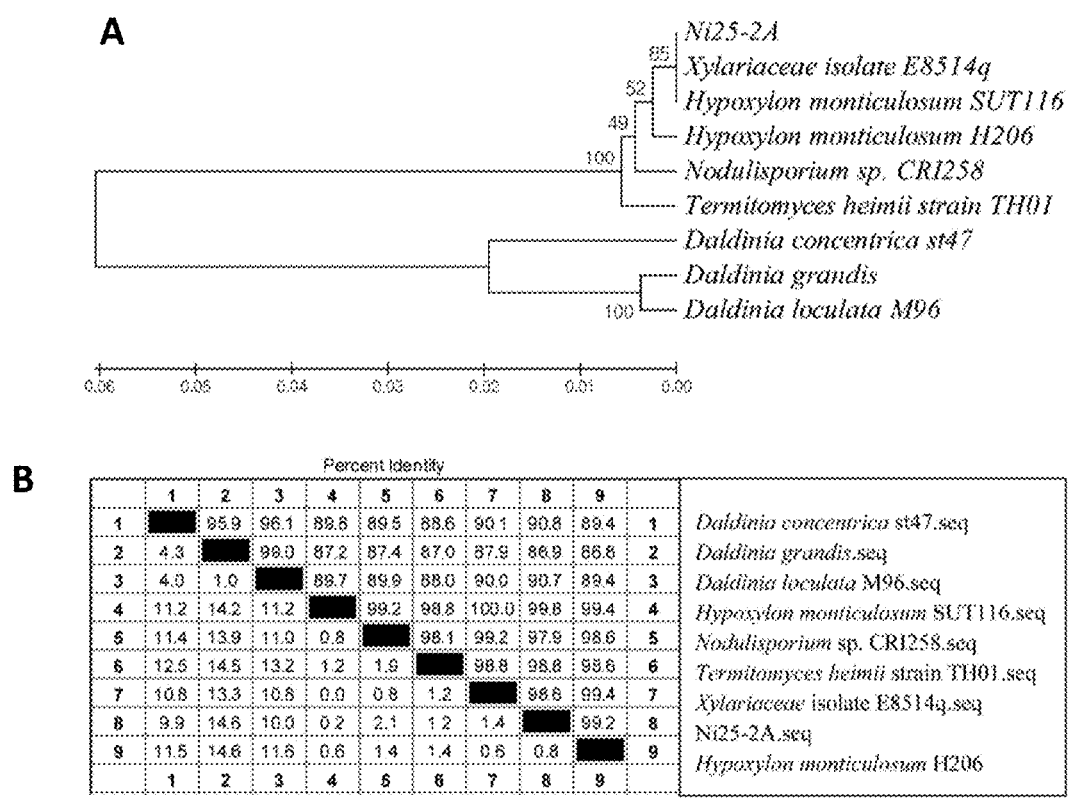
FIG. 13, comprising

Scanning electron microscopy showed an imperfect stage of Ni25-2A resembling a *Nodulisporium*-like anamorph. with 0.4-1.4 μm hyphae, 1.4-1.8×1.8-3.3 μm oval-shaped conidia, having rough surfaces and present as one-celled clusters on branched conidiophores (FIG. 12B). However, the partial 18S-ITS-5.8S ribosomal gene sequence (GenBank Accession No. JQ968613) of this organism displayed the highest sequence similarity of 99.8% and 99.2% with *Hypoxylon monticulosum* strains SUT116 and H206, respectively (FIG. 13). The organism also showed close relationship with *Nodulisporium* sp., which is the anamorphic stage of *Hypoxylon* sp. In the phylogenetic analyses, Ni25-2A and *Hypoxylon monticulosum* strains SUT116 formed a sister group with three different species of *Daldinia* (FIG. 13). However, the perfect stage of the fungus was not observed on any of the media used for its cultivation. Thus, Ni25-2A is hereafter referred to as *Nodulisporium* sp.

In Vitro Antimicrobial Activity of *Nodulisporium* sp.

In co-culture, the endophyte inhibited the growth of *Fusarium solani* and *Sclerotinia sclerotiorum* by 50% and 100%, respectively. The organism also inhibited *Candida albicans*, whereas no activity was detected against *B. subtilis* and *E. coli*. Owing to its significant antimycotic activity, the activity of its VOCs was evaluated against a panel of several pathogens (Table 9).

TABLE 9

The inhibition of test microorganisms by the VOCs of *Nodulisporium* sp. and the artificial mixture of the VOCs.

| Test organism | Percent inhibition | Viability | $IC_{50}$ of Artificial VOC mix (μl/ml of airspace) |
|---|---|---|---|
| Aspergillus fumigatus | 20.0 ± 0.0% | | 0.25 |
| Botrytis cinerea | 20 ± 0.0% | | 0.15 |
| Ceratocystis ulmi | 0.0 ± 0.0% | | 0.2 |
| Cercospora beticola | 0.0 ± 0.0% | | 0.2 |
| Colletotrichum lagenarium | 0.0 ± 0.0% | | 0.2 |
| Fusarium solani | 0.0 ± 0.0% | | 0.2 |
| Geotrichium candidum | 13.3 ± 3.5% | | 0.35 |
| Phytophthora palmivora | 100 ± 0.0% | Nonviable | 0.1 |
| Phytophthora cinnamomi | 100 ± 0.0% | Viable | 0.1 |
| Pythium ultimum | 42.9 ± 4.1% | | 0.1 |
| Rhizoctonia solani | 100 ± 0.0% | Nonviable | 0.15 |
| Sclerotinia sclerotiorum | 100 ± 0.0% | Nonviable | 0.15 |
| Trichoderma viridae | 0.0 ± 0.0% | | 0.23 |
| Verticillium dahliae | 0.0 ± 0.0% | | 0.2 |
| Muscodor albus | 33.3 ± 1.8% | | ND[a] |
| Candida albicans | No inhibition | | ND |
| Bacillus subtillus | No inhibition | | ND |
| Escherichia coli | No inhibition | | ND |

[a]ND = not determined.

The fungus was grown for 7 days on PDA on ½ of the agar medium in a Petri plate, and then the test organism was placed on the opposite side of the plate and the % inhibition, over the control, was measured at 48 h, as shown in this table. The viability of the test organisms was also tested. The $IC_{50}$ of the artificial VOC mixture calculated as described in the text.

The VOCs displayed selective antimycotic activity against *Phytophthora palmivora*, *Phytophthora cinnamomi*, *Rhizoctonia solani*, and *Sclerotinia sclerotiorum* rendering them completely inhibited and nonviable except for *Phytophthora cinnamomi* (Table 9). The other fungal pathogens that were partially inhibited included *Pythium ultimum* (43%), *Aspergillus fumigatus* (20%), *Botrytis cinerea* (20%), and *Geotrichum candidum* (13%). The VOCs, however, showed no inhibition in case of several other bacterial and fungal strains including *Candida albicans* (Table 1). The latter observation suggests that the co-culture inhibition of C. albicans must be due to a nonvolatile agar diffusible substance(s).
VOC Production The qualitative analyses of the VOCs produced by this organism were carried out after 10 days of growth on PDA. Interestingly, the most striking aspect of the analysis was the presence of a series of ketonesg, for example acetone; 2-pentanone; 3-hexanone, 4-methyl-; 2-hexanone, 4-methyl-; 3-hexanone, 2-4-dimethyl-; 5-hepten-2-one, ranging from C2 to C7 compounds along with the terpenes, 1,8-cineole and β-farnesene. In addition to these, the headspace contained several alcohols such as 1-butanol, 2-methyl-; 1-hexanol, 2-ethyl-; phenylethyl alcohol; and 2-naphthalinol, 3-methoxy-. Other VOCs in the mixture included 4-methyl-3-hexanol acetate and propionic acid, 2-methyl-, as well as the important fuel compound cyclohexane, propyl-. The percent relative areas calculated for each compound in the GC/MS analyses indicated that 1,8-cineole constituted the most abundant compound that was detected. The ketonesg collectively constituted about 25% of the total VOCs, whereas the compounds that could not be identified, thus designated here as "unknown", constituted about 39% (Table 10).

TABLE 10

The composition of VOCs in *Nodulisporium* sp. as determined by GC/MS.

| Retention time (min) | Relative area | Possible compound | MW (Da) | Quality | Relative area % |
|---|---|---|---|---|---|
| 1.95 | 0.5 | Acetone[a] | 58 | 78 | 2.39 |
| 3.87 | 0.2 | Unknown | 281 | | 0.96 |
| 4.08 | 0.3 | 2-Pentanone[a] | 86 | 72 | 1.44 |
| 6.13 | 0.4 | 3-Hexanone, 4-methyl-3- | 114 | 80 | 1.91 |
| 6.28 | 1.1 | Hexanone, 2-4-dimethyl-[a] | 128 | 83 | 5.26 |
| 6.86 | 0.1 | Unknown | 72 | | 0.48 |
| 7.22 | 1 | 2-Hexanone, 4-methyl- | 114 | 91 | 4.78 |
| 7.28 | 0.7 | Ethylbenzene[b] | 106 | 80 | 3.35 |
| 7.65 | 0.2 | Unknown | 98 | | 0.96 |
| 8.78 | 0.4 | Cyclohexane, propyl-1- | 126 | 72 | 1.91 |
| 9.75 | 1.7 | Butanol, 2-methyl-[a] | 88 | 78 | 8.13 |
| 9.37 | 2.7 | 1,8-Cineole[a] | 154 | 99 | 12.92 |
| 9.87 | 0.2 | 4-Methyl-3-hexanol acetate | 158 | 74 | 0.96 |
| 10.74 | 2 | 5-Hepten-2-one | 112 | 90 | 9.57 |
| 11.18 | 0.8 | Unknown | 172 | | 3.83 |
| 11.61 | 0.3 | Unknown | 128 | | 1.44 |
| 16.24 | 0.4 | Unknown | 170 | | 1.91 |
| 16.4 | 0.7 | Unknown | 112 | | 3.34 |
| 16.84 | 0.2 | Unknown | 180 | | 0.96 |
| 17.15 | 0.2 | 1-Hexanol, 2-ethyl | 130 | 78 | 0.96 |
| 19.51 | 0.2 | Propionic acid, 2-methyl-[a] | 88 | 86 | 0.96 |
| 19.76 | 0.3 | Unknown | 153 | | 1.44 |
| 20.03 | 0.3 | Unknown | 153 | | 1.44 |
| 20.13 | 1.1 | Unknown | 138 | | 5.26 |
| 20.77 | 1.5 | Unknown | 108 | | 7.18 |
| 20.32 | 0.2 | Unknown | 113 | | 0.96 |
| 21.66 | 0.3 | â-Farnesene[a] | 204 | 95 | 1.44 |
| 23.71 | 0.6 | Unknown | 146 | | 2.87 |
| 26.91 | 0.5 | Phenylethyl alcohol[a] | 122 | | 2.39 |
| 29.39 | 0.3 | Unknown | 94 | | 1.44 |
| 34.70 | 1 | Unknown | 124 | | 4.78 |
| 40.00 | 0.5 | 2-Naphthalinol, 3-methoxy- | 174 | 91 | 2.39 |

[a]These compounds had their identity confirmed by use of an authentic standard that was subjected to the same GC/MS conditions as the fungal preparation.
[b]Trace amounts of this compound were also found in the control PDA plate gas mixture.

IC50 of the Artificial VOC Mix

Several of the compounds that were available in the market were obtained and made into an artificial mixture prepared from 2-pentanone; 3-hexanone; 2-4-dimethyl-; 1-butanol, 2-methyl-; 1,8-cineole, propionic acid, 2-methyl-; and β-farnesene in the proportion as they appear in the GC/MS analysis of the VOCs (Table 10; see the relative abundance of the individual compounds). The artificial VOC mixture was most effective against *Phytophthora palmivora*, *Phytophthora cinnamomi*, *Pythium ultimum*, *Rhizoctonia solani*, *Sclerotinia sclerotiorum*, and *Botrytis cinerea*, with an IC50 of 0.1 µl/ml of the headspace for the former three pathogens and 0.15 µl/ml for the latter three. Interestingly, the organisms with the lowest IC50s were also some of the most sensitive to the fungal VOCs (Table 9). All the fungal pathogens tested in this study were susceptible to the artificial VOC mix, with the highest IC50 of 0.35 µl/ml for *Geotrichum candidum* (Table 9).

*Nodulisporium* sp. and VOCs

As described herein, the *Nodulisporium* sp. was found in nature associated with *Thelypteris angustifolia* as an endophyte. The fungus was resistant to the VOCs produced by a standard culture of *M. albus*, which was taken as an indication that it too could be a VOC-producing strain (Strobel et al., 2001, Microbiology 147:2943-2950). This organism was placed as a *Nodulisporium/Hypoxylon* on the basis of its morphological characteristics and ITS sequence analysis, although the perfect stage of this fungus was not observed under the conditions used for its cultivation.

The VOCs produced by this organism showed differential antimycotic activities, being highly active against *Phytophthora palmivora*, *Phytophthora cinnamomi*, *Rhizoctonia solani*, and *Sclerotinia sclerotiorum*, and moderately or weakly active against *Pythium ultimum*, *Aspergillus fumigatus*, *Botrytis cinerea*, and *Geotrichum candidum* (Table 9). The artificial VOC mix significantly mimicked the VOC activity of the endophyte, but the unknown compounds may also have a role in inhibiting other organisms that obviously could not be evaluated (Table 9). The selective activity of the VOCs of this organism may be exploited for inhibition of specific phytopathogens for disease management of agricultural crops. However, it is imperative to learn if this organism can act as a phytopathogen in the crop of interest. Volatile organic compounds are important infochemicals and various fungi produce interesting arrays of compounds that inhibit other microorganisms.

Among the VOCs of *Nodulisporium* sp. is a vast range of compounds that have fuel potential (mycodiesel) (M/lends et al., 2012, J. Petrol. Environ. Biotechnol. 3:3; Riyaz-Ul-Hassan et al., 2012, Microbiology 158:465-473; Strobel et al., 2008; Microbiology 154:3319-3328; Tomsheck et al., 2010, Microbial. Ecol. 60:903-914). Comparable to the endophyte, also identified as *Hypoxylon* sp. (*Nodulisporium* sp.), this organism also produces 1,8-cineole and a cyclohexane derivative (cyclohexane, propyl-) (Tomsheck et al., 2010, Microbial. Ecol. 60:903-914). The latter is also present in petroleum distillate and the former could be an excellent fuel additive (Barton and Tjandra, 1989, Fuel 68:11-17). β-Farnesene is an important fuel candidate, as its fully reduced form is being pursued as an alternate biofuel (Renniger and McPhee, 2008, U.S. Pat. No. 7,399,323).

The uniqueness of this organism is the production of short-chain ketonesg, which are the oxidized forms of many straight-chain alkanes and branched alkanes present in crude oil, in addition, a series of alcohols produced by this endophyte are also fuel-like compounds produced by fungi (Table 10). Although not wishing to be bound to any particular theory, with data accumulating on fuel-like compounds produced by microorganisms, the theory that microorganisms may have played a role in the production of crude oil seems increasingly likely (Mends et al., 2012, J. Petrol. Environ. Biotechnol. 3:3; Riyaz-Ul-Hassan et al., 2012, Microbiology 158:465-473). Although not wishing to be bound to any particular theory, it is quite possible that heat and the reductive conditions found in the earth could have been responsible for further conversion of the more oxidized fungal products (i.e., ketonesg, alkyl alcohols, and aldehydes) to the more reduced chemical forms, the hydrocarbons (Mends et al., 2012, J. Petrol. Environ. Biotechnol. 3:3). The limitation for practical applications of these fungal VOCs is the relatively low production of these substances by fungi. However, with the intervention of metabolic pathway engineering and fermentation technology, it seems that these fuel-like compounds could be produced on a large scale in the future. In nature, these compounds may be helping the host plant in evading infection from other microorganisms. β-Farnesene may be also playing a role as an insect repellent, preventing infestation of the host by aphids (Yu et al., 2012, J. Int. Plant. Biol. 54:282-299). Thus, the process of natural selection may promote the association of such endophytes with the host plants.

The *Nodulisporium* sp. described herein produces a unique and wide range of bioactive VOCs that also possess fuel potential. The use of molecular biology tools such as epigenetic modulation could be used to further explore the hidden VOC-producing potential of this organism (Riyaz-Ul-Hassan et al., 2008, Microbiology 158:465-473). Such organisms may also be selected as candidates for metabolic engineering and scale-up processes for the production of cost-effective alternate fuels or to find biological utilities.

Example 4

An Endophytic *Nodulisporium* sp. Producing Volatile Organic Compounds Having Bioactivity and Fuel Potential Described here in the isolation of *Nodulisporium* sp. as an endophyte of *Myroxylon balsamum* found in the upper Napo region of the Ecuadorian Amazon. This organism produces volatile organic compounds (VOCs) that have both fuel and biological potential. Under microaerophilic growth environments, the organism produces 1,4-cyclohexadiene, 1-methyl-, 1-4 pentadiene and cyclohexene, 1-methyl-4-(1-methylethenyl)- along with some alcohols and terpenoids of interest as potential fuels. The fungus was scaled up in an aerated large fermentation flask, and the VOCs trapped by Carbotrap technology and analyzed by headspace solid-phase microextraction (SPME) fiber-GC/MS. Under these conditions, *Nodulisporium* sp. produces a series of alkyl alcohols starting with 1-butanol-3-methyl, 1-propanol-2-methyl, 1-pentanol, 1-hexanol, 1-heptanol, 1-octanol, 1-nonanol along with phenylethyl alcohol. The organism also produces secondary alkyl alcohols, esters, ketonesg, benzene derivatives, a few terpenoids, and some hydrocarbons. It appears that many of the products have fuel potential. Furthermore, the VOCs of *Nodulisporium* sp. were active against a number of pathogens causing death to both *Aspergillus fumigatus* and *Rhizoctonia solani* and severe growth inhibition produced in *Phytophthora cinnamomi* and *Sclerotinia sclerotiorum* within 48 hr of exposure. The Carbotrapped materials somewhat mimicked the bioactivities of the culture itself when certain test organisms were exposed to these VOCs.

The materials and methods employed in these experiments are now described.

Isolating Endophytes

A search for new VOC producing endophytes was conducted in the Napo river region of the upper Amazon in Ecuador. At least 20 plants were obtained by clipping terminal stem pieces (ca. 1×20 cm) from readily accessible portions of sample trees in a relatively small area of the jungle. The harvested specimens were kept cool and as soon as possible, the stems were surface treated and internal tissue pieces were set out on plates of water agar (WA) and glycerol-arginine medium (GAM) (Tomsheck et al., 2010, Microb. Ecol. 60:903-914). The tissue pieces were incubated at room temperature for several days. Visible fungal growth from the tissue samples were picked as hyphal tips and sub-cultured and transferred to potato dextrose agar (PDA) plates. An endophyte of interest was designated EC-12 and was obtained from a ca. 10 m tall leguminous tree-Myroxylon balsamum in the area of S 0.00° 29' 960 and W 76° 22'342. This particular organism was not observed as an endophyte associated with any of the other plants that were sampled in this general area. The organism, EC-12, was stored at −70° C. as No. 2385 in the Mycological Collection of the Department of Plant Sciences at Montana State University. Long term storage of these rainforest endophytes is best done on doubly autoclaved, thoroughly wetted, and leached barley seeds.

Scanning Electron Microscopy

Scanning electron microscopy (SEM) was performed on EC-12 in order to acquire morphological data. The fungus was grown on γ-irradiated carnation leaves for 3 weeks and then the samples were slowly dehydrated in ethanol, critically point dried, coated with gold and examined with an FE XL30 SEM-FEG with high vacuum mode using an Everhart-Thornley detector (Tomsheck et al., 2010, Microb. Ecol. 60:903-914).

ITS Based Phylogenetic Analysis

Phylogenetic analysis of EC-12 was carried out by the acquisition of the ITS-5.8 S ribosomal gene sequence. The fungus was grown on PDA for 7 days and DNA templates were prepared by using the Prepman Ultra Sample Preparation Reagent according to the manufacturer's guidelines (Applied Biosystems, USA). The ITS regions of the fungus were amplified with the universal ITS primers ITS1 (5' TCCG-TAGGTGAACCTGCGG 3'; SEQ ID NO 1) and ITS4 (5' TCCTCCGCTTATTGATATGC 3'; SEQ ID NO 2) using the polymerase chain reaction (PCR). The PCR conditions used were as follows: initial denaturation at 94° C. for 3 min followed by 30 cycles of 94° C. for 15 sec., 50 C for 30 sec., 72° C. for 45 sec., and a final extension at 72° C. for 5 min. The 50 µl reaction mixture contained 1×PCR buffer, 200 µM each dNTP, 1.5 mM MgCl$_2$, 10 pmol of each primer, 1-5 ng of extracted DNA and 2.5 U of Taq DNA polymerase.

The amplified product (5 µl) was visualized on 1% (w/v) agarose gel to confirm the presence of a single amplified band. The amplified products were purified by Amicon Ultra columns (Millipore, USA) and 20-40 ng were used in a 10 µl sequencing reaction using the Big Dye Terminator sequencing kit (v. 3.1), with 2 pmoles of the forward or the reverse primer in the cycle sequencing reaction. Twenty cycles of 96° C. for 10 sec, 50° C. for 5 sec and 60° C. for 4 min were performed and the extension products were purified by ethanol precipitation, dissolved in 10 µl of HiDi Formamide, incubated at 95° C. for 1 min and loaded on ABI Prism 377 Genetic Analyzer (Perkin-Elmer, USA) for sequencing. All the reagents for sequencing were from Applied Biosystems, USA. The DNA sequence was aligned with the reference sequences in GenBank by BLASTN program (Altschul et al., 1997, Nucleic Acids Res. 25:3389-3402). Relevant sequences were downloaded and a phylogenetic tree was constructed as previously described (Tamura et al., 2007, Mol. Biol. Evol. 24:1596-1599). The GenBank Accession number for the ITS sequence of this organism is -JQ424940.

Carbotrap Experiments

In order to obtain quantitative weight measurements on the VOC production of this fungus and also to learn what VOCs are made under conditions of near optimum aeration, it was grown in 7 L of PD broth in a 10 L flask for 14 days, 200 rpm at 22° C. The culture had an inflow of compressed air at 800 ml/min per minute through a 20 μm filter. The flask outlet was connected to a custom designed stainless steel column containing Carbotrap materials (Supelco-Carbotraps A and B) specifically designed for trapping hydrocarbons and hydrocarbon derivatives) for adsorption of the fungal culture VOCs starting at day 4 to the end of the fermentation period (Booth et al., 2011, Biotechnol. Lett. 33:1963-1972; see also U.S. patent application Ser. No. 13/591,968).

Eventually, the compounds in the Carbotrap column were desorbed by heating in a programmable oven, purged with a flow of nitrogen gas, followed by passage of the effluent in a tube cooled with liquid nitrogen (Booth et al., 2011, Biotechnol. Lett, 33:1963-1972; see also U.S. patent application Ser. No. 13/591,968). Gravimetric analysis provided information on VOC yields. The efficiency of the column trapping method ranges from 65-70%. In addition, the gas trapping vial, having a septum, was gently warmed and thus directly prepared for qualitative GC/MS gas analysis. The trapped liquid compounds were also used in bioassay tests. The dry weight of the fungal mass was determined after centrifugation and drying of the insolubles found at the end of the incubation period, Bioactivities of EC-12

The volatiles produced by a 13 day old culture (optimum time) of EC-12 were tested for antimicrobial activity against selected pathogenic fungi according to a VOC bioassay test system previously described for analysis of VOCs produced by *Muscodor albus* (Strobel et al., 2001, Microbiology 147: 2943-2950). The assays were conducted by growing the test organism on one side (half moon) of a Petri plate (on PDA) and then placing a small plug of each test fungus (a 3 mm plug) on the opposite side of the plate (half moon) of a PDA plate. The plate was then wrapped with Parafilm and incubated at 23° C. for varying time periods. Growth of the filamentous test fungi was quantitatively assessed by making multiple measurements of growth extending from the edge of the inoculum plugs comparable to corresponding controls after several days as described previously (Strobel et al., 2001, Microbiology 147:2943-2950). On the other hand, the Carbotrapped VOCs were recovered from the trapping tube and assayed according to the methods described by Strobel when testing the artificial mixtures of VOCs produced by *M. albus* (Strobel et al., 2001, Microbiology 147:2943-2950). The test mixture is transferred to a small plastic cup and placed in the center of a Petri plate (PDA) surrounded by small plugs of test organisms and the growth of the test organisms measured after appropriate exposure times. All test organisms were obtained from the Mycological Collection, Department of Plant Sciences, Montana State University.

GC/MS Analyses

In order to determine the composition of the VOCs under microaerophilic conditions, the fungus was grown in 60 ml of PD broth for 7 days in a sealed 250 ml Erylenmeyer flask, with constant agitation at 22° C. The volatiles were sampled from the headspace of the fungal cultures after days. Briefly, a small hole was drilled in the cap and a preconditioned "Solid Phase Micro Extraction (SPME) fiber" coated with DVB/CAR/PDMS was inserted and the fiber exposed for 5 min. The VOCs bound to the fiber were desorbed for 3 min in a split-/splitless injector (splitless mode, 250° C.) of a Varian 3800 gas chromatograph coupled with an ion trap mass spectrometer attached to a DB5-HT (30 m×0.25 mm×0.25 um). Helium was used as carrier gas at constant flow rate 1 ml/min. The oven program was 30° C. (hold 3 min), 5 C/min to 220° C., 10 C/min to 250° C. (hold 5 min). The MSD parameters were EI at 70 eV, mass range was 30-500 Da, and the scan speed was 2 scans/sec. Headspace SPME-GC/MS was performed on replicate EC-12 PD broth as well as PD agar cultures.

Qualitative gas analysis of the compounds desorbed from the stainless steel Carbotrap (trapping tube) was done on a preconditioned 50/30DVB/CAR/PDMSSPME fiber for 5 min after the tube was gently warmed to volatilize the trapped liquid (Booth et al., 2011, Biotechnol. Lett. 33:1963-1972; see also U.S. patent application Ser. No. 13/591,968). The syringe was then inserted into the splitless injection port of a Hewlett Packard 6890 gas chromatograph containing a 30 m×0.25 mm I.D. ZB Wax capillary column with a film thickness of 0.50 μm. The column was temperature programmed as follows: 30° C. for 2 min increased to 220° C. at 5° C. $min^{-1}$. The carrier gas was ultra high purity helium, and the initial column head pressure was 50 kPa. A 30 sec injection time was used to introduce the sample fiber into the GC. The gas chromatograph was interfaced to a Hewlett Packard 5973 mass selective detector (mass spectrometer) operating at unit resolution. The MS was scanned at a rate of 2.5 scans per second over a mass range of 35-360 amu. Data acquisition and data processing were performed on the Hewlett Packard ChemStation software system.

In all cases, tentative identification of the fungal compounds was made via library comparison using the NIST 2011 (US-National Institute of Standards and Technology) mass spectral library and all chemical compounds described in this report use the NIST data base chemical terminology. Only compounds, having a quality match score better than 70%, are listed and described in this report. Peak areas for all other unidentified compounds were lumped and summed for each EC-12 culture tested. Compounds appearing in the control flasks, plates, or tubes were removed from the analysis.

The results of the experiments are now described.

Figure 14:
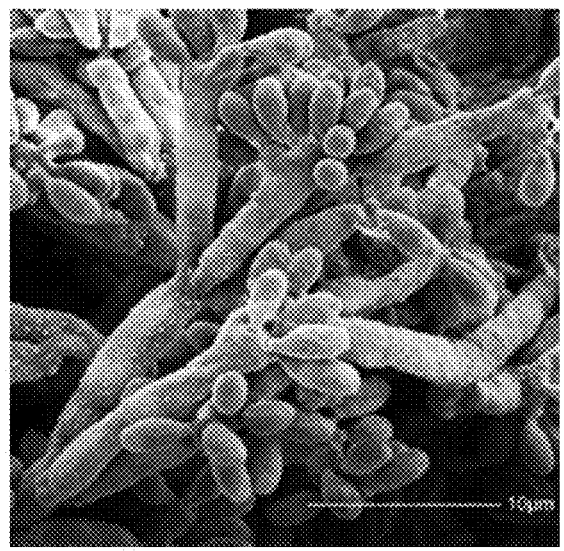
FIG. 14 is a photograph of the *Nodulisporium* sp. or imperfect stage of EC-12 (*Nodulisporium* sp.) as seen by SEM. Note the conidiophores bearing numerous conidia.
Figure 15:
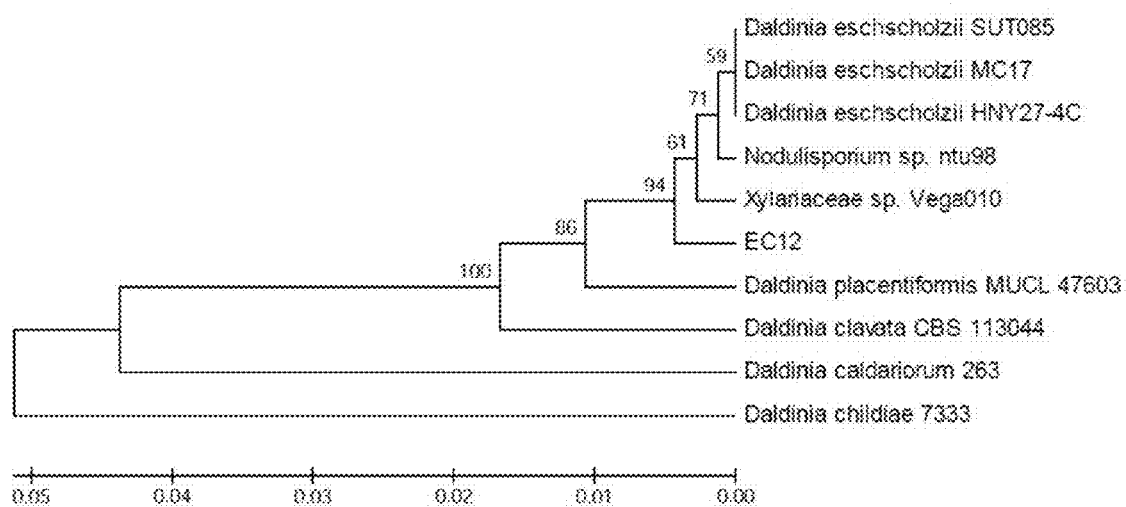
FIG. 15 is a phylogenetic tree, depicting the evolutionary position of the endophyte EC12, constructed using the UPGMA method (Griffin et al., 2010, Microbiology 156: 3814-3829). The percentage of replicate trees in which the associated taxa clustered together in the bootstrap test (500 replicates) is shown next to the branches (Strobel, 2006, Curr. Opin. Microbiol. 9:240-244). The tree is drawn to scale, with branch lengths in the same units as those of the evolutionary distances used to infer the phylogenetic tree. The evolutionary distances were computed using the Maximum Composite Likelihood method as previously described (Tamura et al., 2007, Mol. Biol. Evol. 24:1596-1599) and are in the units of the number of base substitutions per site. All positions containing gaps and missing data were eliminated from the dataset (Complete deletion option).

The endophytic organism EC-12, by light and scanning electron microscopy produced an imperfect stage resembling that of *Nodulisporium* sp. (FIG. 14). The organism when grown on PDA (2 week old culture) produced whitish felt-like mycelia on the 4 cm periphery of the culture. On the other hand, the center of the culture was a distinctively greyish/brown coloration. The reverse side of the plate, after 2 weeks, was totally brownish/black. The mycelium produced erect to suberect, branching conidiophores with slender conidiogenous cells attached in irregular to verticillate patterns. Conidiogenous cells terminated in clusters of one-celled conidia at the apical end. The conidia (1.81±0.6×3.75±0.3 μm), as viewed by SEM, were clavateellipsoid with truncated ends, but by regular light microscopy they appeared more ellipsoidal. Evidence of successional budding was seen as bud scars on conidiogenous cells (FIG. 14). In all respects the fungus totally resembled *Nodulisporium* sp., (Hanlin, 1997, in Illustrated Genera of Ascomycetes. Am. Phytopath Press, St. Paul, Mn.). However, the 18S-ITS-5.8S of the organism showed 99% sequence similarity with *Daldinia escholzii* which is the most likely the perfect stage for this organism even though it was never observed and *D. escholzii* has *Nodulisporium* sp. as its imperfect stage (Hanlin, 1997, in Illustrated Genera of Ascomycetes. Am. Phytopath Press, St. Paul, Mn.) (FIG. 15). Multiple substrates were tested for varying lengths of time in order to observe the perfect stage but to no avail.

Composition of the VOCs Produced by *Nodulisporium* sp.

When *Nodulisporium* sp. was originally isolated, a 7-10 day old culture possessed a distinctive but pleasant odor. This observation necessitated a closer chemical identification of the VOCs being made by this organism under varying conditions of growth. The potential fuel compounds that could be consistently matched, in repeated experiments and on a qualitative basis, were 1,4-cyclohexadiene, 1-methyl-, 1-4 pentadiene and cyclohexene, 1-methyl-4-(1-methylethenyl)-, but other volatile compounds of interest were also produced (Table 11).

TABLE 11

The VOC composition of Nodulisporium sp. flask analyzed at 7 days of growth by Headspace SPME-GC/MS on three different cultures each grown on PD broth.

| Retention Time (min) | *% Area-PD1 | % Area-PD2 | % Area-PD3 | Possible Compound | Molecular Weight (g/mol) | Quality Match |
|---|---|---|---|---|---|---|
| 5.4 | 26 | 18.7 | 17.4 | 1-Pentanol or 1-Butanol, 3-methyl- | 88 | 72 |
| 6.8 | 1 | 28.3 | 32.6 | 1,4-Cyclohexadiene, 1-methyl- | 94 | 91 |
| 10.6 | 21 | 2 | 0.5 | Oxime-, methoxy-phenyl- | 151 | 82 |
| 11.1 | 1.7 | 6 | 10 | 1,4-Pentadiene | 68 | 77 |
| 14.9 | nd | 1.9 | 1.4 | Cyclohexene, 1-methyl-4-(1-methylethanyl)- | 136 | 85 |
| 15.1 | 0.6 | nd | 0.7 | Eucalyptol | 154 | 79 |
| 16.5 | nd | 1.4 | 0.5 | 3-Heptanone, 5-ethyl-4-methyl- | 156 | 75 |
| 17.6 | 14.3 | 8.9 | 9.3 | Phenylethyl Alcohol | 122 | 94 |
| 21.1 | nd | 0.3 | 0.2 | Benzothiazole | 135 | 91 |
| 25.5 | 1.6 | 1.1 | 2.3 | β-Elamene | 204 | 83 |
| 26.7 | 1 | 1 | 1.1 | α-Gualene | 204 | 86 |
| 27.7 | 5.6 | 7.6 | 3.4 | 2H-1-Benzopyran-2-one, 4,7-dihydroxy- | 178 | 76 |
| 28.1 | 0.7 | 0.3 | 0.5 | Chamigrene | 204 | 75 |
| 28.4 | 4 | 2.6 | 4.9 | Azulene, 1,2,3,5,6,7,8,8a-octahydro-1,4-dimethyl-7-(1-methylethenyl)-(aka Guaia-1(10)-11-diene) | 204 | 85 |
| 32 | 11.5 | 1.9 | 2 | Azulene, 1,2,3,3a,4,5,6,7-octahydro-1,4-dimethyl-7-(1-methylethenyl)-(aka γ-Gurjunene) | 204 | 84 |
| 32.1 | nd | nd | 4.8 | 2-Naphthalenol, 3-methoxy- | 174 | 73 |
| — | 11.3 | 17.9 | 7.9 | Remaining unknown compounds | — | <70 |

*% Area is given as the area of the peak of interest over total area of peaks in chromatogram (from 3 replicate EC-12 cultures grown in potato dextrose (PD1-PD3)). Only compounds with quality match scores >70 are listed. Area of unassigned peaks are summed and listed as unknown compounds. Compounds also observed in PD broth control are italicized, (nd) = not detected. Details of VOC extraction and GC/MS analysis are described else where herein. The mycelial dry weight per culture is ca. 0.2 g.

However, the quantities of individual components in three separate analyses, using the SPME fiber technique, were not greatly consistent due to the inherent limitations of the SPME fiber technique but qualitatively they were almost identical (Table 11). Interestingly, the cyclohexanes as well as pentane and its derivatives constitute some of the major groups of hydrocarbons in diesel fuels as analyzed by the SPME technique. However, the compounds in greatest abundance in the fungal VOCs were 1-butanol-3 methyl (and or 1 pentanol), and phenylethyl alcohol which also have fuel potential (Table 11). Also, present in the analysis were a series of terpenoids including naphthene and azulene derivatives (Table 11). Similar data were obtained when SPME analyses were conducted on Nodulisporium sp. grown on PDA plates. However, differences were noted only in the relative amounts of the VOCs that were detected. It is to be noted that many of the VOCs in the mixture could not have their identities assigned since the percentage match was low. Although not wishing to be bound to any particular theory, this may be the result of low concentrations of compounds present (detection limits) and/or perhaps interference with high amounts of other compounds. Further serial transfers of the organism resulted in a change of odor as well as detectable changes in the production of VOCs.

In both SPME analyses of plate and liquid culture analyses there were limited detectable numbers of VOCs produced by Nodulisporium sp. This may be the result of sampling being done in only a short time frame and scale. Thus, in order to get a more complete picture of what the potential might be for this fungus to make fuel potential compounds, a 10 L flask equipped with a stainless steel column having Carbotrap materials A&B was attached to the outflow of the flask for the majority of the incubation period. The hydrocarbons and related compounds were desorbed from the Carbotrap materials and collected in a cooled tube (liquid nitrogen). The amount of material collected was 19.0 mg.

The SPME-GC/MS analysis of the VOCs trapped by the Carbotraps yielded a plethora of hydrocarbon derivatives (Table 12). Again, the most abundant substances detected were phenylethyl alcohol and 1-butanol-3-methyl which is comparable to that found in the smaller flasks (Table 12). Also, it appears that the most, but not all of the compounds present in the trapping tube could detected and identified by this method (Table 12). Thus, the increased numbers of VOCs in the Carbotrapped compounds is likely related to the increased amounts of each component.

Table 12: GC/MS for liquid collected from the Carbotrap extraction of Nodulisporium sp. produced by 21.5 g dry weight of fungal hyphae over a 2 week period.

TABLE 12

GC/MS for liquid collected from the Carbotrap extraction of Nodulisporium sp. produced by 21.5 g dry weight of fungal hyphae over a 2 week period.

| Retention Time (min) | Relative Abundance | Possible Compound | Molecular Weight | Quality |
|---|---|---|---|---|
| 6.44 | 0.212 | Heptane, 5-ethyl-2,2,3-trimethyl- | 170 | 78 |
| 8.06 | 0.353 | Tetradecane | 198 | 90 |
| 8.34 | 0.337 | 1-Propanol, 2-methyl- | 74 | 80 |
| 9.14 | 2.43 | 1-Butanol, 3-methyl, acetate | 130 | 86 |
| 9.21 | 0.48 | 4-Heptanone | 114 | 78 |
| 10.13 | 1.938 | Butanoic acid, 2-methylpropyl ester | 144 | 90 |

TABLE 12-continued

GC/MS for liquid collected from the Carbotrap extraction of *Nodulisporium* sp. produced by 21.5 g dry weight of fungal *hyphae* over a 2 week period.

| Retention Time (min) | Relative Abundance | Possible Compound | Molecular Weight | Quality |
|---|---|---|---|---|
| 11.07 | 0.347 | Tridecane | 184 | 86 |
| 11.78 | 32.624 | 1-Butanol, 3-methyl- | 88 | 83 |
| 11.92 | 0.194 | Butanoic acid, butyl ester | 144 | 72 |
| 12.08 | 0.195 | Benzene, 1-ethyl-3-methyl- | 120 | 80 |
| 12.29 | 0.896 | Hexanoic acid, ethyl ester | 144 | 97 |
| 12.66 | 0.2 | Benzene, 1,2,4-trimethyl- | 120 | 95 |
| 12.77 | 0.265 | 1-Pentanol | 88 | 83 |
| 13.17 | 5.047 | Butanoic acid, 3-methylbutyl ester | 158 | 90 |
| 13.31 | 0.823 | 4-Hexen-3-one, 4-methyl- | 112 | 90 |
| 14.24 | 0.631 | 3-Hepten-2-one, (Z)- | 112 | 80 |
| 14.54 | 0.258 | 1-Pentanol, 4-methyl- | 102 | 72 |
| 14.64 | 0.254 | 2-Heptanol | 116 | 83 |
| 14.86 | 1.614 | 4-Nonanone | 142 | 91 |
| 15.61 | 2.355 | 1-Hexanol | 102 | 83 |
| 15.85 | 0.191 | Benzene, 1,2,4,5-tetramethyl- | 134 | 76 |
| 17.02 | 3.139 | 3-(1-Methylpropy1)-2-hydroxy-2-cyclopenten-1-one | 154 | 72 |
| 17.17 | 1.784 | 1-Nonanol | 144 | 72 |
| 18.17 | 0.395 | 1-Octen-3-ol | 128 | 72 |
| 18.3 | 0.77 | Heptanol | 116 | 90 |
| 18.53 | 3.135 | dl-6-Methyl-5-hepten-2-ol | 128 | 95 |
| 18.86 | 0.239 | 4-Nonanol | 144 | 86 |
| 19.8 | 0.368 | 2,4-Heptandienal, 2,4-dimethyl- | 138 | 72 |
| 20.06 | 0.261 | Bicyclo[2.2.1]heptan-2-one, 1,7,7-trimethyl-, (1R)- | 152 | 97 |
| 20.63 | 0.255 | 2,3-Butanediol | 90 | 80 |
| 20.91 | 1.805 | 1-Octanol | 130 | 91 |
| 21.54 | 0.681 | 2,3-Butanediol, [R-(R*,R*)]- | 90 | 86 |
| 21.71 | 1.653 | 1,5-Cyclodecadiene, 1,5-dimethyl-8-(1-methylethylidene)-, (e,e)- | 204 | 90 |
| 21.91 | 0.287 | Caryophyllene | 204 | 99 |
| 22.36 | 0.215 | Cycloprop[a]indene, 1,1a,6,6a-tetrahydro- | 130 | 95 |
| 25.82 | 0.257 | Benzenemethanol, .alpha.,.alpha.-dimethyl- | 136 | 90 |
| 26.51 | 0.254 | Acetic acid, 2-phenylethyl ester | 164 | 83 |
| 27.08 | 0.593 | Acetic acid, 2-phenylethyl ester | 164 | 90 |
| 28.48 | 0.204 | Benzyl Alcohol | 108 | 98 |
| 29.33 | 30.999 | Phenylethyl Alcohol | 122 | 93 |
| 30.24 | 0.193 | Benzothiazole | 135 | 81 |
| — | 44.924 | Remaining unknown compounds | — | <70 |
| Overall Abundance | 144.056 | | | |

Most interestingly, in the analyses, was the presence of a complete series of straight chained alkyl alcohols starting with 1-pentanol through 1-nonanol. Hydrocarbon components such as tridecane and tetradecane along with various methylated benzenes were found in this analysis (Table 12). A clear common theme in analysis of the mixture is the presence of a series of alkyl esters of small molecular weight carboxylic acids, especially butanoic and hexanoic acids, as well as a series of alkyl ketonesg including 4-nonanone and 3-hepten-2-one. Interestingly, none of the terpenoids and the oxime produced by the fungus in the microaerophilic environment was present in the large flask (Tables 11 and 12). However one sesquiterpenoid (caryophyllene) was present but was not found in the smaller fermentation flasks (Tables 11 and 12). In addition, also absent in the large flask were the cyclohexene and cyclohexadiene derivatives (Tables 11 and 12), but several highly branched hydrocarbons were noted including heptane, 5-ethyl-2,2,3-trimethyl- and a cyclodecadiene derivative (Table 12). The incorporation of nitrogen and sulfur into the VOC stream (via such compounds as oximes and thiazoles) is undesirable for fuel use. Therefore, overall, it appears that almost the entire mixture of VOCs produced by this fungus has fuel potential. The scope of the VOC stream may potentially be tailored for particular combustion applications.

Since *Nodulisporium* sp. was making a plethora of VOCs it was deemed important to determine the biological role of these gases. A simple split plate test was done on 13 day old cultures of *Nodulisporium* sp. The results showed that the VOCs of the fungus were active against a wide range of plant pathogenic fungi (Table 13). *Rhizoctonia solani* and *A. flavus* were most sensitive to the VOCs of *Nodulisporium* sp. with death resulting for only a 48 hr exposure time (Table 13). Both *Phytophthora* spp. as well as *S. sclerotiorum* were also sensitive to the VOCs but were not killed by them. However, others including *P. ultimum, V. dahliae* and *F. solani* were unaffected during the time course of the experiment (Table 13).

TABLE 13

Effects of a 13-day-old colony of *Nodulisporium* sp. on various fungi in a simple split plate test

| Test Organism | Percent Inhibition | Dead (D) or Alive (A) |
| --- | --- | --- |
| *Aspergillus flavus* | 100.00% ± 0.00 | D |
| *Botrytis cinerea* | 27.10% ± 0.49 | A |
| *Colletotrichum lagenarium* | 39.90% ± 0.20 | A |
| *Ceratocystis ulmi* | 23.80% ± 0.03 | A |
| *Cercospora beticola* | 10.80% ± 0.10 | A |
| *Fusarium solani* | −0.40% ± 0.06 | A |
| *Geotrichium candidum* | −7.10% ± 0.01 | A |
| *Phytophthora palmivora* | 56.90% ± 0.18 | A |
| *Phytophthora cinnamomi* | 73.40% ± 0.04 | A |
| *Pythium ultimum* | −4.40% ± 0.15 | A |
| *Rhizoctonia solani* | 100.00% ± 0.00 | D |
| *Sclerotinia sclerotiorum* | 79.20% ± 0.18 | A |
| *Trichoderma viridae* | 47.70% ± 0.67 | A |
| *Verticillium dahliae* | −12.70% ± 0.04 | A |

Viability was measured after 48 hr of exposure to the fungal VOCs. Inhibition was measured after a 48 hr exposure to the *Nodulisporium* sp. VOCs.

This is in sharp contrast to the sensitivities of these same fungi to the VOCs of *M. albus* where in *P. ultimum* and the *Phytophthora* spp. are some of the most sensitive fungi to these volatiles (Strobel et al., 2001, Microbiology 147:2943-2950). Although not wishing to be bound to any particular theory, this suggests that the chemistry of the volatiles is different and that there are different targets within the test fungi for sensitivity to various VOCs. This is probably the case since many of the VOCs reported for *M. albus* are not present in *Nodulisporium* sp. and vice versa (Tables 11 and 12) (Strobel et al., 2001, Microbiology 147:2943-2950).

Since the VOCs of *Nodulisporium* sp. could be recovered by the Carbotrap technology, they too were subjected to a bioassay test utilizing several select plant pathogens (Table 14). A small amount (0.4 mg) of the collected VOCs of *Nodulisporium* sp., in the form of a liquid, when placed in the plastic cup assay system, as elsewhere herein, produced some inhibition of the same target organisms as observed in the inhibition experiments with *Nodulisporium* sp. itself. (Table 13).

TABLE 14

Effects of liquid volatile compounds collected from a 13-day-old colony of *Nodulisporium* sp. on various fungi as conducted in a well assay on a Petri plate with PDA

| Test Organism | Percent Inhibition | Dead (D) or Alive (A) |
| --- | --- | --- |
| *Aspergillus fumigatus* | 3.4% ± 0.02 | A |
| *Geotrichium candidum* | 4.6% ± 0.02 | A |
| *Phytophthora cinnamomi* | −29.6% ± 0.12 | A |
| *Rhizoctonia solani* | 21.2% ± 0.10 | A |
| *Sclerotinia sclerotiorum* | 5.2% ± 0.24 | A |
| *Verticillium dahliae* | −8.4% ± 0.09 | A |

Namely, the liquid mixture yielded the greatest inhibition response from *R. solani* and *S. sclerotiorum* but with somewhat mixed results from the other test organisms (Table 14). This appears to be the first report where by fungal VOCs have been trapped and reconstituted in bioassay tests. Although not wishing to be bound to any particular theory, the decrease in the relative bioactivity may be related to the small amount of materials tested, a loss of one or more critical bioactivity compounds, or the lability of certain components that are necessary for bioactivity.

*Nodulisporium* sp. and VOCs

The fungal isolate used in this study was obtained as an endophyte from the upper Amazon basin. The organism, by virtue of its molecular sequence data and its morphology best fits the description of a *Nodulisporium* sp. with a *Daldinia* sp. as its most likely perfect stage (FIGS. 14 and 15). This isolate of *Nodulisporium* sp. produces a series of VOCs many of which are hydrocarbons or hydrocarbon derivatives (Tables 11 and 12). The composition of VOCs seems to be related to the conditions under which the fungus is grown (Tables 11 and 12). For instance, the cyclohexene derivatives are consistently produced when the organism has been grown on a solid medium or under microaerophilic conditions (Table 11). The organism, when grown on PD broth in a larger scale and under continuous aeration produced a plethora of alkyl alcohols, esters, and ketonesg (Table 12). These compounds by themselves, with a few exceptions, are potential fuels and further work on optimizing production should be pursued.

It is to be noted in this study, that in both types of fermentation, representative VOCs were produced in each that perfectly or closely match each of the major classes of molecules found in petroleum distillate (diesel) (Tables 11 and 12). In some cases, the specific VOC may be only one or two reductive steps away from the product actually found in diesel such as the cyclohexenes or the series of alkyl alcohols or acids (Tables 11 and 12). Thus, previously it had not gone unrecognized that endophytic fungi such as *Hypoxylon* sp. may have contributed to the breakdown of plant materials on the ancient earth with the subsequent entrapment of the fungal products by certain components of the earth such as shale which has been experimentally demonstrated (Booth et al., 2011, Biotechnol. Lett. 33:1963-1972). Although not wishing to be bound to any particular theory, it is surmised that heat and the reductive conditions found in the earth could have been responsible for further conversion of the more oxidized fungal products (i.e. alkyl alcohols and acids) to the more reduced alkanes. Although not wishing to be bound to any particular theory, it is proposed that these endophytes began the processes of plant tissue degradation at the time the host plant died since they are they represent the microbial community being the first to have access to the dead plant tissues (Strobel et al., 2008, Microbiology 154:3319-3328). Presently, there is a growing list of endophytic fungi making hydrocarbons and hydrocarbon derivatives (Tomcheck et al., 2010, Microb. Ecol. 60:903-914; Ahamedg and Ahring, 2011, Bioresour. TEchnol. 102:9718-9722; Griffin et al., 2010, Microbiology 156:3814-3829; Ul-Hassan et al., 2012, Microbiology 158:465-473; Singh et al., 2010, Microbial. Ecol. 61:729-739; Strobel et al., 2008, Microbiology 154:3319-3328; Strobel et al., 2011, FEMS Microbiol. Lett. 320:87-94).

The biological activity of the VOCs of this fungus is quite interesting given the fact that it expresses so much selectively (Table 13). For instance, a 2 day exposure to the gases of *Nodulisporium* sp. resulted in the death of both *A. fumigatus* as well as *R. solani*. The former is an as comycete and the latter is a basidiomycete. And although many other fungi were inhibited by the VOCs, there were a few in which there was no inhibition whatsoever and these include such fungi as *F. solani* and *P. ultimum*. Also, quite important is the observation that the collected and tested VOCs of the *Nodulisporium* sp. somewhat mimicked the activity of the actual fungus (Table 14). These results support the use of these experiments on fungi making biologically active VOCs.

Example 5

Ti-13, a *Nodulisporium* sp. Isolate

Figure 16:
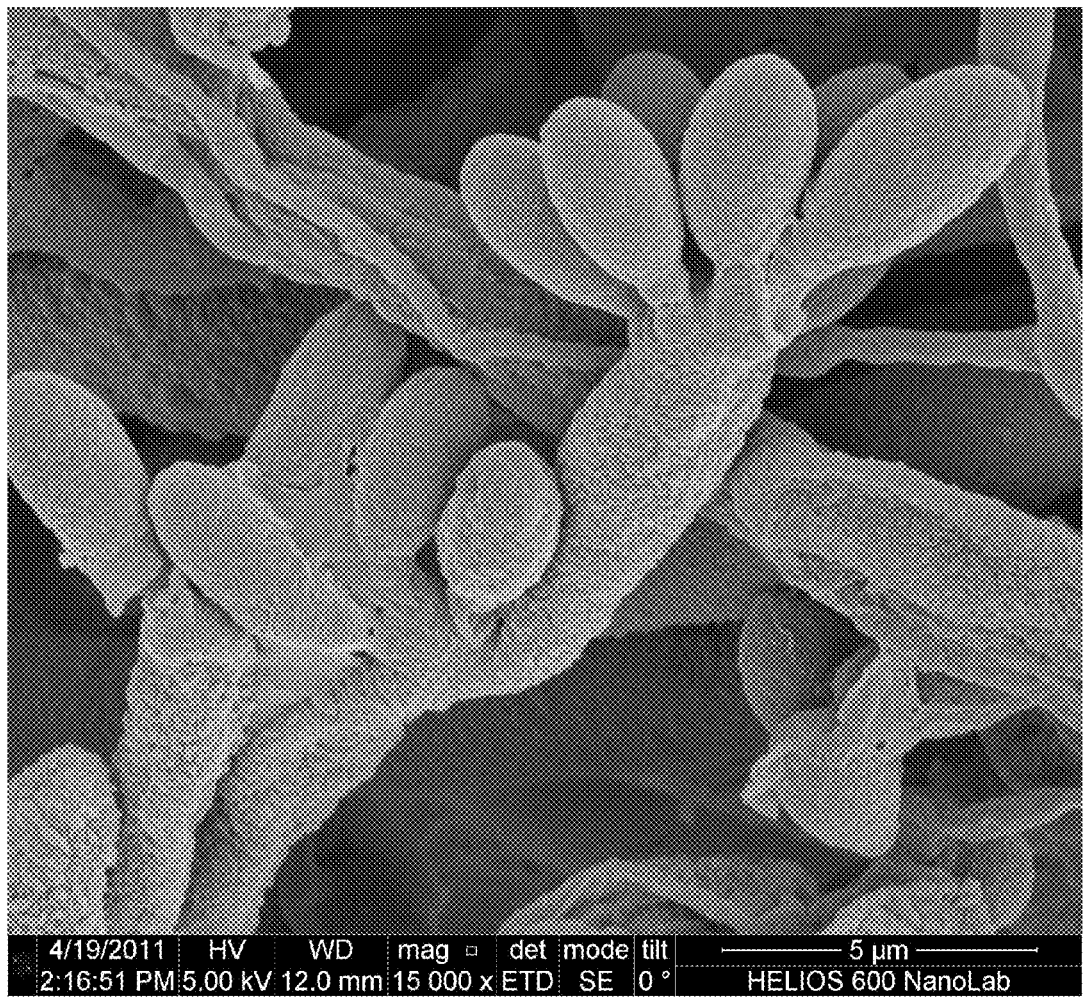
FIG. 16 is a SEM image of *Nodulisporium* sp. isolate Ti-13, which was isolated from *Cassia* sp. in the hills of western Thailand. Under SEM, Ti-13 looks identical to a *Nodulisporium* sp.
Figure 17:
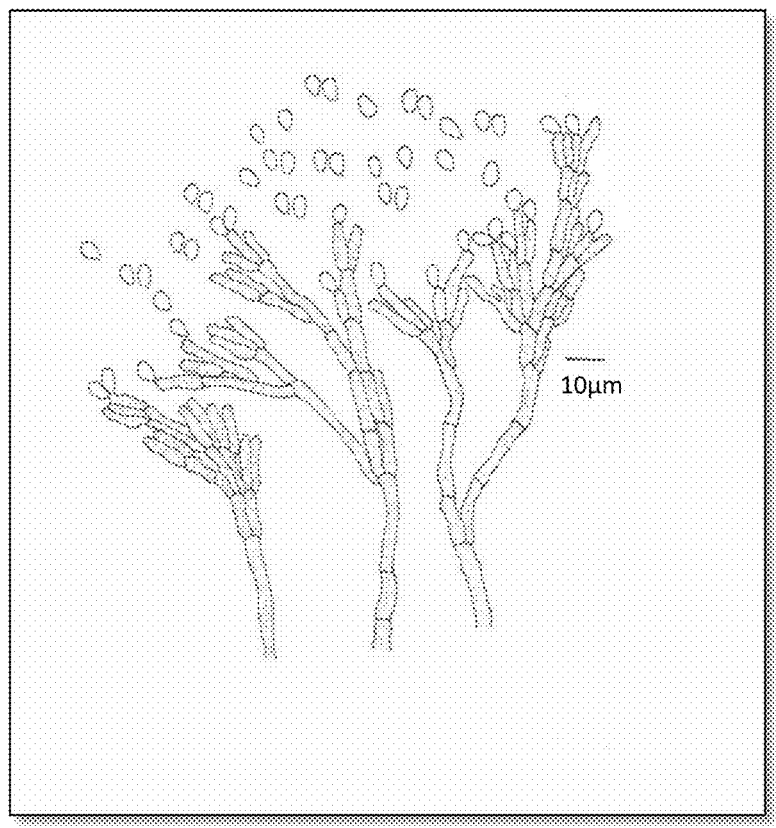
FIG. 17 is an illustration of *Nodulisporium* sp. isolate Ti-13. The spores are 5-6 microns×2.5 microns.
Figure 18:
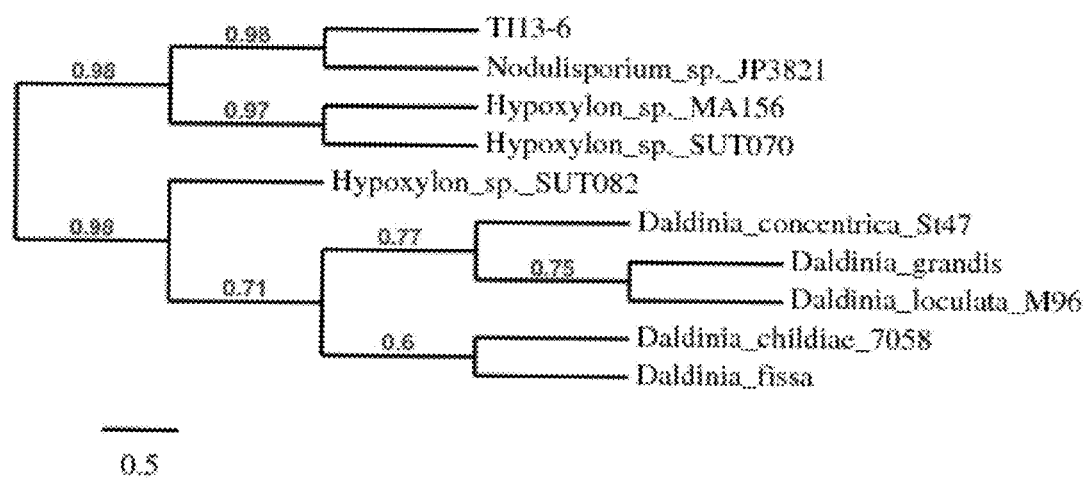
FIG. 18 is a dendogram of the Ti-13. The numbers designate the support branch values, confirming that Ti-13 is a *Nodulisporium* sp.

Ti-13, a *Nodulisporium* sp. isolate, was isolated from *Cassia* sp. in the hills of western Thailand. Under SEM, Ti-13 looks identical to a *Nodulisporium* sp. (FIG. 16). The spores of Ti-13 are 5-6 microns×$2.5^{-4}$ microns (FIG. 17). Dendogram analysis confirms that Ti-13 is a *Nodulisporium* sp. (FIG. 18). Ti-13 was found to produce 1,8-cineole, in addition to other VOCs (Table 15). Methods of isolating and analyzing VOCs produced by fungi are described elsewhere herein.

TABLE 15

VOCs produced by Ti-13, a *Nodulisporium* sp. isolate

| Retention Time | Relative Area | Name | Molecular Mass | Quality |
|---|---|---|---|---|
| 4.78 | 2.71 | 1,3,5- hexatriene, 3-methyl-, (Z) | 94 | 91 |
| 9.48 | 155.88 | cineole | 154 | 98 |
| 9.77 | 3.85 | 1-Butanol, 3-methyl- | 88 | 64 |
| 14.19 | 17.32 | Spiro [4.4] nona-1,6-diene, (S) | 120 | 74 |
| 22.15 | 1.85 | p-menth-1-en-8-ol | 154 | 91 |
| 23.02 | 28.74 | Dicyclobutylidene | 124 | 53 |
| 23.31 | 7.72 | ,4-Cyclooctadiene, 6-bromo- | 186 | 83 |
| 25.39 | 2.84 | 4-Hexenoic acid | 114 | 38 |
| 26.27 | 6.50 | 6a-Methyl-hexahydropentalene-1,6 | 152 | 62 |
| 26.91 | 3.95 | Phenylethyl Alcohol | 122 | 91 |
| 27.48 | 0.926 | 1-Ethynyl-1-cycloheptanol | 138 | 50 |
| 29.78 | 737.67 | 2,5-Methano-1H-inden-7(4H)-one | 150 | 53 |
| 29.91 | | | | |

Example 6

Th-9, a *Nodulisporium* sp. Isolate

Th-9, a *Nodulisporium* sp. isolate, was isolated from pomelo in the hills of western Thailand. Under SEM, Th-9 looks identical to a *Nodulisporium* sp. Th-9 was found to produce 18-cineole, in addition to other VOCs (Table 16). Methods of isolating and analyzing VOCs produced by fungi are described elsewhere herein.

TABLE 16

VOCs produced by Th-9, a *Nodulisporium* sp. isolate

| Retention Time (min) | Relative Area | Possible compound | Quality |
|---|---|---|---|
| 1.3 | 10.83 | Unknown | 4 |
| 1.51 | 1.91 | Unknown | 3 |
| 5.15 | 10.69 | 1,8-Cineole | 96 |
| 6.4 | 11.08 | Styrene* | 97 |
| 24.63 | 5.43 | Unknown | 64 |
| 24.82 | 7.83 | Unknown | 53 |
| 26.85 | 3.29 | Unknown | 35 |
| 27.73 | 7.13 | Unknown | 58 |
| 31.2 | 200.92 | Unknown | 68 |
| 31.46 | 2.59 | Unknown | 38 |
| 31.64 | 10.63 | Unknown | 68 |
| 31.81 | 3.67 | Unknown | 22 |
| 31.95 | 4.32 | Unknown | 50 |
| 32.06 | 2.21 | Unknown | 38 |
| 32.1 | 3.58 | Unknown | 43 |
| 32.2 | 3.08 | Unknown | 43 |
| 32.43 | 2.79 | Unknown | 47 |
| 32.55 | 2.63 | Unknown | 43 |
| 32.65 | 2.59 | Unknown | 38 |
| 32.85 | 30.33 | Unknown | 53 |

Total = 327.53

Example 7

Fl-9, a *Nodulisporium* sp. Isolate

Fl-9, a *Nodulisporium* sp. isolate, was isolated from *Taxodium distichum* from a swamp in Florida. Under SEM, Fl-9 looks identical to a *Nodulisporium* sp. Fl-9 was found to produce 1,8-cineole, in addition to other VOCs (Table 17). Methods of isolating and analyzing VOCs produced by fungi are described elsewhere herein.

TABLE 17

VOCs produced by Fl-9, a *Nodulisporium* sp. Isolate

| Compound | Retention Time | Relative Area (ng) | Relative Area (µg) | MW | Quality | Percent |
|---|---|---|---|---|---|---|
| 1-Propanol, 2-methyl- | 8.37 | 79.46 | 0.08 | 74 | 90 | 0.23% |
| 2-Hexanone, 4-methyl- | 8.82 | 132.80 | 0.13 | 114 | 90 | 0.38% |
| D-Limonene | 10.81 | 85.70 | 0.09 | 136 | 95 | 0.24% |
| cineole | 11.17 | 6153.56 | 6.15 | 154 | 99 | 17.45% |
| 1-Butanol, 3-methyl- | 11.41 | 1999.66 | 2.00 | 88 | 72 | 5.67% |
| 3-Heptanone, 5-ethyl-4-methyl- | 14.13 | 313.67 | 0.31 | 156 | 72 | 0.89% |
| cis-(−)-2,4a,5,6,9a-Hexahydro-3,5,5,9-tetramethyl(1H)benzocycloheptene | 18.32 | 146.86 | 0.15 | 204 | 89 | 0.42% |
| Himachala-2,4-diene | 19.43 | 122.17 | 0.12 | 204 | 87 | 0.35% |
| Tricyclo[5.4.0.0(2,8)]undec-9-ene, 2,6,6,9-tetramethyl-, (1R,2S,7R,8R)- | 20.20 | 257.54 | 0.26 | 204 | 93 | 0.73% |
| 10s,11s-Himachala-3(12),4-diene | 20.78 | 84.09 | 0.08 | 204 | 93 | 0.24% |
| Caryophyllene | 21.61 | 178.91 | 0.18 | 204 | 97 | 0.51% |

TABLE 17-continued

VOCs produced by Fl-9, a *Nodulisporium* sp. Isolate

| Compound | Retention Time | Relative Area (ng) | Relative Area (μg) | MW | Quality | Percent |
|---|---|---|---|---|---|---|
| Naphthalene, 1,2,3,4,4a,5,6,8a-octahydro-4a,8-dimethyl-2-(1-methylethylidene)-, (4aR-trans)- | 22.71 | 1516.84 | 1.52 | 204 | 79 | 4.30% |
| (+)-Epi-bicyclosesquiphellandrene | 23.10 | 89.86 | 0.09 | 204 | 89 | 0.25% |
| 1H-Benzocycloheptene, 2,4a,5,6,7,8,9,9a-octahydro-3,5,5-trimethyl-9-methylene-, (4aS-cis)- | 23.20 | 276.47 | 0.28 | 204 | 96 | 0.78% |
| .alpha.-Caryophyllene | 23.37 | 139.68 | 0.14 | 204 | 97 | 0.40% |
| Spiro[5.5]undec-2-ene, 3,7,7-trimethyl-11-methylene-, (−)- | 23.52 | 234.11 | 0.23 | 204 | 87 | 0.66% |
| 1H-3a,7-Methanoazulene, 2,3,4,7,8,8a-hexahydro-3,6,8,8-tetramethyl-, [3R-(3α,3aβ,7β,8aα)]- | 23.94 | 339.30 | 0.34 | 204 | 83 | 0.96% |
| Cycloheptane, 4-methylene-1-methyl-2-(2-methyl-1-propen-1-yl)-1-vinyl- | 24.26 | 236.25 | 0.24 | 204 | 93 | 0.67% |
| Azulene, 1,2,3,5,6,7,8,8a-octahydro-1,4-dimethyl-7-(1-methylethenyl)-, [1S-(1α,7α,8aβ)]- | 24.42 | 882.79 | 0.88 | 204 | 99 | 2.50% |
| Naphthalene, decahydro-4a-methyl-1-methylene-7-(1-methylethylidene)-, (4aR-trans)- | 24.65 | 264.82 | 0.26 | 204 | 74 | 0.75% |
| Epizonarene | 25.37 | 651.67 | 0.65 | 204 | 94 | 1.85% |
| Thujopsene | 25.56 | 155.35 | 0.16 | 204 | 70 | 0.44% |
| Phenylethyl Alcohol | 28.94 | 70.38 | 0.07 | 122 | 97 | 0.20% |
| Azulene, 1,2,3,5,6,7,8,8a-octahydro-1,4-dimethyl-7-(1-methylethenyl)-, [1S-(1α,7α,8aβ)]- | 34.63 | 4055.72 | 4.06 | 204 | 92 | 11.50% |
| 19 Unknowns | — | 16793.55 | 16.79 | — | 70 | 47.63% |
| Total |  | 35261.21 | 35.26 |  |  |  |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for producing at least one compound selected from the group consisting of 1,8-cineole and 1-methyl-1,4-cyclohexadiene, comprising:
    culturing an endophytic fungus that has the imperfect stage of *Nodulisporium* on or within a culturing media in a container under conditions sufficient for producing the at least one compound; and
    isolating the at least one compound from the container or culturing media.

2. The method of claim 1, wherein the fungus is from the genus *Nodulisporium*.

3. The method of claim 1, wherein the fungus is from the genus *Hypoxylon*.

4. The method of claim 1, wherein the fungus is from the genus *Annulohypoxylon*.

5. The method of claim 1, wherein the fungus is from the genus *Daldinia*.

6. The method of claim 1, wherein the fungus is from the genus *Xylaria*.

7. The method of claim 1, wherein the fungus is serially propagated.

8. The method of claim 1, wherein the fungus is grown on or in a high-starch substrate.

9. The method of claim 1, wherein the fungus is grown in a liquid medium.

10. The method of claim 1, wherein the fungus is grown on a solid medium.

11. The method of claim 1, wherein the at least one compound is isolated from a vapor produced within the container.

* * * * *